United States Patent
Virdee et al.

(10) Patent No.: US 10,829,799 B2
(45) Date of Patent: Nov. 10, 2020

(54) CYSTEINE LABELLING

(71) Applicant: University of Dundee, Dundee (GB)

(72) Inventors: Satpal Virdee, Dundee (GB); Mathew Stanley, Dundee (GB); Kuan-Chuan Pao, Dundee (GB)

(73) Assignee: UNIVERSITY COURT OF THE UNIVERSITY OF DUNDEE, Dundee (GB)

(*) Notice: Subject to any disclaimer, the term of this patent is extended or adjusted under 35 U.S.C. 154(b) by 0 days.

(21) Appl. No.: 15/515,374

(22) PCT Filed: Sep. 30, 2015

(86) PCT No.: PCT/GB2015/052860
§ 371 (c)(1),
(2) Date: Mar. 29, 2017

(87) PCT Pub. No.: WO2016/051174
PCT Pub. Date: Apr. 7, 2016

(65) Prior Publication Data
US 2017/0233788 A1 Aug. 17, 2017

(30) Foreign Application Priority Data
Sep. 30, 2014 (GB) .................................. 1417288.6

(51) Int. Cl.
*C12Q 1/48* (2006.01)
*G01N 33/532* (2006.01)
*C12Q 1/44* (2006.01)

(52) U.S. Cl.
CPC ................. *C12Q 1/48* (2013.01); *C12Q 1/44* (2013.01); *G01N 33/532* (2013.01); *G01N 2333/9108* (2013.01)

(58) Field of Classification Search
CPC .... C12Q 1/44; C12Q 1/48; G01N 2333/9108; G01N 33/532
See application file for complete search history.

(56) References Cited

U.S. PATENT DOCUMENTS

| 4,266,040 A * | 5/1981 | Lin ............................ C08J 9/02 521/128 |
| 2006/0088901 A1 | 4/2006 | Li et al. |
| 2010/0151484 A1* | 6/2010 | Vogel ........................ C12Q 1/37 435/7.1 |

FOREIGN PATENT DOCUMENTS

| WO | 03/091411 A2 | 11/2003 | |
| WO | 2011/079315 | 6/2011 | |
| WO | WO-2013155526 A2 * | 10/2013 | ......... C07K 16/1018 |
| WO | WO-2014183066 A2 * | 11/2014 | ......... A61K 39/0011 |

OTHER PUBLICATIONS

Jana et al. J. Org. Chem. (2013) 78: 2680-2686 (Year: 2013).*
Shui et al. Chem. Eur. J. (2009) 15: 3839-3850 (Year: 2009).*
Hoffman et al. Synth. Comm. (2014; published online Nov. 8, 2013) 44: 976-980 (Year: 2014).*
Pruneda et al. Biochemistry (2011) 50(10): 1624-1633 (Year: 2011).*
Pia et al. Nature (2009) 461(7260): 114-119 (Year: 2009).*
Weikert et al. ChemBioChem (2010) 11: 774-777 (Year: 2010).*
International Search Report and Written Opinion for corresponding PCT Application PCT/GB2015/052860, dated Jan. 4, 2016, pp. 1-16.
Kolb, H. C., et al., "Click Chemistry: Diverse Chemical Function from a few good reactions", Angewandte Chemie International Edition, May 2001, pp. 2004-2021, vol. 40, No. 11.
Candan, O. A., et al., "Quadruple click reactions for synthesis of cysteine-functional heterograft brush copolymer," European Polymer Journal, Apr. 2013, pp. 1796-1802, vol. 49, No. 7.
Jena Bioscience, "Click Chemistry background information", Jena Bioscience GmbH, Mar. 2015, pp. 1-5.
Hodge, C.D, et al., "Covalent Inhibition of Ubc13 Affects Ubiquitin Signaling and Reveals Active Site Elements Important for Targeting," ACS Chemical Biology 2015, vol. 10, pp. 1718-1728.
Strickson, S., et al., "The anti-inflammatory drug BAY 11-7082 suppresses the MyD88-dependant signalling network by targeting the ubiquitin system," Biochemical Society 2013, vol. 451, pp. 427-437.
ISA/GB: Search Report, Great Britain Patent Application No. GB1417288.6, dated Jul. 13, 2015, pp. 1-4.
Gan-Erdene et al., "Identification and Characterization of DEN1, a Deneddylase of the ULP Family" The Journal of Biology Chem 2003, vol. 278, pp. 28892-28900.
Stanley, "Orthogonal Thiol Functionalization at a Single Atomic Center for Profiling Transthiolation Activity of E1 Activating Enzymes," ACS Chemical Biology 2015, vol. 10, pp. 1542-1554.

* cited by examiner

*Primary Examiner* — Susan M Hanley
(74) *Attorney, Agent, or Firm* — Wolter Van Dyke Davis, PLLC; Eugene J. Molinelli; Martha Cassidy

(57) ABSTRACT

The present invention relates to the production of activated biological molecules for use in profiling biological molecule interactions. The activated biological molecule may be a ubiquitin (Ub) and ubiquitin-like conjugation enzyme as well as other proteins with internal reactive cysteine residues.

8 Claims, 31 Drawing Sheets

Specification includes a Sequence Listing.

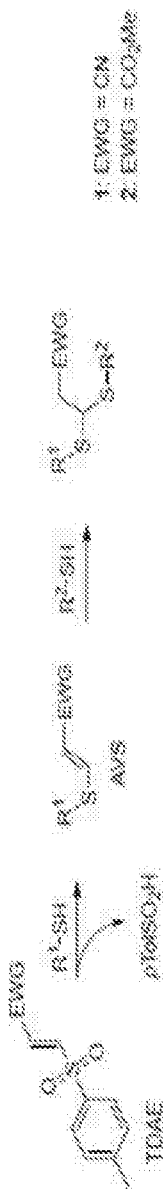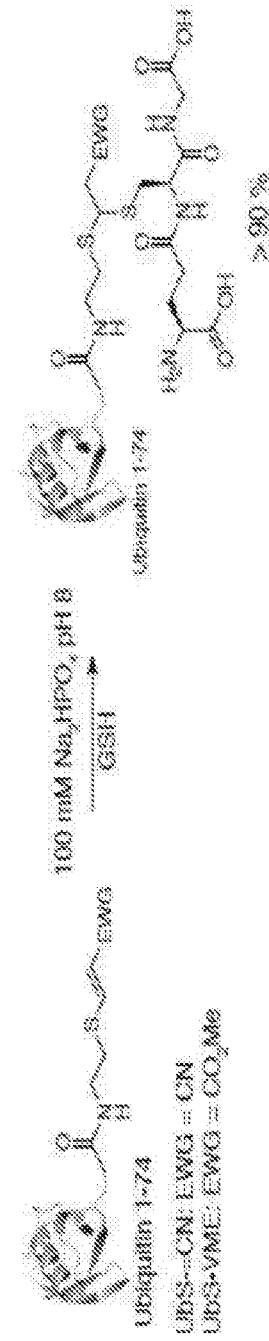
Figure 2A
Figure 2B

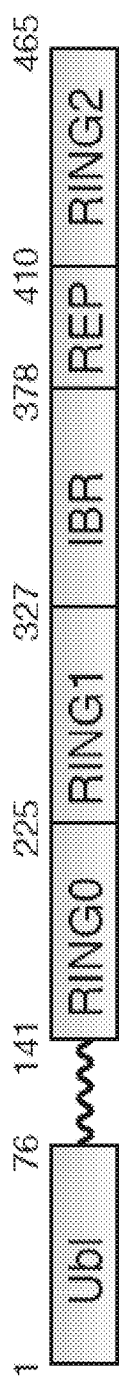
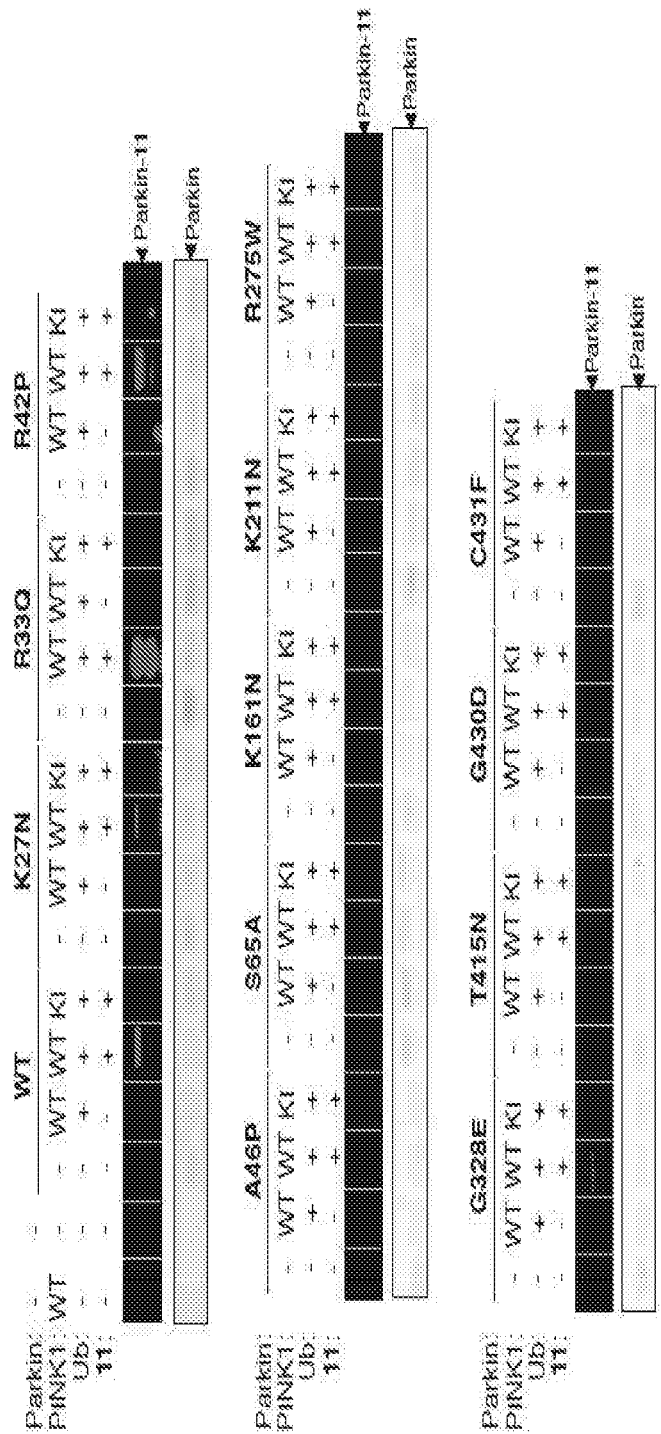
Figure 9a
Figure 9b

SEQUENCE LISTING

<160> NUMBER OF SEQ ID NOS: 19

<210> SEQ ID NO 1
<211> LENGTH: 180
<212> TYPE: PRT
<213> ORGANISM: Homo sapiens

<400> SEQUENCE: 1

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Ala Leu Lys Arg Ile Gln Lys Glu Leu Ser Asp Leu Gln Arg
        35                  40                  45

Asp Pro Pro Ala His Cys Ser Ala Gly Pro Val Gly Asp Asp Leu Phe
    50                  55                  60

His Trp Gln Ala Thr Ile Met Gly Pro Pro Asp Ser Ala Tyr Gln Gly
65                  70                  75                  80

Gly Val Phe Phe Leu Thr Val His Phe Pro Thr Asp Tyr Pro Phe Lys
                85                  90                  95

Pro Pro Lys Ile Ala Phe Thr Thr Lys Ile Tyr His Pro Asn Ile Asn
            100                 105                 110

Ser Asn Gly Ser Ile Cys Leu Asp Ile Leu Arg Ser Gln Trp Ser Pro
        115                 120                 125

```
Ala Leu Thr Val Ser Lys Val Leu Leu Ser Ile Cys Ser Leu Leu Cys
            130                 135                 140

Asp Pro Asn Pro Asp Asp Pro Leu Val Pro Asp Ile Ala Gln Ile Tyr
145                 150                 155                 160

Lys Ser Asp Lys Glu Lys Tyr Asn Arg His Ala Arg Glu Trp Thr Gln
                165                 170                 175

Lys Tyr Ala Met
            180

<210> SEQ ID NO 2
<211> LENGTH: 176
<212> TYPE: PRT
<213> ORGANISM: Homo sapiens

<400> SEQUENCE: 2

Met Ser Tyr Tyr His His His His His Asp Tyr Asp Ile Pro Thr
1               5                   10                  15

Thr Glu Asn Leu Tyr Phe Gln Gly Ala Gly Ser Gly Ser Met Ala Leu
            20                  25                  30

Lys Arg Ile Gln Lys Glu Leu Ser Asp Leu Gln Arg Asp Pro Pro Ala
        35                  40                  45

His Ser Ser Ala Gly Pro Val Gly Asp Asp Leu Phe His Trp Gln Ala
    50                  55                  60

Thr Ile Met Gly Pro Pro Asp Ser Ala Tyr Gln Gly Gly Val Phe Phe
65                  70                  75                  80

Leu Thr Val His Phe Pro Thr Asp Tyr Pro Phe Lys Pro Pro Lys Ile
                85                  90                  95

Ala Phe Thr Thr Lys Ile Tyr His Pro Asn Ile Asn Ser Asn Gly Ser
            100                 105                 110

Ile Cys Leu Asp Ile Leu Arg Ser Gln Trp Ser Pro Ala Leu Thr Val
        115                 120                 125

Ser Lys Val Leu Leu Ser Ile Ser Ser Leu Leu Ser Asp Pro Asn Pro
    130                 135                 140

Asp Asp Pro Leu Val Pro Asp Ile Ala Gln Ile Tyr Lys Ser Asp Lys
145                 150                 155                 160

Glu Lys Tyr Asn Arg His Ala Arg Glu Trp Thr Gln Lys Tyr Ala Met
                165                 170                 175

<210> SEQ ID NO 3
<211> LENGTH: 176
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 3

Met Ser Xaa Tyr His His His His His Asp Tyr Asp Ile Pro Thr
1               5                   10                  15

Thr Glu Asn Leu Tyr Phe Gln Gly Ala Gly Ser Gly Ser Met Ala Leu
            20                  25                  30

Lys Arg Ile Gln Lys Glu Leu Ser Asp Leu Gln Arg Asp Pro Pro Ala
        35                  40                  45

His Ser Ser Ala Gly Pro Val Gly Asp Asp Leu Phe His Trp Gln Ala
    50                  55                  60

Thr Ile Met Gly Pro Pro Asp Ser Ala Tyr Gln Gly Gly Val Phe Phe
65                  70                  75                  80
```

```
Leu Thr Val His Phe Pro Thr Asp Tyr Pro Phe Lys Pro Pro Lys Ile
                85                  90                  95

Ala Phe Thr Thr Lys Ile Tyr His Pro Asn Ile Asn Ser Asn Gly Ser
            100                 105                 110

Ile Cys Leu Asp Ile Leu Arg Ser Gln Trp Ser Pro Ala Leu Thr Val
            115                 120                 125

Ser Lys Val Leu Leu Ser Ile Ser Ser Leu Leu Ser Asp Pro Asn Pro
        130                 135                 140

Asp Asp Pro Leu Val Pro Asp Ile Ala Gln Ile Tyr Lys Ser Asp Lys
145                 150                 155                 160

Glu Lys Tyr Asn Arg His Ala Arg Glu Trp Thr Gln Lys Tyr Ala Met
                165                 170                 175

<210> SEQ ID NO 4
<211> LENGTH: 180
<212> TYPE: PRT
<213> ORGANISM: Homo sapiens

<400> SEQUENCE: 4

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Ala Leu Lys Arg Ile His Lys Glu Leu Asn Asp Leu Ala Arg
        35                  40                  45

Asp Pro Pro Ala Gln Cys Ser Ala Gly Pro Val Gly Asp Asp Met Phe
    50                  55                  60

His Trp Gln Ala Thr Ile Met Gly Pro Asn Asp Ser Pro Tyr Gln Gly
65                  70                  75                  80

Gly Val Phe Phe Leu Thr Ile His Phe Pro Thr Asp Tyr Pro Phe Lys
                85                  90                  95

Pro Pro Lys Val Ala Phe Thr Thr Arg Ile Tyr His Pro Asn Ile Asn
            100                 105                 110

Ser Asn Gly Ser Ile Cys Leu Asp Ile Leu Arg Ser Gln Trp Ser Pro
        115                 120                 125

Ala Leu Thr Ile Ser Lys Val Leu Leu Ser Ile Cys Ser Leu Leu Cys
    130                 135                 140

Asp Pro Asn Pro Asp Asp Pro Leu Val Pro Glu Ile Ala Arg Ile Tyr
145                 150                 155                 160

Lys Thr Asp Arg Glu Lys Tyr Asn Arg Ile Ala Arg Glu Trp Thr Gln
                165                 170                 175

Lys Tyr Ala Met
            180

<210> SEQ ID NO 5
<211> LENGTH: 169
<212> TYPE: PRT
<213> ORGANISM: Homo sapiens

<400> SEQUENCE: 5

Met Gly Ser Ser His His His His His His Ser Ser Gly Leu Glu Val
1               5                   10                  15

Leu Phe Gln Gly Pro Gly Ser Ala Leu Lys Arg Ile Asn Lys Glu Leu
            20                  25                  30

Ser Asp Leu Ala Arg Asp Pro Pro Ala Gln Cys Ser Ala Gly Pro Val
        35                  40                  45
```

```
Gly Asp Asp Met Phe His Trp Gln Ala Thr Ile Met Gly Pro Asn Asp
    50                  55                  60
Ser Pro Tyr Gln Gly Gly Val Phe Phe Leu Thr Ile His Phe Pro Thr
65                  70                  75                  80
Asp Tyr Pro Phe Lys Pro Pro Lys Val Ala Phe Thr Thr Arg Ile Tyr
                85                  90                  95
His Pro Asn Ile Asn Ser Asn Gly Ser Ile Cys Leu Asp Ile Leu Arg
                100                 105                 110
Ser Gln Trp Ser Pro Ala Leu Thr Ile Ser Lys Val Leu Leu Ser Ile
            115                 120                 125
Cys Ser Leu Leu Cys Asp Pro Asn Pro Asp Asp Pro Leu Val Pro Glu
    130                 135                 140
Ile Ala Arg Ile Tyr Lys Thr Asp Arg Asp Lys Tyr Asn Arg Ile Ser
145                 150                 155                 160
Arg Glu Trp Thr Gln Lys Tyr Ala Met
                165

<210> SEQ ID NO 6
<211> LENGTH: 177
<212> TYPE: PRT
<213> ORGANISM: Homo sapiens

<400> SEQUENCE: 6

Met Gly Ser Ser His His His His His His Ser Ser Gly Leu Glu Val
1               5                   10                  15
Leu Phe Gln Gly Pro Gly Ser Met Ala Ala Ser Arg Arg Leu Met Lys
                20                  25                  30
Glu Leu Glu Glu Ile Arg Lys Ser Gly Met Lys Asn Phe Arg Asn Ile
            35                  40                  45
Gln Val Asp Glu Ala Asn Leu Leu Thr Trp Gln Gly Leu Ile Val Pro
    50                  55                  60
Asp Asn Pro Pro Tyr Asp Lys Gly Ala Phe Arg Ile Glu Ile Asn Phe
65                  70                  75                  80
Pro Ala Glu Tyr Pro Phe Lys Pro Pro Lys Ile Thr Phe Lys Thr Lys
                85                  90                  95
Ile Tyr His Pro Asn Ile Asp Glu Lys Gly Gln Val Cys Leu Pro Val
                100                 105                 110
Ile Ser Ala Glu Asn Trp Lys Pro Ala Thr Lys Thr Asp Gln Val Ile
            115                 120                 125
Gln Ser Leu Ile Ala Leu Val Asn Asp Pro Gln Pro Glu His Pro Leu
    130                 135                 140
Arg Ala Asp Leu Ala Glu Glu Tyr Ser Lys Asp Arg Lys Lys Phe Ser
145                 150                 155                 160
Lys Asn Ala Glu Glu Phe Thr Lys Lys Tyr Gly Glu Lys Arg Pro Val
                165                 170                 175
Asp

<210> SEQ ID NO 7
<211> LENGTH: 177
<212> TYPE: PRT
<213> ORGANISM: Homo sapiens
```

<400> SEQUENCE: 7

```
Met Gly Ser Ser His His His His His Ser Ser Gly Leu Glu Val
1               5                   10                  15

Leu Phe Gln Gly Pro Gly Ser Met Ala Ala Ser Arg Arg Leu Met Lys
                20                  25                  30

Glu Leu Glu Glu Ile Arg Lys Ser Gly Met Lys Asn Phe Arg Asn Ile
            35                  40                  45

Gln Val Asp Glu Ala Asn Leu Leu Thr Trp Gln Gly Leu Ile Val Pro
    50                  55                  60

Asp Asn Pro Pro Tyr Asp Lys Gly Ala Phe Arg Ile Glu Ile Asn Phe
65                  70                  75                  80

Pro Ala Glu Tyr Pro Phe Lys Pro Lys Ile Thr Phe Lys Thr Lys
                85                  90                  95

Ile Tyr His Pro Asn Ile Asp Glu Lys Gly Gln Val Cys Leu Pro Val
            100                 105                 110

Ile Ala Ala Glu Asn Trp Lys Pro Ala Thr Lys Thr Asp Gln Val Ile
        115                 120                 125

Gln Ser Leu Ile Ala Leu Val Asn Asp Pro Gln Pro Glu His Pro Leu
    130                 135                 140

Arg Ala Asp Leu Ala Glu Glu Tyr Ser Lys Asp Arg Lys Lys Phe Ser
145                 150                 155                 160

Lys Asn Ala Glu Glu Phe Thr Lys Lys Tyr Gly Glu Lys Arg Pro Val
                165                 170                 175

Asp
```

<210> SEQ ID NO 8
<211> LENGTH: 176
<212> TYPE: PRT
<213> ORGANISM: Homo sapiens

<400> SEQUENCE: 8

```
Met Gly Ser Ser His His His His His Ser Ser Gly Leu Glu Val
1               5                   10                  15

Leu Phe Gln Gly Pro Gly Ser Met Met Ala Ser Met Arg Val Val Lys
                20                  25                  30

Glu Leu Glu Asp Leu Gln Lys Lys Pro Pro Tyr Leu Arg Asn Leu
            35                  40                  45

Ser Ser Asp Asp Ala Asn Val Leu Val Trp His Ala Leu Leu Leu Pro
    50                  55                  60

Asp Gln Pro Pro Tyr His Leu Lys Ala Phe Asn Leu Arg Ile Ser Phe
65                  70                  75                  80

Pro Pro Glu Tyr Pro Phe Lys Pro Pro Met Ile Lys Phe Thr Thr Lys
                85                  90                  95

Ile Tyr His Pro Asn Val Asp Glu Asn Gly Gln Ile Cys Leu Pro Ile
            100                 105                 110

Ile Ser Ser Glu Asn Trp Lys Pro Ser Thr Lys Thr Ser Gln Val Leu
        115                 120                 125

Glu Ala Leu Asn Val Leu Val Asn Arg Pro Asn Ile Arg Glu Pro Leu
    130                 135                 140

Arg Met Asp Leu Ala Asp Leu Leu Thr Gln Asn Pro Glu Leu Phe Arg
145                 150                 155                 160

Lys Asn Ala Glu Glu Phe Thr Leu Arg Phe Gly Val Asp Arg Pro Ser
                165                 170                 175
```

<210> SEQ ID NO 9
<211> LENGTH: 176
<212> TYPE: PRT
<213> ORGANISM: Homo sapiens

<400> SEQUENCE: 9

Met Gly Ser Ser His His His His His His Ser Ser Gly Leu Glu Val
1               5                   10                  15

Leu Phe Gln Gly Pro Gly Ser Met Met Ala Ser Met Arg Val Val Lys
                20                  25                  30

Glu Leu Glu Asp Leu Gln Lys Lys Pro Pro Tyr Leu Arg Asn Leu
            35                  40                  45

Ser Ser Asp Asp Ala Asn Val Leu Val Trp His Ala Leu Leu Leu Pro
    50                  55                  60

Asp Gln Pro Pro Tyr His Leu Lys Ala Phe Asn Leu Arg Ile Ser Phe
65                  70                  75                  80

Pro Pro Glu Tyr Pro Phe Lys Pro Pro Met Ile Lys Phe Thr Thr Lys
                85                  90                  95

Ile Tyr His Pro Asn Val Asp Glu Asn Gly Gln Ile Cys Leu Pro Ile
                100                 105                 110

Ile Ala Ser Glu Asn Trp Lys Pro Ser Thr Lys Thr Ser Gln Val Leu
            115                 120                 125

Glu Ala Leu Asn Val Leu Val Asn Arg Pro Asn Ile Arg Glu Pro Leu
        130                 135                 140

Arg Met Asp Leu Ala Asp Leu Leu Thr Gln Asn Pro Glu Leu Phe Arg
145                 150                 155                 160

Lys Asn Ala Glu Glu Phe Thr Leu Arg Phe Gly Val Asp Arg Pro Ser
                165                 170                 175

<210> SEQ ID NO 10
<211> LENGTH: 174
<212> TYPE: PRT
<213> ORGANISM: Homo sapiens

<400> SEQUENCE: 10

Met Gly Ser Ser His His His His His His Ser Ser Gly Leu Glu Val
1               5                   10                  15

Leu Phe Gln Gly Pro Gly Ser Ala Gly Leu Pro Arg Arg Ile Ile Lys
                20                  25                  30

Glu Thr Gln Arg Leu Leu Ala Glu Pro Val Pro Gly Ile Lys Ala Glu
            35                  40                  45

Pro Asp Glu Ser Asn Ala Arg Tyr Phe His Val Val Ile Ala Gly Pro
    50                  55                  60

Gln Asp Ser Pro Phe Glu Gly Gly Thr Phe Lys Leu Glu Leu Phe Leu
65                  70                  75                  80

Pro Glu Glu Tyr Pro Met Ala Ala Pro Lys Val Arg Phe Met Thr Lys
                85                  90                  95

Ile Tyr His Pro Asn Val Asp Lys Leu Gly Arg Ile Cys Leu Asp Ile
                100                 105                 110

Leu Lys Asp Lys Trp Ser Pro Ala Leu Gln Ile Arg Thr Val Leu Leu
            115                 120                 125

Ser Ile Gln Ala Leu Leu Ser Ala Pro Asn Pro Asp Asp Pro Leu Ala
        130                 135                 140

```
Asn Asp Val Ala Glu Gln Trp Lys Thr Asn Glu Ala Gln Ala Ile Glu
145                 150                 155                 160
Thr Ala Arg Ala Trp Thr Arg Leu Tyr Ala Met Asn Asn Ile
                165                 170
```

<210> SEQ ID NO 11
<211> LENGTH: 206
<212> TYPE: PRT
<213> ORGANISM: Homo sapiens

<400> SEQUENCE: 11

```
Met Gly Ser Ser His His His His His His Ser Ser Gly Leu Glu Val
1               5                   10                  15
Leu Phe Gln Gly Pro Gly Ser Met Ser Ser Pro Ser Pro Gly Lys Arg
                20                  25                  30
Arg Met Asp Thr Asp Val Val Lys Leu Ile Glu Ser Lys His Glu Val
                35                  40                  45
Thr Ile Leu Gly Gly Leu Asn Glu Phe Val Val Lys Phe Tyr Gly Pro
50                  55                  60
Gln Gly Thr Pro Tyr Glu Gly Gly Val Trp Lys Val Arg Val Asp Leu
65                  70                  75                  80
Pro Asp Lys Tyr Pro Phe Lys Ser Pro Ser Ile Gly Phe Met Asn Lys
                85                  90                  95
Ile Phe His Pro Asn Ile Asp Glu Ala Ser Gly Thr Val Cys Leu Asp
                100                 105                 110
Val Ile Asn Gln Thr Trp Thr Ala Leu Tyr Asp Leu Thr Asn Ile Phe
                115                 120                 125
Glu Ser Phe Leu Pro Gln Leu Leu Ala Tyr Pro Asn Pro Ile Asp Pro
130                 135                 140
Leu Asn Gly Asp Ala Ala Ala Met Tyr Leu His Arg Pro Glu Glu Tyr
145                 150                 155                 160
Lys Gln Lys Ile Lys Glu Tyr Ile Gln Lys Tyr Ala Thr Glu Glu Ala
                165                 170                 175
Leu Lys Glu Gln Glu Glu Gly Thr Gly Asp Ser Ser Ser Glu Ser Ser
                180                 185                 190
Met Ser Asp Phe Ser Glu Asp Glu Ala Gln Asp Met Glu Leu
                195                 200                 205
```

<210> SEQ ID NO 12
<211> LENGTH: 181
<212> TYPE: PRT
<213> ORGANISM: Homo sapiens

<400> SEQUENCE: 12

```
Met Gly Ser Ser His His His His His His Ser Ser Gly Leu Glu Val
1               5                   10                  15
Leu Phe Gln Gly Pro Gly Ser Met Ser Gly Ile Ala Leu Ser Arg Leu
                20                  25                  30
Ala Gln Glu Arg Lys Ala Trp Arg Lys Asp His Pro Phe Gly Phe Val
                35                  40                  45
Ala Val Pro Thr Lys Asn Pro Asp Gly Thr Met Asn Leu Met Asn Trp
50                  55                  60
Glu Cys Ala Ile Pro Gly Lys Lys Gly Thr Pro Trp Glu Gly Gly Leu
65                  70                  75                  80
Phe Lys Leu Arg Met Leu Phe Lys Asp Asp Tyr Pro Ser Ser Pro Pro
                85                  90                  95
```

```
Lys Cys Lys Phe Glu Pro Pro Leu Phe His Pro Asn Val Tyr Pro Ser
            100                 105                 110
Gly Thr Val Cys Leu Ser Ile Leu Glu Glu Asp Lys Asp Trp Arg Pro
            115                 120                 125
Ala Ile Thr Ile Lys Gln Ile Leu Leu Gly Ile Gln Glu Leu Leu Asn
            130                 135                 140
Glu Pro Asn Ile Gln Asp Pro Ala Gln Ala Glu Ala Tyr Thr Ile Tyr
145                 150                 155                 160
Cys Gln Asn Arg Val Glu Tyr Glu Lys Arg Val Arg Ala Gln Ala Lys
                165                 170                 175
Lys Phe Ala Pro Ser
            180

<210> SEQ ID NO 13
<211> LENGTH: 218
<212> TYPE: PRT
<213> ORGANISM: Homo sapiens

<400> SEQUENCE: 13

Met Gly Ser Ser His His His His His His Ser Ser Gly Leu Glu Val
1               5                   10                  15
Leu Phe Gln Gly Pro Gly Ser Pro Glu Phe Pro Gly Val Asp Ser Lys
                20                  25                  30
Ala Ala Ala Met Ile Lys Leu Phe Ser Leu Lys Gln Gln Lys Lys Glu
            35                  40                  45
Glu Glu Ser Ala Gly Gly Thr Lys Gly Ser Ser Lys Lys Ala Ser Ala
        50                  55                  60
Ala Gln Leu Arg Ile Gln Lys Asp Ile Asn Glu Leu Asn Leu Pro Lys
65                  70                  75                  80
Thr Cys Asp Ile Ser Phe Ser Asp Pro Asp Leu Leu Asn Phe Lys
                85                  90                  95
Leu Val Ile Cys Pro Asp Glu Gly Phe Tyr Lys Ser Gly Lys Phe Val
            100                 105                 110
Phe Ser Phe Lys Val Gly Gln Gly Tyr Pro His Asp Pro Pro Lys Val
            115                 120                 125
Lys Cys Glu Thr Met Val Tyr His Pro Asn Ile Asp Leu Glu Gly Asn
            130                 135                 140
Val Cys Leu Asn Ile Leu Arg Glu Asp Trp Lys Pro Val Leu Thr Ile
145                 150                 155                 160
Asn Ser Ile Ile Tyr Gly Leu Gln Tyr Leu Phe Leu Glu Pro Asn Pro
                165                 170                 175
Glu Asp Pro Leu Asn Lys Glu Ala Ala Glu Val Leu Gln Asn Asn Arg
            180                 185                 190
Arg Leu Phe Glu Gln Asn Val Gln Arg Ser Met Arg Gly Gly Tyr Ile
            195                 200                 205
Gly Ser Thr Tyr Phe Glu Arg Cys Leu Lys
        210                 215

<210> SEQ ID NO 14
<211> LENGTH: 31
<212> TYPE: DNA
<213> ORGANISM: Artificial Sequence
<220> FEATURE:
<223> OTHER INFORMATION: oligo

<400> SEQUENCE: 14
gtcttaagac tgcgttgcat cacgggagat g                              31
```

```
<210> SEQ ID NO 15
<211> LENGTH: 31
<212> TYPE: DNA
<213> ORGANISM: Artificial Sequence
<220> FEATURE:
<223> OTHER INFORMATION: oligo

<400> SEQUENCE: 15
catctcccgt gatgcaacgc agtcttaaga c                              31

<210> SEQ ID NO 16
<211> LENGTH: 37
<212> TYPE: DNA
<213> ORGANISM: Artificial Sequence
<220> FEATURE:
<223> OTHER INFORMATION: oligo

<400> SEQUENCE: 16
ggagatatac atatgtcgta gtaccatcac catcacc                        37

<210> SEQ ID NO 17
<211> LENGTH: 37
<212> TYPE: DNA
<213> ORGANISM: Artificial Sequence
<220> FEATURE:
<223> OTHER INFORMATION: oligo

<400> SEQUENCE: 17
ggtgatggtg atggtactac gacatatgta tatctcc                        37

<210> SEQ ID NO 18
<211> LENGTH: 30
<212> TYPE: DNA
<213> ORGANISM: Artificial Sequence
<220> FEATURE:
<223> OTHER INFORMATION: oligo

<400> SEQUENCE: 18
agattgagat ctatggacga gttcgaaatg                                30

<210> SEQ ID NO 19
<211> LENGTH: 34
<212> TYPE: DNA
<213> ORGANISM: Artificial Sequence
<220> FEATURE:
<223> OTHER INFORMATION: oligo

<400> SEQUENCE: 19
agttgggtcg acttataatc tctttctaat tggc                           34
```

CYSTEINE LABELLING

CROSS REFERENCE TO RELATED APPLICATIONS

This application is a 371 national stage application of PCT Application No. PCT/GB2015/052860 filed Sep. 30, 2015, and claims benefit of GB Application No. 1417288.6, filed Sep. 30, 2014, the entire contents of each of which are hereby incorporated by reference as if fully set forth herein, under 35 U.S.C. § 119(e).

REFERENCE TO SEQUENCE LISTING SUBMITTED VIA EFS-WEB

This application includes an electronically submitted sequence listing in .txt format. The .txt file contains a sequence listing entitled "PE956631US_Sequence_Listing.txt" created on Mar. 29, 2017 and is 22 KB in size. The sequence listing contained in this .txt file is part of the specification and is hereby incorporated by reference herein in its entirety.

FIELD OF THE INVENTION

The present invention relates to the production of activated biological molecules for use in profiling biological molecule interactions. The activated biological molecule may be a ubiquitin (Ub) and ubiquitin-like conjugation enzyme as well as other proteins with internal reactive cysteine residues.

BACKGROUND TO THE INVENTION

Activity-based protein profiling (ABPP) has emerged as a powerful chemical proteomic strategy which allows characterization of enzyme function directly in native biological systems on a global scale.

ABPP relies on the design of active-site directed covalent probes to interrogate specific subsets (families) of enzymes in complex proteomes and to provide the basis for a quantitative readout of the functional state of individual enzymes in the family.

ABPP probes utilize a range of chemical scaffolds, including mechanism-based inhibitors, protein-reactive natural products, and general electrophiles. Activity-based probes (irreversible covalent inhibitors with reporter groups) for identification and mechanistic study of deubiquitinating enzymes by ABPP are known. These activity-based probes (ABPs) have been developed to selectively target only deubiquitinating enzymes which are enzymatically active at a certain time point. Specifically, the ABPs allow the characterization of the otherwise not accessible deubiquitinating enzymes sub-proteome and the identification of previously unknown deubiquitinating enzymes. The ABPs can also be used as molecular probes to investigate deubiquitinating enzymes and the regulation of the ubiquitin system in infection processes or serve as drug lead structures for novel therapeutics.

Figure 1A:
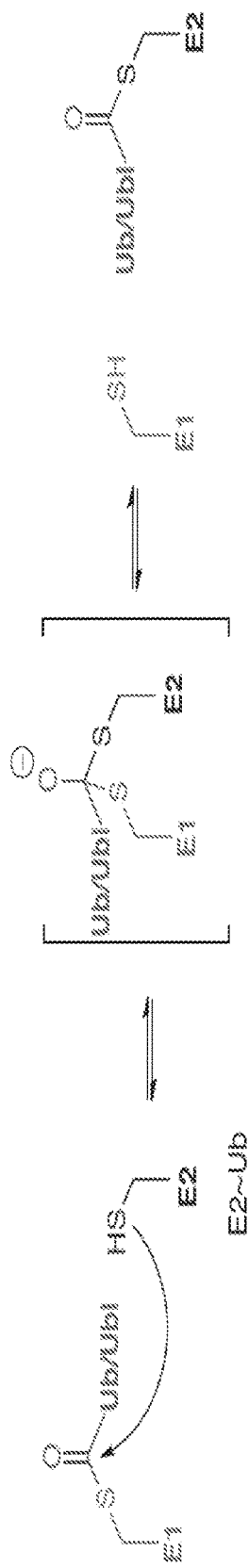
Figure 1B:
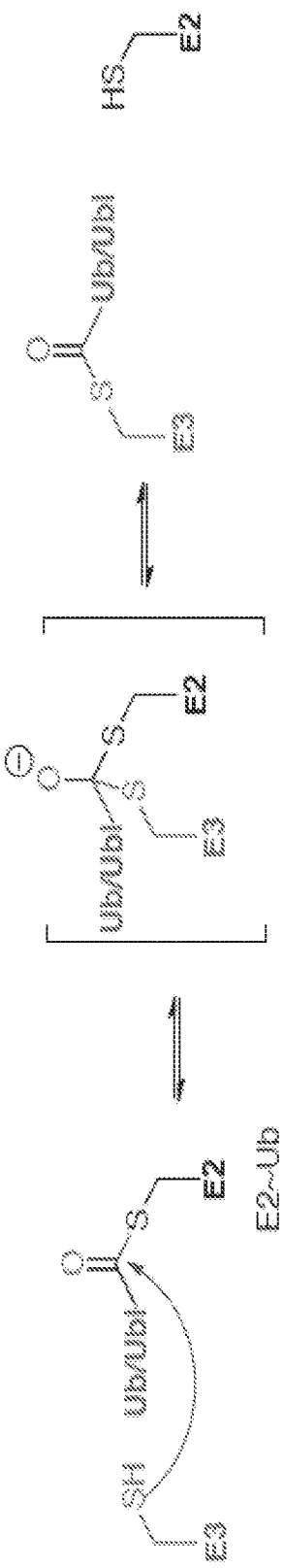
Figure 1C:
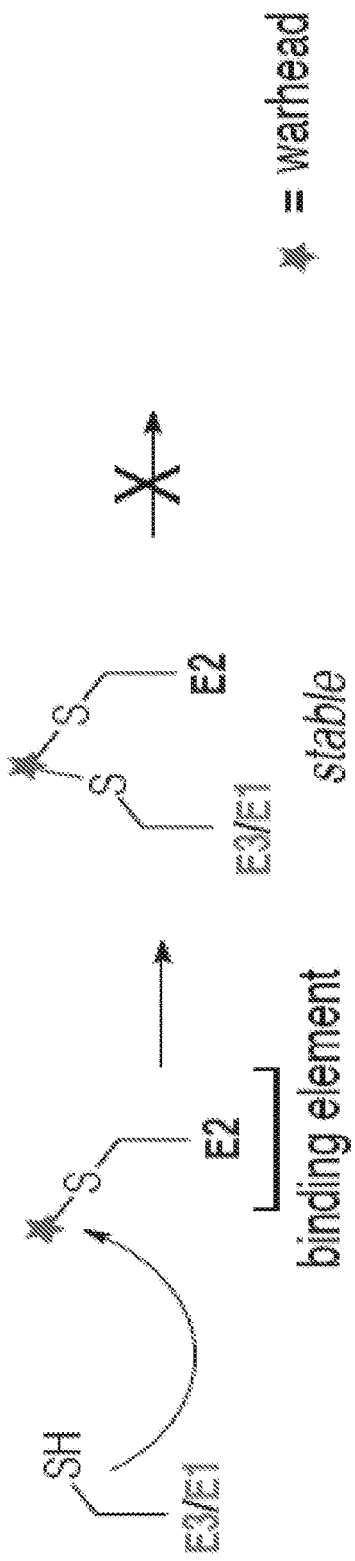
Figure 1D:
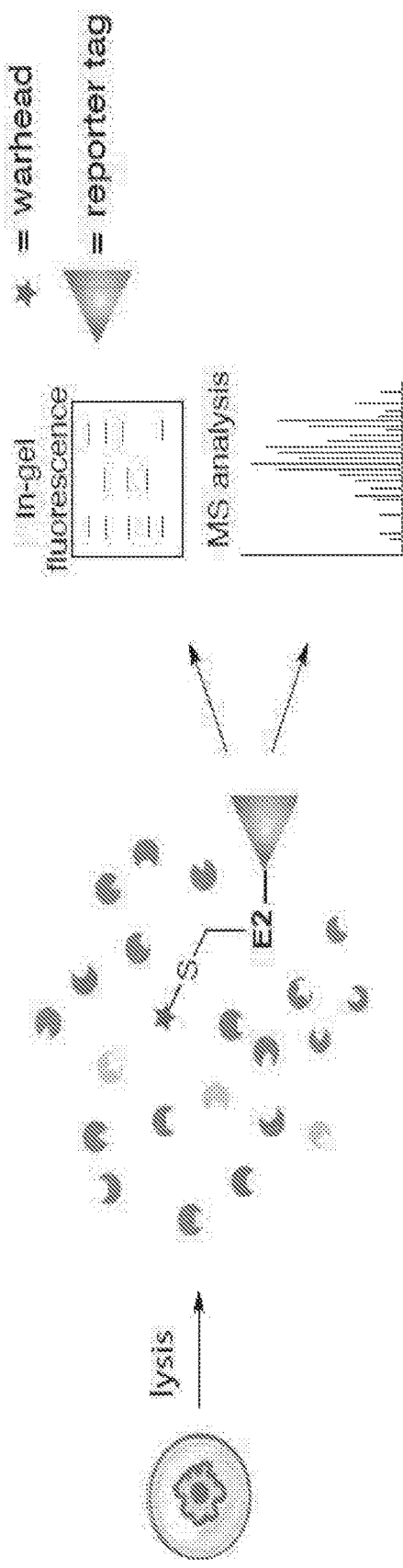

Protein modification with ubiquitin (Ub) and ubiquitin-like modifiers (Ubls) regulates most aspects of eukaryotic biology,[1] and defects within these systems are implicated with a broad spectrum of diseases.[2] Ub/Ubl conjugation is carried out by an enzymatic cascade consisting of E1 activating (E1), E2 conjugating (E2) and E3 ligating (E3) enzymes. Conjugation requires an initial ATP-dependent thioesterification step and up to 2 subsequent transthioesterification steps via the juxtaposition of catalytic cysteines in E1s, E2s and HECT/RBR E3s (FIGS. 1A & B).[3]

Although activity based probes (ABPs) have been developed for numerous enzymes,[4] including E1s,[5] ABPs which profile E1-E2 and E2-E3 transthioesterification activity are not available.

SUMMARY OF THE INVENTION

It is an object of the present invention to provide an activity based probe for use in identifying identification of biological interactions, especially protein/protein interactions. It is a further object of the present invention to provide an activity based probe based on a modified E2 enzyme, for use in identifying E1-E2 and/or E2-E3 interactions.

The present invention is based on studies by the present inventors to develop an activated E2 molecule which could be exploited to study E1-E2 and/or E2-E3 interactions. The present inventors have developed activated E2 molecules which are capable of forming stable covalently bonded conjugates with E1 and/or E3 enzymes through a proximity-accelerated thiol addition reaction between a thioacrylonitrile or methyl thioacrylate group on the activated E2 molecule and a juxtaposed catalytic cysteine residue present on an E1 and/or E3 enzyme. By extension of the technology, other electron deficient vinyl sulphides could be installed.

In related studies, the present inventors have developed conjugate probes, such as E2-ubiquitn conjugate probes, which are also capable of reacting with a cysteine residue of a peptide, such as E3 ubiquitin ligase.

In a first aspect there is provided an activated biological molecule which is capable forming a covalent bond by click reaction when in proximity with a cysteine group of a further biological molecule, wherein the activated biological molecule corresponds to formula (I)

(I)

wherein X is a biological molecule and EWG is an electron withdrawing group.

In a further aspect there is provided a method of preparing an activated biological as defined herein, the method comprising reacting a biological molecule with a compound according to formula (II):

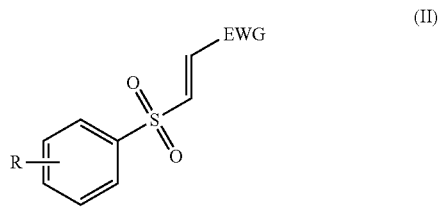
(II)

wherein R is —$C_1$-$C_4$ alkyl, especially methyl, —OH, —$C_1$-$C_4$ alkylhydroxy, —$NH_2$, or —$C_1$-$C_4$ alkylamino, in order to prepare an activated biological molecule in accordance with the first aspect of the present invention.

Preferably the R substituent is present in the para position of the ring.

Preferably the compound according to formula (II) is:

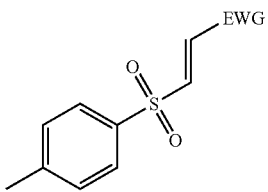

In a further aspect there is a method of detecting an interaction between biological molecules, the method comprising providing a first activated biological molecule according to formula (I)

wherein X is a biological molecule and EWG is an electron withdrawing group; and bringing the activated biological molecule into proximity with one or more biological molecules, in order to allow one or more of said biological molecules to react with the activated biological molecule and form a conjugate; and detecting formation of one or more conjugates which may be formed.

Preferably a sulphur containing moiety of the biological molecule is derivatised in order to form the activated biological molecule. Typically the biological molecule may be a protein or peptide and the sulphur containing moiety is a cysteine, especially an internal cysteine present within the protein or peptide. The cysteine may be a naturally occurring cysteine in the biological molecule, or may be introduced into the molecule In a preferred embodiment the biological molecule is a ubiquitin conjugating enzyme (E2). Preferably one or more catalytically active cysteine residues is/are derivatised.

The E2 enzyme may be selected from UBE2D1, UBE2D1 C86, UBE2D1 C86 AzF3(X), UBE2D2, UBE2D3, UBE2L3*, UBE2L3**, UBE2L6*, UBE2L6**, UBE2N, UBE2H, UBE2I and UBE2M, as identified herein.

The electron withdrawing group (EWG) may be any suitable EWG known to the skilled addressee. Examples of suitable EWGs include —NO$_2$, —NR$_3^+$, —CF$_3$, or other trihalide, —CN, —SOOR, —SOON, —COOH, —COOR, —CHO, —COR, wherein R is typically H, NH, or C1-C4 alkyl (e.g. methyl) or alkenyl. In a preferred embodiment EWG is —CN, or —CO$_2$Me. In one embodiment the EWG is not further substituted. In another embodiment the EWG may be further substituted in order to, for example, provide a functional group which is capable of reacting with a moiety of another molecule and forming a covalent bond.

For example, the EWG group may be substituted with a molecule comprising an alyknyl group. Such an alkynyl group may react by a click chemistry type cycloaddition reaction with an azide moiety to form a 1,2,3-triazole.

In accordance with this embodiment of the invention there may be provided an activated biological molecule conjugate probe, wherein the activated biological molecule conjugate probe corresponds to formula (IV):

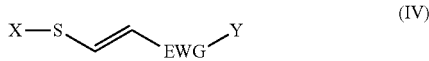

wherein X is a first biological molecule, EWG is an electron withdrawing group and Y is a further biological molecule.

In one embodiment the EWG is bound to the biological molecule Y by way of a triazole group. In accordance with this embodiment, conjugate (IV), more specifically conforms to conjugate (V) below:

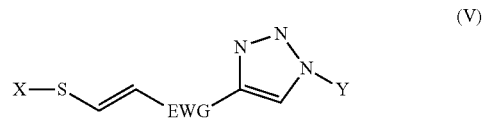

Such a conjugate may be formed in accordance with the following reaction:

The first biological molecule X may be an enzyme and the further biological molecule Y may, for example, be a substrate or ligand for the enzyme. For example, the enzyme may be an E2 ubiquitin conjugating enzyme and the substrate is ubiquitin.

A molecule in accordance with formula (IV) may serve as a probe for detection of a further biological molecule. For example, when the molecule is an E2-ubiquitin molecule, it may serve as a probe for the detection of E3 ubiquitin ligase.

Thus, in a further aspect there is a method of detecting an interaction between biological molecules, the method comprising providing a first activated biological molecule conjugate probe according to formula (IV)

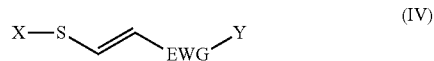

wherein X is a biological molecule, EWG is an electron withdrawing group and Y is a further biological molecule; and bringing the activated biological molecule conjugate probe into proximity with one or more biological molecules, in order to allow one or more of said biological molecules to react with the activated biological molecule conjugate probe and form one or more further conjugate(s); and detecting formation of said one or more further conjugate(s) which may be formed.

In one embodiment, X is E2 ubiquitin conjugating enzyme, Y is ubiquitin and the biological molecule to which the probe binds is E3 ubiquitin ligase.

The activated biological molecules of the present invention may be further modified by incorporation of a tag. The term "Tag" as used herein denotes a biochemical marker or label, i.e. an easily recognizable chemical moiety, e.g. a protein, peptide, or small molecule, that is covalently attached to the activated biological molecule's N-, or C-terminus, preferably the N-terminus. Numerous tags are known to the skilled addressee and include affinity labels, e.g. affinity tags (Kimple and Sondek, BioTechniques (2002), 33:578-590), fluorophores (such as TAMRA, DAPI, fluorescein, Cy3, Cy5, SYBR green and the like), biotin, or radioactive labels.

The activated E2 enzymes and probes of the present invention may allow identification and characterization of new E1-E2 and/or E2-E3 interactions and/or the identification and characterization of previously unknown substrate specificities/mode of action of known E1-E2 and/or E2-E3 pairs Detection of E1-E2 and/or E2-E3 interactions may be carried out using magnetic separation, immunological separation, gel filtration chromatography, affinity chromatography, column chromatography, displacement chromatography, electro chromatography, gas chromatography, high performance liquid chromatography, ion chromatography, micellar electrokinetic chromatography, normal phase chromatography, paper chromatography, reversed-phase chromatography, size exclusion chromatography, thin layer chromatography, gel electrophoresis, centrifugation, adhesion, flow cytometry, or other techniques known to the skilled addressee.

The activated biological molecules, such as activated E2 enzymes, according to the present invention may be used as a research tool, e.g. as a molecular probe to investigate transthioesterification reactions between relevant proteins, such as E1-E2 and/or E2-E3 enzymes and the regulation of the ubiquitin system in biological processes. Alternatively, the present invention may find more application in proximity-based cross linking for mapping protein-protein interaction in general. For example, if one knows where a ligand binds on another protein, the present invention could be used to determine information about the binding mode of the ligand. This would be carried out by inserting cysteine residues throughout the ligand binding site and also throughout the ligand. A cysteine in either ligand or protein is then labelled with an activated vinylsulphide as described herein and the various permutations are mixed with one another. As cross-linking is proximity-based, covalent linkage should only occur when the 2 cysteines are next to one another in yet another embodiment, the invention provides a method of identifying a subset of a proteome, wherein members of the subset share a functional pathway, the method comprising: providing an activated biological molecule in accordance with the present invention; contacting a cell lysate with the activated biological molecule; and analyzing the lysate in order to detect any conjugates formed between the activated biological molecule and a biological molecule present in the cell lysate.

The detection may be carried out, for example by reducing SDS gel electrophoresis and immunoblotting with an antibody specific for the activated biological molecule or tag bound thereto. Alternatively detection may be carried out by performing mass spectrometry.

In a further aspect there is provided a kit comprising a compound according to formula (I), (II), (IV), or (V) as defined herein together with one or more other reagents for use in accordance with the present invention.

DETAILED DESCRIPTION

The present invention will now be further described by way of non-limiting example and with reference to the figures which show—

FIG. 1 shows in schematic form: A) Transthioesterification mechanism between E1 and E2. (B) Transthioesterification between E3s and E2s occurs through juxtaposition of cysteine residues resulting in transfer of Ub/Ubl to E3. (C) E2s labelled with warheads with electrophilic centres immediately proximal to the catalytic cysteine sulphur atom could undergo mechanistic labelling of E1 and E3 enzymes. (D) Reporter tags appended to labelled E2s would serve as probes enabling Activity-Based Protein Profiling (ABPP) strategies.

Figure 2C:
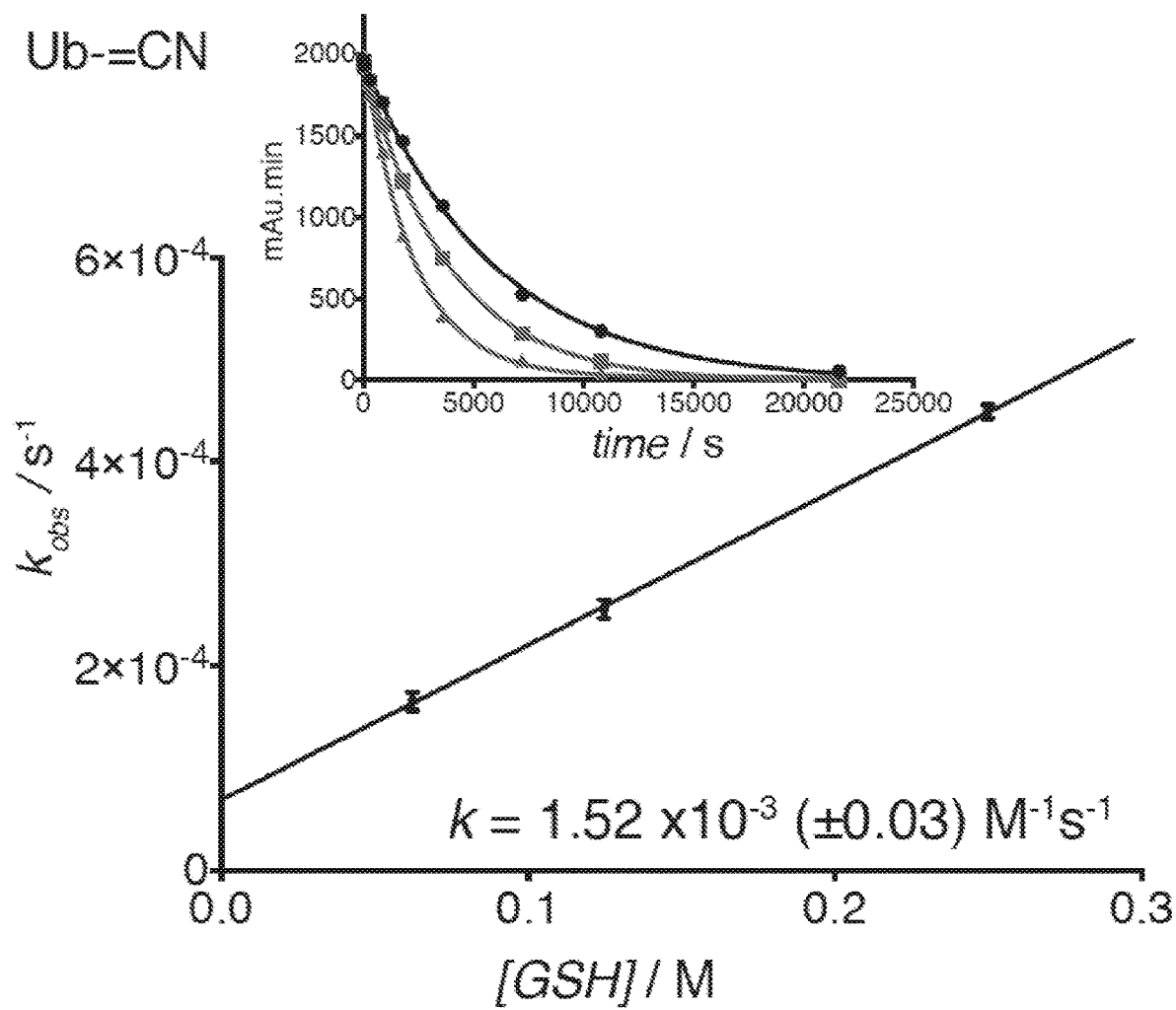
Figure 2D:
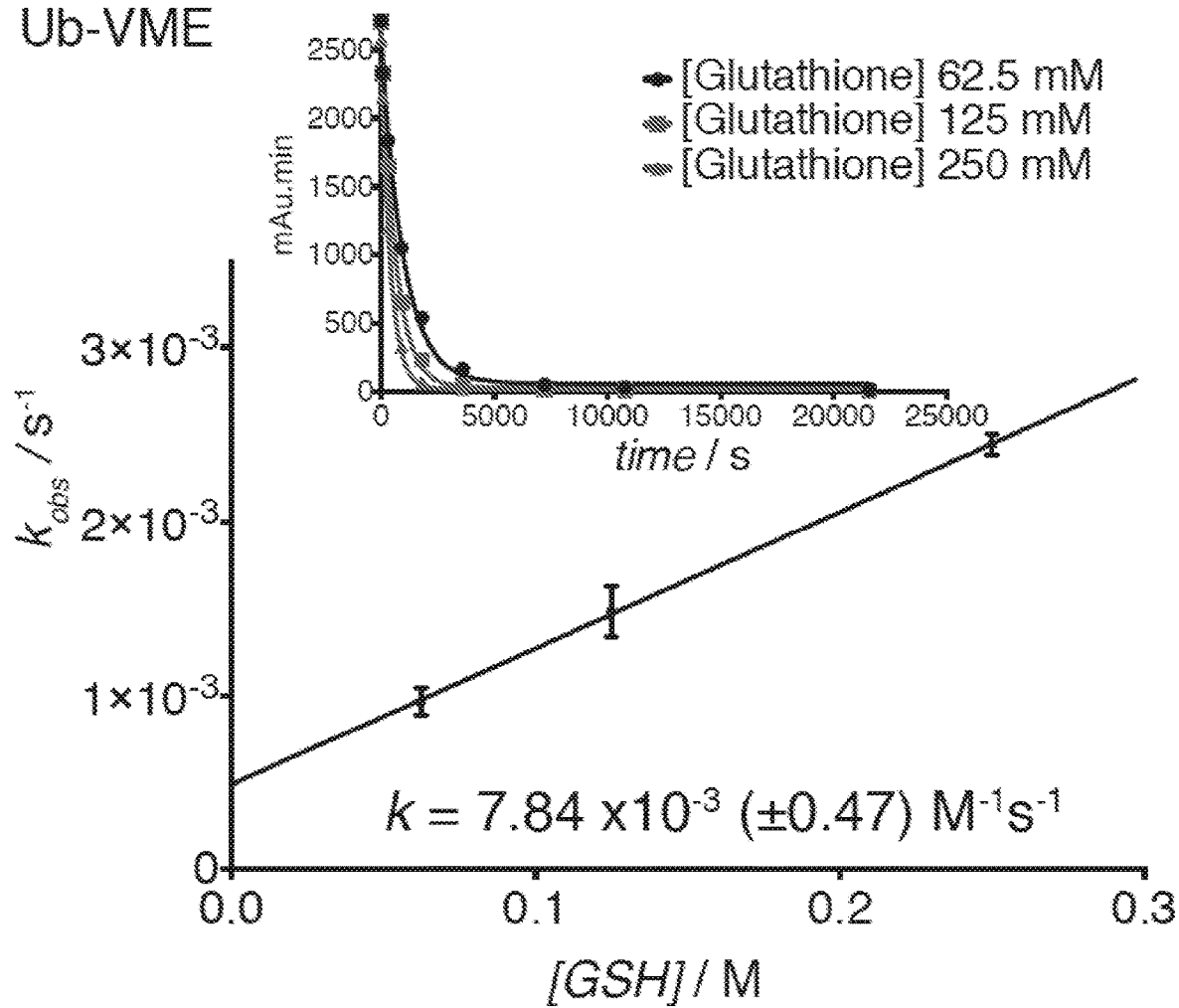
Figure 3A:
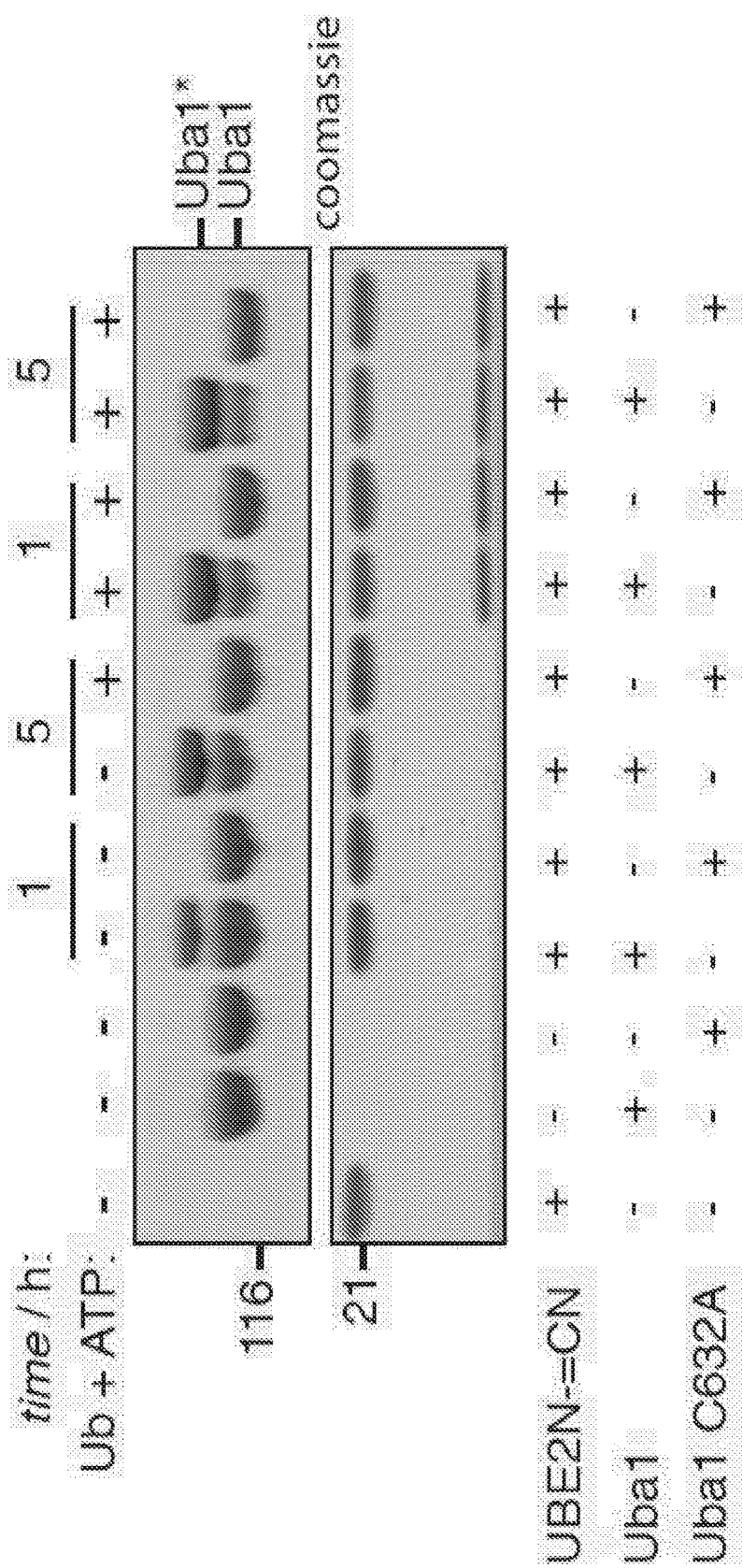
Figure 3B:
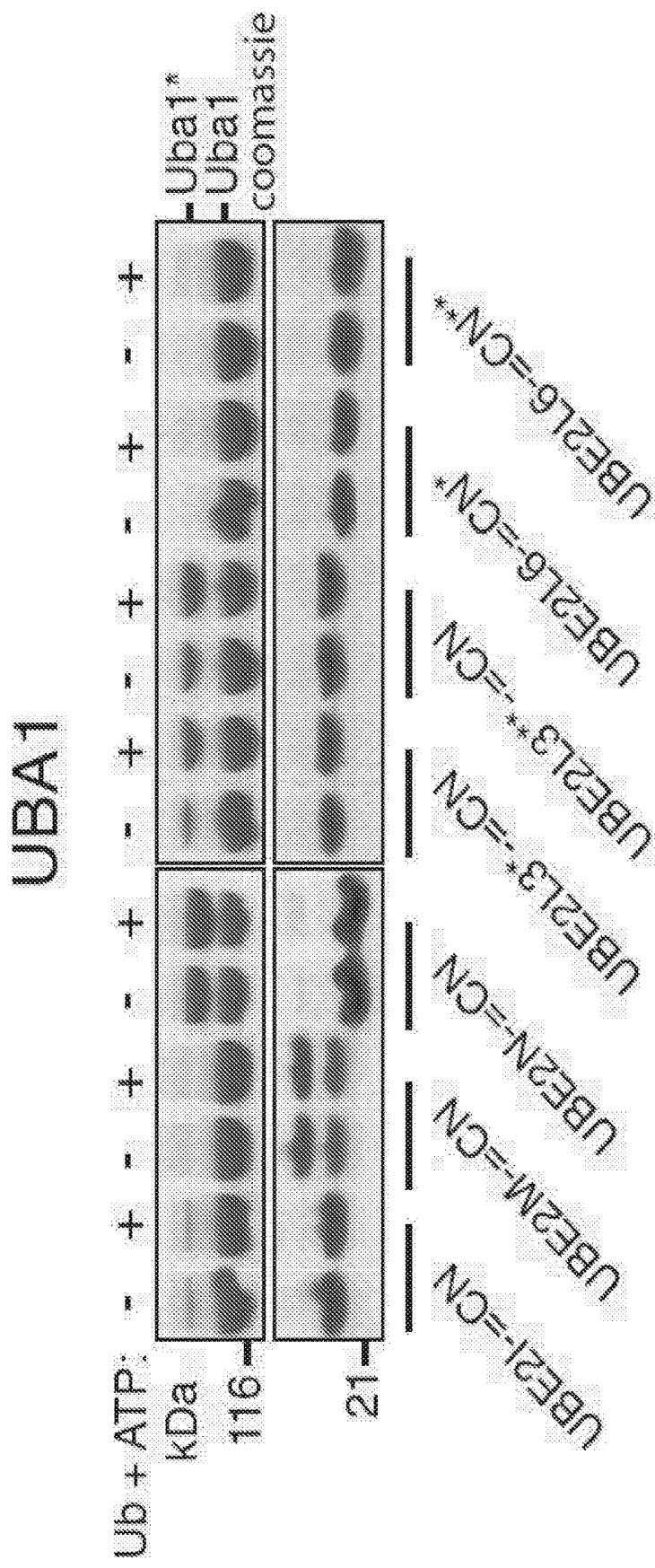
Figure 3C:
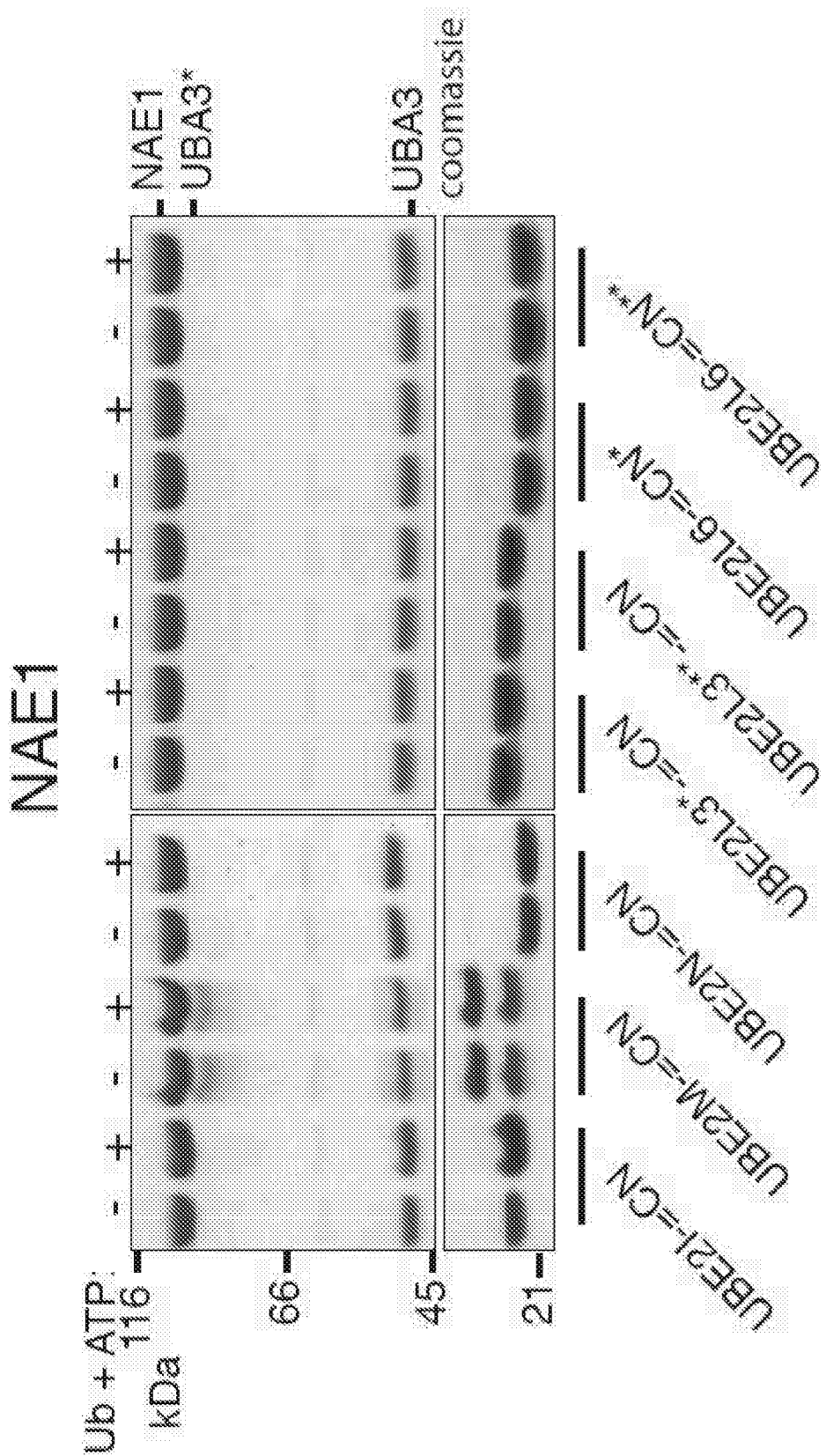
Figure 3D:
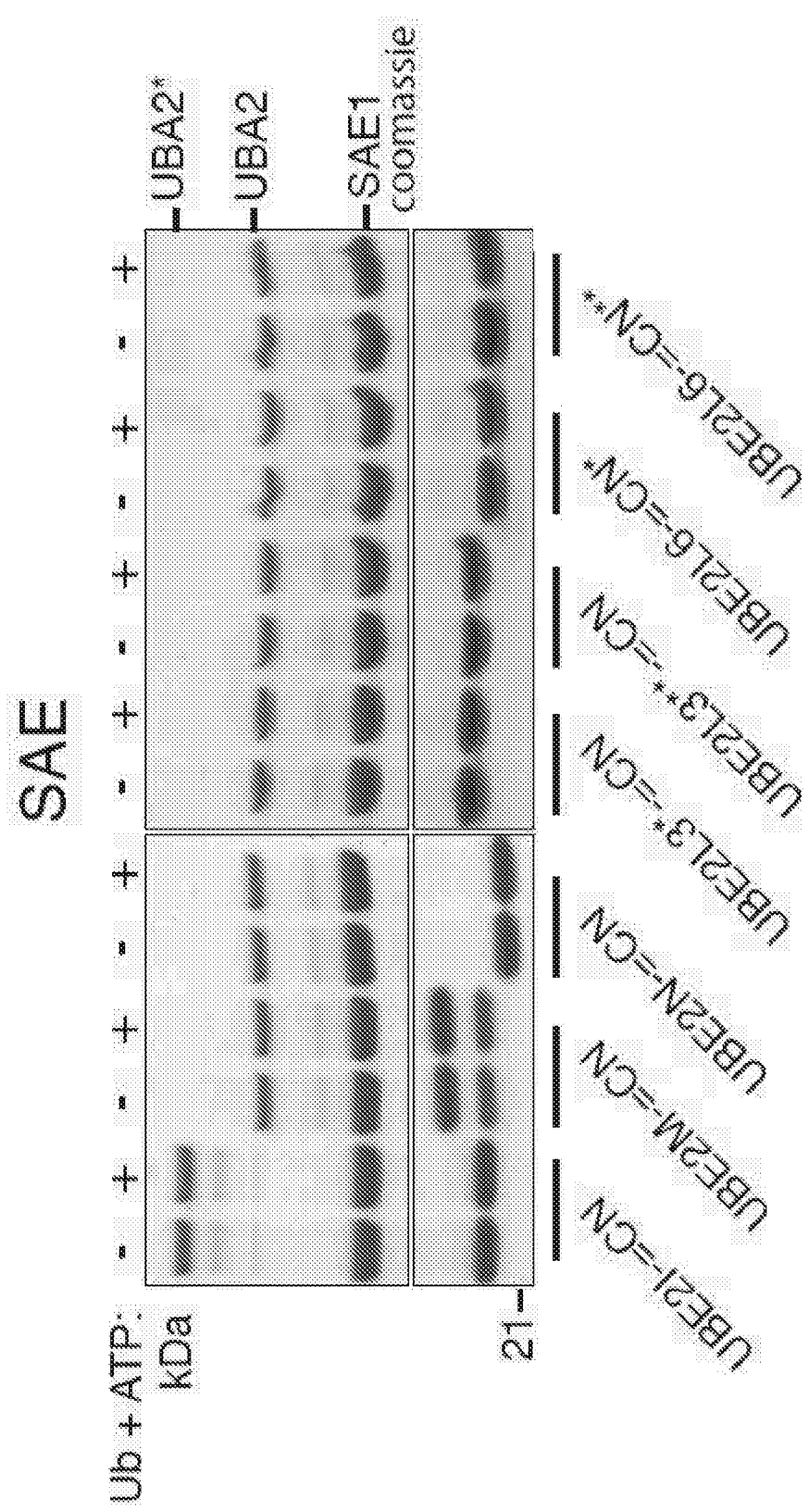

FIG. 2 shows: (A) Formation of a trans activated vinyl-sulfide can occur by chemoselective thiol addition to a TDMA accompanied by elimination of the arylsulfinic acid. Orthogonal functionalization yielding a hetero-bisthiother can commence. (B) UbS-=CN and UbS-VME can undergo sequential addition with the model thiol GSH. (FIG. 2C and FIG. 2D) Second order rate constants under pseudo first order conditions were determined for GSH addition to UbS-=CN (FIG. 2C) and UbS-VME (FIG. 2D).

FIG. 3 shows: A) Time dependant labelling of UBA1 with UBE2N-=CN is dependent on C632. Labelling efficiency is enhanced in the presence of Ub and ATP. (B) UBE2N-=CN and UBE2L3*/**-=CN undergo significant activity-based labelling of UBA1. (C) UBE2M-=CN undergoes significant activity-based labelling of NAE (double band due to degradation of UBE2M). (D) UBE2I undergoes significant activity-based labelling of SAE. (E) UBE2L6*/**-=CN undergoes significant activity-based labelling of UBA7. (F) The top panel depicts ATP-dependant thioesterification activity of UBA1 using fluorescein-labelled Ub as substrate. The bottom panel depicts probe-labelling efficiency.

Figure 4:
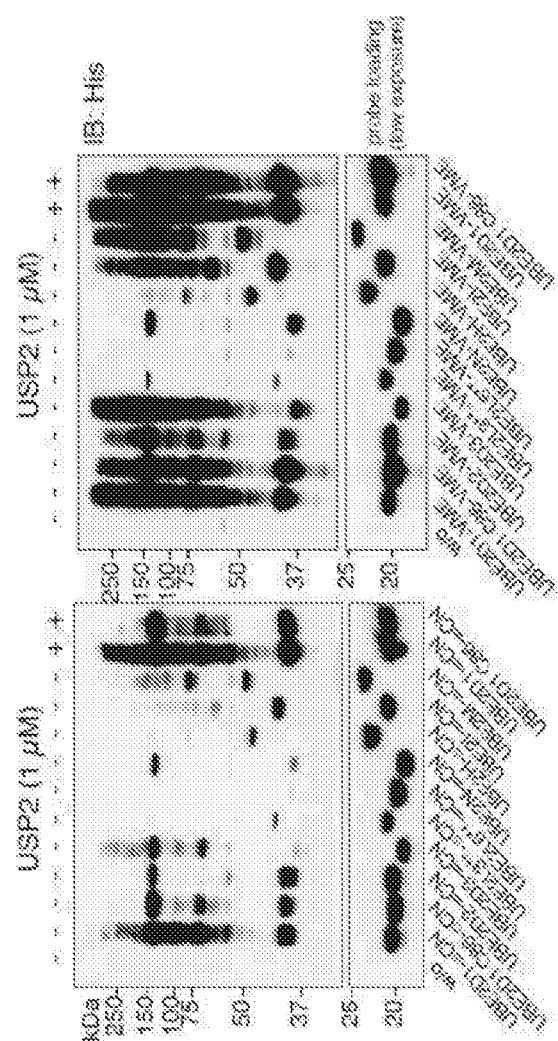

FIG. 4 shows E2 probes (5-25 μM) were incubated with HEK293 proteome (125 μg). Choice of E2 binding element has a striking effect on labelling efficiency. The thiomethyl acrylate warheads exhibit broader labelling (Blots were transferred and processed in parallel).

Figure 5:
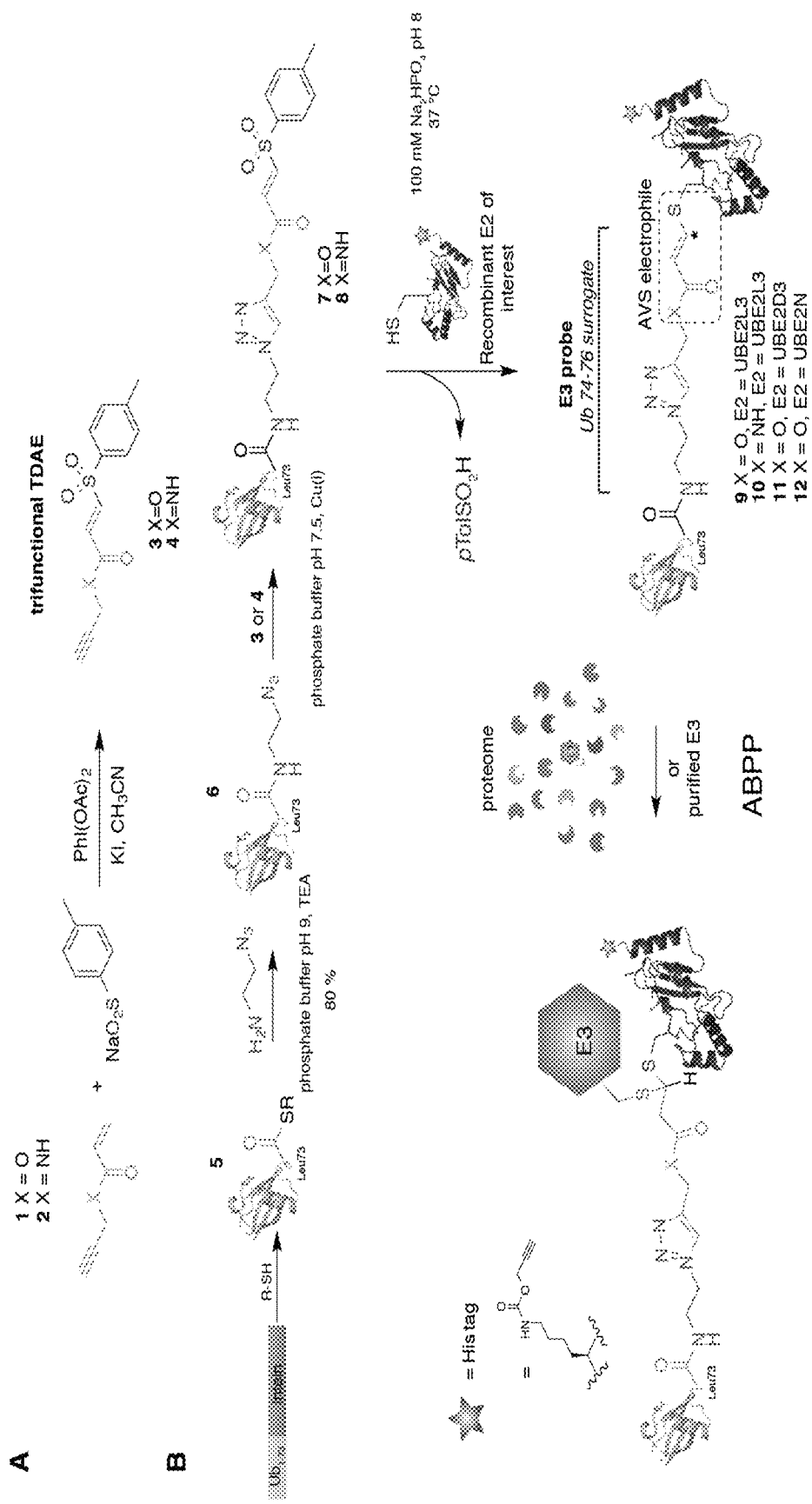

FIG. 5. Synthesis of alkyne-functionalized TDAEs and their utility for assembling E2-Ub-based probes for profiling E3 ligase activity. (a) Alkyne functionalized, electron deficient acrylate 1 and acrylamide 2 were used to prepare trifunctional TDAEs 3 and 4, respectively. This was achieved by PhI(OAc) 2/KI-Mediated reaction of 1 and 2 with sodium arenesulfinate. (b) Probe construction involved production of Ub truncated to residues 1-73 bearing a C-terminal thioester (Ub1-73-SR). This was achieved by thiolysis of an intein fusion protein. Aminolysis of the Ub1-73-SR with azidoaminoethane afforded azide-functionalized Ub (Ub1-73-N 3). Copper-catalyzed Azide-Alkyne Cycloaddition (CuAAC) between Ub1-73-N 3 and TDAEs 3 and 4 yielded TDAE-functionalized Ub molecules (Ub-TDAEs) 7 and 8. Mild incubation with recombinant reporter tagged E2 generated E2-Ub conjugates bearing thioacrylate and thioacrylamide electrophiles poised for activity-based labelling of catalytic cysteine nucleophiles in E3 ligases. Reporter tags were either Hisx6 epitopes or 5-carboxytetramethylrhodamine (TAMRA).

FIG. 6. Characterization data for the preparation of probes 9, 10 and 11. (a) Left panel, Ub thioester 5 (blue) underwent near quantitative aminolysis with azidoaminoethane (green), in aqueous DMSO buffer containing 4% triethylamine, after 16 h incubation at 30° C. The peak denoted with an asterisk corresponds to hydrolysis product of 5. Reaction was monitored by HPLC at 214 nm. Right panel, ESI-MS mass spectrum for starting thioester 5. Inset, deconvoluted mass spectrum (observed mass=8417 Da; calculated mass=8418.7 Da). (b) Left panel, analytical HPLC analysis of purified aminolysis product 6. Right panel, ESI-MS mass spectrum of 6. Inset, deconvoluted mass spectrum (observed mass=8,361 Da; calculated mass=8362.6 Da). (c) HPLC analysis of the purified Ub-TDAE conjugate 7 obtained by Copper-catalyzed Azide-Alkyne Cycloaddition (CuAAC) between azide-functionalized Ub 6 and TDAE 3 in pH 7.5 phosphate buffer, CuSO 4 and Tris(3-hydroxypropyltriazolylmethyl) amine (THPTA) for 15 min incubation at 23° C. Right panel, ESI-MS mass spectrum of 7. Inset, deconvoluted mass spectrum (observed mass=8625 Da; calculated mass=8626.9 Da). (d) Efficient addition-elimination reaction between 7 (lane 2) E2 (His-UBE2L3*) (lane 3) to produce E2-Ub conjugate probe 9 (lane 4). 7 (2 eq.) was added to His-UBE2L3* in phosphate buffered saline and incubated for 2 h at 23° C.). Probe 9 was then purified by size exclusion chromatography (lane 5). (e) Left panel, HPLC analysis of purified probe 9. Right panel, ESI-MS spectrum of 9 (observed mass=26593 Da; calculated mass=6598.5 Da). The N-terminal Hisx6 tag has been proteolytically cleaved for clarity. (f) SDS-PAGE analysis of fluorescent TAMRA-conjugated probe 11. Left lane is a coomassie stain and the right lane is a scan of in-gel fluorescence using an imaging system (excitation λ=532 nm).

FIG. 7. E2-Ub-based probes label the RBR E3 ligase Parkin in an activity-dependantmanner and do not cross react with deubiquitinating enzymes. (a) Coomassie stained reducing SDS-PAGE and anti-His immunoblotting reveals that 9 and 10 (10 µM) form a covalent adduct with p-Parkin (2 µM) in the presence of p-Ub (2 µM) (lanes 2 and 3). Probe 9 F63A (predicted to abolish E3 binding) failed to label Parkin under the same conditions (lane 4). Non-phosphorylated Parkin failed to undergo labelling with probe 9 in the presence of p-Ub (2 µM) (lane 5). Labelling could be effected by the inclusion of elevated levels of p-Ub (lanes 6 and 7). (b) Probe 10 does not label p-Parkin C431S in the presence of p-Ub (lane 8 last lane) vs. lane 5). All Parkin species and p-Ub were pre-phosphorylated by treatment with PhPINK1. (c) Annotated tryptic MS/MS spectrum for a tryptic 5+ charged precursor ion of the crosslinked peptide derived from labeling of Parkin with 9 (observed m/z=625.7106; expected m/z=625.7126) further confirms probe labeling of Parkin C431. (d) In situ probe labelling of reconstituted substrate ubiquitination assays. Parkin and FLAG-Ub in the reactions were phosphorylated by pre-incubation with TcPINK1. Parkin labelling with fluorescent probe 11 and probe 9 was strictly consistent with the Parkin activity readouts of His-SUMO-Miro1 substrate ubiquitination, Parkin autoubiquitination, and free polyubiquitin chain formation. In all cases, activity was strictly dependent on TcPINK1 activity.

Figure 8:
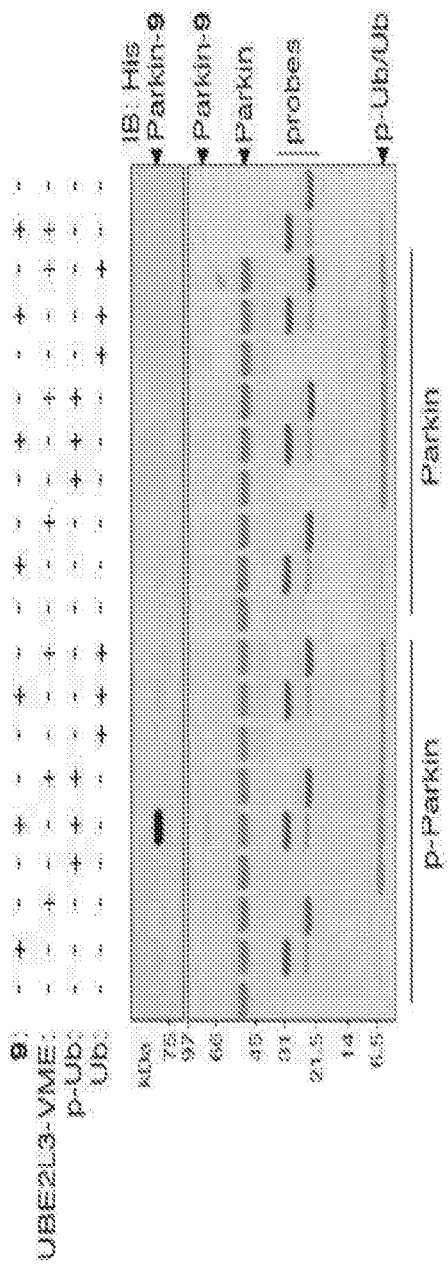

FIG. 8. Optimal Parkin transthiolation activity requires phosphorylation of p-Parkin and p-Ub and the Ub component in E2-Ub is required for cysteine-cysteine juxtaposition. Pre-phosphorylated p-Parkin (3 µM) only underwent probe labelling in the presence of p-Ub (2 µM) (lane 5). No labeling was observed in the presence of Ub illustrating the significant of both phosphorylation events for optimal Parkin transthiolation activity. The first-generation E2-based probe UBE2L3*-VME, that bears a chemically analogous electrophile to 9 but lacks the Ub component, failed to label Parkin under any of the conditions tested.

FIG. 9. Quantitative and direct activity-based Protein Profiling of transthiolation activity of Parkin patient mutations reveals distinct activity signature. (a) Amino acid boundaries of the multi-domain architcture of Parkin. (b) Recombinant Parkin mutants were incubated with PhPINK1 in presence of Ub and ATP. Mutations resided throughout the multi-domain architecture of Parkin. Incubations were then directly profiled for Parkin transthiolation activity with fluorescent probe 11 Mutations mildy compromised (0.7- fold), activated (1.3-1.6-fold) or abolished transthiolation activity as determined by fluorescence of labeled Parkin.

Figure 10A:
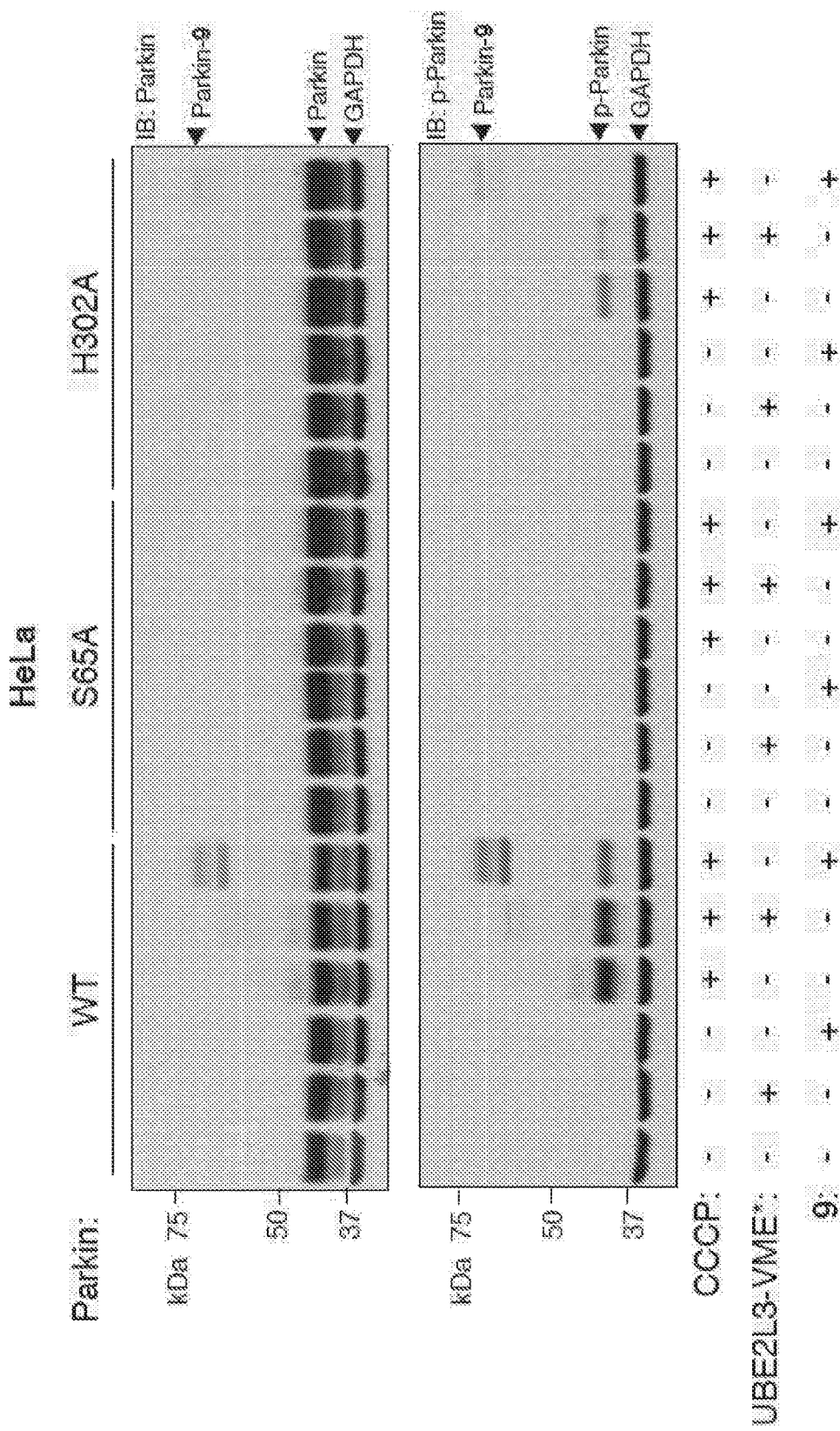

FIG. 10. Activity-based profiling of cellular Parkin provides insights into the hierachy of Parkin and Ub phosphorylation in the context of PINK1-Parkin signalling, and reveals, quantifiable, protonophore responsive activation of endogenous Parkin in SH-SY5Y dopaminergic cells. (a) HeLa cells stably expressing Parkin WT, Parkin S65A and Parkin H302A were untreated or treated with the CCCP (10 µM) for 3 h to promote mitochondrial depolarization. Extracts were then obtained by mild lysis and were profiled in parallel with probe 9 and UBE2L3*-VME (5 µM). Robust labelling of Parkin WT was only observed with probe 9 in response to CCCP treatment. Probe labeling correlated with Parkin phosphorylation and labeling of the phosphorylated pool was more efficient than that of the total Parkin pool, as determined by anti-Parkin and anti-Parkin-pSer65 immunoblotting. Non-phosphorylatable Parkin S65A did not undergo labeling with probe 9 emphasizing a strict requirement of Parkin phosphorylation for activity. Parkin H302A with significantly impaired p-Ub binding ability exhibited compromised labeling efficiency with 9. Parkin phosphorylation was also significantly compromised. This suggests that in the context of PINK1-Parkin cellular signaling, initial generation of p-Ub binds Parkin and primes it for phosphorylation by PINK1 that leads to its optimal activation. Consistent results were obtained over 3 replicate experiments. (b) Activity-based profiling of endogenous Parkin directly reveals Parkin phosphorylation and activation of transthiolation in response to CCCP treatment. Labelling of the total Parkin pool is more efficient than with overexpressed Parkin. Labelling efficiency of the p-Parkin pool approached 100%. Labeling was not observed with the control probes UBE2L3*-VME or 9 F63A. Over the time course, probe labeling efficiency of Parkin remains unchanged whilst Parkin levels reduce suggestive of Parkin clearance in the activated state. Asterisk corresponds to a cross-reactive band. Consistent results were obtained over 3 replicate experiments.

Figure 11:
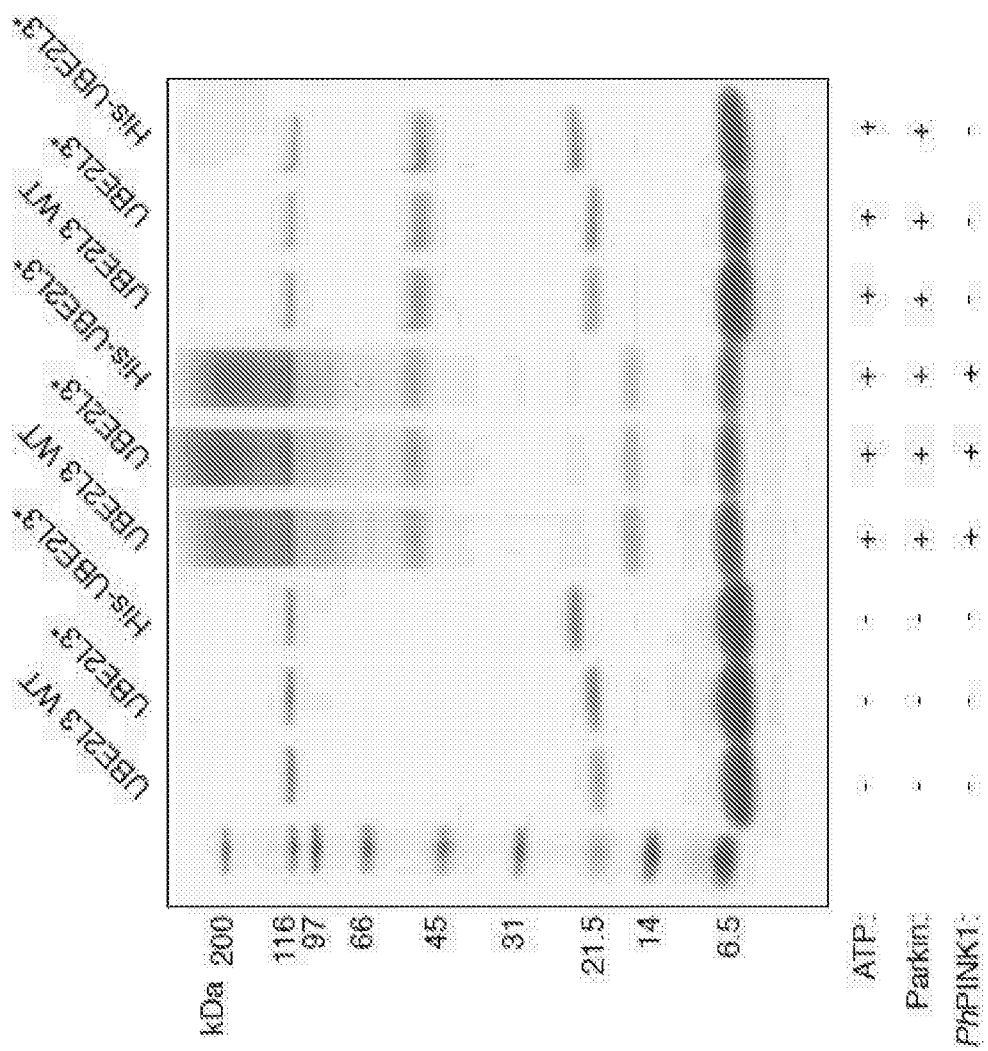

FIG. 11. Tagged and untagged forms of double mutant C17S C137S UBE2L3 (UBE2L3*) support Parkin activity. The His-tagged form of UBE2L3* that probes 9, 10 and 11 were based on was tested for its ability to support Parkin activity. Both His-UBE2L3* and UBE2L3* (where the N-terminal Hisx6 tag was removed with Rhinovirus C3 protease) demonstrated activity comparable to wt protein in a qualitative SDS-PAGE gel-based activity assay. Unless otherwise labeled, 50 µL reactions consisted of 50 mM Tris-HCl pH7.5, $MgCl_2$ (5 mM), ATP (2 mM), UBA1 (240 nM), UBE2L3 variant (2 µM), Ub (25 µg), Parkin (3 µg), GST-PhPINK1 (1.5 µg). Reactions were incubated at 30° C. for 1 h, resolved by SDS-PAGE, and visualized by coomassie staining.

Figure 12:
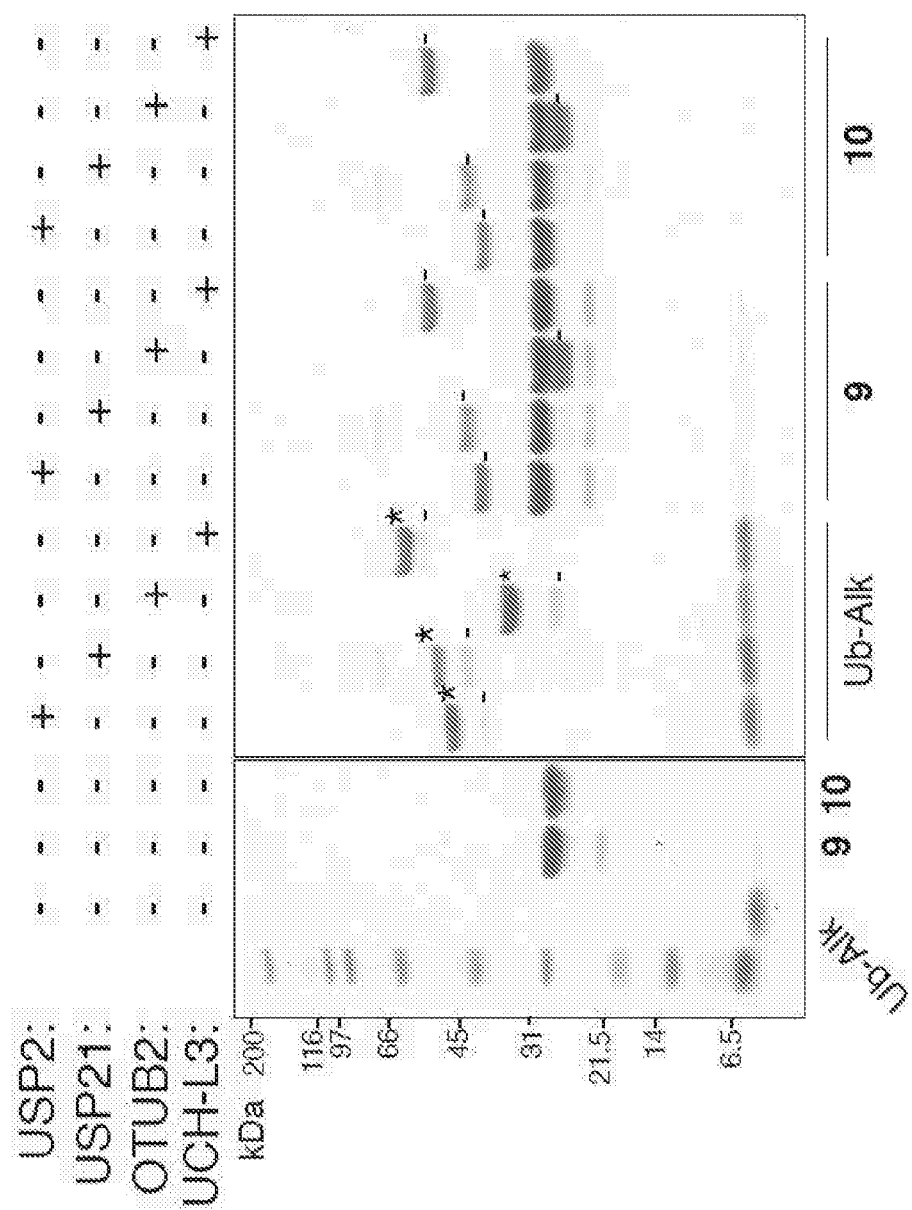

FIG. 12. Probes 9 and 10 do not label the USP family DUBs USP2 and USP21, the OTU family DUB OTUB2, or the UCH family DUB UCH-L3 (- corresponds to unlabeled DUB). No hydrolysis of the probes was observed either. In contrast, the DUB probe Ub-Alk efficiently labeled all DUBs confirming DUB activity (* corresponds to DUBs labeled with Ub-Alk).

MATERIALS & METHODS

General Methods

LC-MS was carried out with an Agilent 1200 LC-MS system fitted with a Max-Light Cartridge flow cell coupled to a 6130 Quadrupole spectrometer. The solvent system consisted of 0.05% trifluoroacetic acid (TFA) in H2O as buffer A, and 0.04% TFA acid in acetonitrile (MeCN) as buffer B. Protein UV absorbance was monitored at 214 and 280 nm. An Agilent ZORBAX 300SB-C3 5 um, 2.1×150 mm column was employed for proteins unless otherwise stated. Protein MS acquisition was carried out in positive ion mode and total protein masses were calculated by deconvolution within the MS Chemstation software (Agilent Technologies).

Small molecule LC-MS was carried out using the Agilent system with an Agilent ZORBAX Eclipse Plus C18, 4.6× 100 mm, 3.5 μm column. Variable wavelengths were used and MS acquisitions were carried out in positive and negative ion modes.

Semi-preparative peptide HPLC was carried out on a Dionex Ultimate system with Thermo Biobasic C4 21.2× 250 mm column at a flow rate of 10 ml min-1.

1H & 13C NMR was carried out with a (Bruker AVANCE II 500 spectrometer). Chemical shifts (δ) are reported in ppm and referenced to residual solvent (MeOH-D4). J values are in hertz, and the splitting patterns are designated as follows: s, singlet; bs, broad singlet; d, doublet; t, triplet; app. t, apparent triplet; q, quartet; m, multiplet. All solvents and reagents were purchased from Sigma Aldrich or VWR unless otherwise stated.

```
> UBE2D1
MGSSHHHHHHSSGLVPRGSHMASMTGGQQMGRGSALKRIQKELSDLQRDPPAHCS

AGPVGDDLFHWQATIMGPPDSAYQGGVFFLTVHFPTDYPFKPPKIAFTTKIYHPNINS

NGSICLDILRSQWSPALTVSKVLLSICSLLCDPNPDDPLVPDIAQIYKSDKEKYNRHARE

WTQKYAM (SEQ ID NO: 1)

Features (amino acid residue numbers):

6His: [5:10]

Thrombin site: [14:19]

> UBE2D1 C86
MSYYHHHHHHDYDIPTTENLYFQGAGSGSMALKRIQKELSDLQRDPPAHSSAGPVG

DDLFHWQATIMGPPDSAYQGGVFFLTVHFPTDYPFKPPKIAFTTKIYHPNINSNGSICL

DILRSQWSPALTVSKVLLSISSLLSDPNPDDPLVPDIAQIYKSDKEKYNRHAREWTQKY

AM (SEQ ID NO: 2)

Features (amino acid residue numbers):

6His: [5:10]

TEV site: [18:24]

> UBE2D1 C86 AzF3(X)
MSXYHHHHHHDYDIPTTENLYFQGAGSGSMALKRIQKELSDLQRDPPAHSSAGPVG

DDLFHWQATIMGPPDSAYQGGVFFLTVHFPTDYPFKPPKIAFTTKIYHPNINSNGSICL

DILRSQWSPALTVSKVLLSISSLLSDPNPDDPLVPDIAQIYKSDKEKYNRHAREWTQKY

AM (SEQ ID NO: 3)

Features (amino acid residue numbers):

6His: [5:10]

TEV site: [18:24]

> UBE2D2
MGSSHHHHHHSSGLVPRGSHMASMTGGQQMGRGSALKRIHKELNDLARDPPAQCS

AGPVGDDMFHWQATIMGPNDSPYQGGVFFLTIHFPTDYPFKPPKVAFTTRIYHPNINS

NGSICLDILRSQWSPALTISKVLLSICSLLCDPNPDDPLVPEIARIYKTDREKYNRIAREW

TQKYAM (SEQ ID NO: 4)

Features (amino acid residue numbers):

6His: [5:10]

Thrombin site: [14:19]

> UBE2D3
MGSSHHHHHHSSGLEVLFQGPGSALKRINKELSDLARDPPAQCSAGPVGDDMFHW

QATIMGPNDSPYQGGVFFLTIHFPTDYPFKPPKVAFTTRIYHPNINSNGSICLDILRSQ

WSPALTISKVLLSICSLLCDPNPDDPLVPEIARIYKTDRDKYNRISREWTQKYAM
(SEQ ID NO: 5)
```

-continued

Features (amino acid residue numbers):

6His: [5:10]

PreScission site: [14:21]

> UBE2L3*
MGSSHHHHHHSSGLEVLFQGPGSMAASRRLMKELEEIRKSGMKNFRNIQVDEANLLT
WQGLIVPDNPPYDKGAFRIEINFPAEYPFKPPKITFKTKIYHPNIDEKGQVCLPVISAEN
WKPATKTDQVIQSLIALVNDPQPEHPLRADLAEEYSKDRKKFSKNAEEFTKKYGEKRP
VD (SEQ ID NO: 6)

Features (amino acid residue numbers):

6His: [5:10]

PreScission site: [14:21]

> UBE2L3**
MGSSHHHHHHSSGLEVLFQGPGSMAASRRLMKELEEIRKSGMKNFRNIQVDEANLLT
WQGLIVPDNPPYDKGAFRIEINFPAEYPFKPPKITFKTKIYHPNIDEKGQVCLPVIAAEN
WKPATKTDQVIQSLIALVNDPQPEHPLRADLAEEYSKDRKKFSKNAEEFTKKYGEKRP
VD (SEQ ID NO: 7)

Features (amino acid residue numbers):

6His: [5:10]

PreScission site: [14:21]

> UBE2L6*
MGSSHHHHHHSSGLEVLFQGPGSMMASMRVVKELEDLQKKPPPYLRNLSSDDANVL
VWHALLLPDQPPYHLKAFNLRISFPPEYPFKPPMIKFTTKIYHPNVDENGQICLPIISSE
NWKPSTKTSQVLEALNVLVNRPNIREPLRMDLADLLTQNPELFRKNAEEFTLRFGVDR
PS (SEQ ID NO: 8)

Features (amino acid residue numbers):

6His: [5:10]

PreScission site: [14:21]

> UBE2L6**
MGSSHHHHHHSSGLEVLFQGPGSMMASMRVVKELEDLQKKPPPYLRNLSSDDANVL
VWHALLLPDQPPYHLKAFNLRISFPPEYPFKPPMIKFTTKIYHPNVDENGQICLPIIASE
NWKPSTKTSQVLEALNVLVNRPNIREPLRMDLADLLTQNPELFRKNAEEFTLRFGVDR
PS (SEQ ID NO: 9)

Features (amino acid residue numbers):

6His: [5:10]

PreScission site: [14:21]

> UBE2N
MGSSHHHHHHSSGLEVLFQGPGSAGLPRRIIKETQRLLAEPVPGIKAEPDESNARYFH
VVIAGPQDSPFEGGTFKLELFLPEEYPMAAPKVRFMTKIYHPNVDKLGRICLDILKDKW
SPALQIRTVLLSIQALLSAPNPDDPLANDVAEQWKTNEAQAIETARAWTRLYAMNNI
(SEQ ID NO: 10)

Features (amino acid residue numbers):

6His: [5:10]

PreScission site: [14:21]

\> UBE2H
MGSSHHHHHHSSGLEVLFQGPGSMSSPSPGKRRMDTDVVKLIESKHEVTILGGLNEF

VVKFYGPQGTPYEGGVWKVRVDLPDKYPFKSPSIGFMNKIFHPNIDEASGTVCLDVIN

QTWTALYDLTNIFESFLPQLLAYPNPIDPLNGDAAAMYLHRPEEYKQKIKEYIQKYATE

EALKEQEEGTGDSSSESSMSDFSEDEAQDMEL (SEQ ID NO: 11)

Features (amino acid residue numbers):

6His: [5:10]

PreScission site: [14:21]

\> UBE2I
MGSSHHHHHHSSGLEVLFQGPGSMSGIALSRLAQERKAWRKDHPFGFVAVPTKNPD

GTMNLMNWECAIPGKKGTPWEGGLFKLRMLFKDDYPSSPPKCKFEPPLFHPNVYPS

GTVCLSILEEDKDWRPAITIKQILLGIQELLNEPNIQDPAQAEAYTIYCQNRVEYEKRVR

AQAKKFAPS (SEQ ID NO: 12)

Features (amino acid residue numbers):

6His: [5:10]

PreScission site: [14:21]

\> UBE2M
MGSSHHHHHHSSGLEVLFQGPGSPEFPGVDSKAAAMIKLFSLKQQKKEEESAGGTK

GSSKKASAAQLRIQKDINELNLPKTCDISFSDPDDLLNFKLVICPDEGFYKSGKFVFSFK

VGQGYPHDPPKVKCETMVYHPNIDLEGNVCLNILREDWKPVLTINSIIYGLQYLFLEPN

PEDPLNKEAAEVLQNNRRLFEQNVQRSMRGGYIGSTYFERCLK (SEQ ID NO: 13)

Features (amino acid residue numbers):

6His: [5:10]

PreScission site: [14:21]

Experimental Procedures

Preparation of $Ub_{1-74}$ Mercaptoethyl Carboxamide ($Ub_{1-74}$-SH)

Codons for ubiquitin residues 75-76 were deleted by Quikchange mutagenesis using the plasmid pTXB1-Ub1-76 [4] as template yielding plasmid pTXB1-Ub1-74. The 5'-GTCTTAAGACTGCGTTGCATCACGGGAGATG-3' (SEQ ID NO:14) forward primer and 5'-CATCTCCCGT-GATGCAACGCAGTCTTAAGAC-3' (SEQ ID NO:15) reverse primer were used. ER2566 *E. coli*. cells (50 µL) (NEB) were transformed with pTXB1-Ub1-74 and recovered with S.O.B. medium (250 µL). The cells were incubated for 1 h at 37 µC and then LB medium (100 mL) containing ampicillin (100 µg mL-1) was inoculated with the recovered cells (200 µL) and the culture was incubated overnight whilst shaking (230 rpm) at 37 µC. LB medium (2 L) containing ampicillin (100 µg mL-1) was inoculated with the overnight culture (60 mL) and incubated whilst shaking (230 rpm) at 37 µC. At O.D.600~0.4, the cells were transferred to a 25 µC incubator and after 30 min the cells were induced with IPTG (0.5 mM). After 5 h the cells were harvested and suspended in 60 ml lysis buffer (20 mM Na2HPO4 pH 7.2, 200 mM NaCl, 1 mM EDTA) and frozen. The thawed cells were lysed by sonication on ice and were clarified by centrifugation (39000×g, 30 min). An empty XK 26/20 column was filled with chitin beads (20 mL) (NEB) and equilibrated with lysis buffer. At 4 µC the clarified lysate was loaded (flow rate:0.5 mL min-1) onto the column using an ÄKTA FPLC system. The column was then washed with lysis buffer (~400 mL) and equilibrated with 60 mL of cleavage buffer (20 mM Na2HPO4 pH 7.2, 200 mM NaCl, 50 mM cysteamine, 10 mM TCEP, 1 mM EDTA). The flow was then stopped and the column incubated for 66 h at 23µ Preparation of UbS-=CN, UbS-VME and UbS-VME*

$Ub_{1-74}$-SH (3.6 mg, 0.42 µmol) was reconstituted[5] by the addition of DMSO (54 µL). On complete dissolution of $Ub_{1-74}$-SH in DMSO, PBS (1×, 1746 µL) was added to give a final DMSO concentration of 3% (v/v) and a final $Ub_{1-74}$-SH concentration of 233 µM. 4 eq. of 1 were then added from a DMSO stock solution of 1 (17.6 µL, 96 mM) and the mixture was then briefly vortexed. The resulting solution was placed in an Eppendorf thermomixer (30° C., 2 hours) and the reaction was monitored by LC-MS (Figure S2). To remove small molecule by-products, the reaction solution was buffer exchanged into MQ water using a pre-packed PD-10 column (GE Healthcare). UbS-=CN was eluted on the addition at an approximate concentration of 116 µM (based on quantitative conversion of $Ub_{1-74}$-SH.

Determination of UbS-=CN concentration was achieved by extrapolation using a standard concentration curve of WT Ub based upon the absorbance of the UV absorbance at 214 nm (Figure S8). Preparation of UbS-VME and UbS-VME* was carried under identical conditions but 1 was substituted for 2 and methyl propiolate respectively.

Standard Concentration Curve of WT Ub

From a 1.66 mM stock solution of Ubiquitin (determined by using A280 0.16=1 mg/mL) Serial dilution of a 1 mM WT Ub solution (100 mM Na$_2$HPO$_4$, pH 8) was then carried out to generate stock WT Ub solutions at concentrations of 5 µM, 10 µM, 30 µM and 50 µM (100 mM Na$_2$HPO$_4$, pH 8). 100 µL of each solution was added to 4 µL 25% TFA (in acetonitrile). Samples were then analysed by LC-MS (5 µL injection, see General methods; protein LC-MS) with a gradient of 10% to 75% acetonitrile (flow rate; 0.3 mL/min) over 20 minutes. The peak area of Ub at 214 nm was determined using the Agilent Chemstation software v.4.0. Runs were repeated in duplicate.

C, to allow thiolysis and concomitant rearrangement. Liberated Ub$_{1-74}$-SH was eluted with elution buffer (20 mM Na2HPO4 pH 6, 200 mM NaCl, 1 mM EDTA). The fractions containing Ub$_{1-74}$-SH were pooled and concentrated to ~5 mL using an Amicon Ultra-15 centrifugal filter device (Millipore). The protein was then further purified by semi-preparative RP-HPLC using the Dionex system. A gradient of 10% buffer A to 80% buffer B was applied at a flow rate of 10 mL min over 30 min$^{-1}$ (buffer A=0.1% TFA in H$_2$O, buffer B=0.1% TFA in acetonitrile). Fractions containing Ub$_{1-74}$-SH were pooled and lyophilized.

Preparation of UbS-=CN, UbS-VME and UbS-VME*

Ub$_{1-74}$-SH (3.6 mg, 0.42 µmol) was reconstituted[5] by the addition of DMSO (54 µL). On complete dissolution of Ub$_{1-74}$-SH in DMSO, PBS (1×, 1746 µL) was added to give a final DMSO concentration of 3% (v/v) and a final Ub$_{1-74}$-SH concentration of 233 W. 4 eq. of 1 were then added from a DMSO stock solution of 1 (17.6 µL, 96 mM) and the mixture was then briefly vortexed. The resulting solution was placed in an Eppendorf thermomixer (30° C., 2 hours) and the reaction was monitored by LC-MS (Figure S2). To remove small molecule by-products, the reaction solution was buffer exchanged into MQ water using a pre-packed PD-10 column (GE Healthcare). UbS-=CN was eluted on the addition at an approximate concentration of 116 µM (based on quantitative conversion of Ub$_{1-74}$-SH.

Determination of UbS-=CN concentration was achieved by extrapolation using a standard concentration curve of WT Ub based upon the absorbance of the UV absorbance at 214 nm. Preparation of UbS-VME and UbS-VME* was carried under identical conditions but 1 was substituted for 2 and methyl propiolate respectively.

Standard Concentration Curve of WT Ub

From a 1.66 mM stock solution of Ubiquitin (determined by using A280 0.16=1 mg/mL) Serial dilution of a 1 mM WT Ub solution (100 mM Na$_2$HPO$_4$, pH 8) was then carried out to generate stock WT Ub solutions at concentrations of 5 µM, 10 µM, 30 µM and 50 µM (100 mM Na$_2$HPO$_4$, pH 8). 100 µL of each solution was added to 4 µL 25% TFA (in acetonitrile). Samples were then analysed by LC-MS (5 µL injection, see General methods; protein LC-MS) with a gradient of 10% to 75% acetonitrile (flow rate; 0.3 mL/min) over 20 minutes. The peak area of Ub at 214 nm was determined using the Agilent Chemstation software v.4.0. Runs were repeated in duplicate.

Reaction of Glutathione with UbS-=CN and Rate Constant Determination

The rate constant for the reaction of UbS-=CN with reduced glutathione was obtained by manual mixing under pseudo-first order conditions by monitoring the exponential depletion of UbS-=CN based on the decrease in integrated peak area from a HPLC data (at UV absorbance of 280 nm). Observed rates, k$_{obs}$, for the reaction were obtained with a 2000-, 8000- and 16000-fold excess of reduced glutathione in 100 mM Na$_2$HPO$_4$, pH 8. Reduced glutathione stock solution (1 M) was prepared with MQ water. The pH was adjusted to pH 7 without exceeding pH 7.5 and was degassed thoroughly with argon for 10 minutes. Glutathione solutions of 125 mM, 500 mM and 1000 mM were then subsequently prepared (by dilution of the 1 M glutathione stock), with a final Na$_2$HPO$_4$ concentration of 100 mM (using a buffer solution of 1 M Na$_2$HPO$_4$, pH 8). The solutions were also thoroughly argon degassed.

UbS-=CN solution (60 µM, 100 mM Na$_2$HPO$_4$, pH 8) was made up from a stock of UbS-=CN in MQ water and 1 M Na$_2$HPO$_4$, pH 8. UbS-=CN and reduced glutathione stock solutions were incubated at room temperature for 10 minutes prior to use in kinetic reactions. UbS-=CN concentration was determined using the standard curve described above.

The reaction was initiated by the addition of UbS-=CN (500 µL, 60 µM) to pre-incubated (5 minutes) reduced glutathione stock solution (500 µL) in a Eppendorf thermomixer (37° C., 600 rpm). A total of 9 time points were taken per reaction (0, 1, 5, 15, 30, 60, 120, 180 and 360 minutes) and the reaction was repeated in duplicate. At an appropriate time point, 100 µL of reaction solution was quenched with 4 µL quenching solution (25% TFA in acetonitrile), and was subjected to LC-ESI-MS analysis (instrument parameters below).

Initial time points (0 minutes) were obtained for each reaction by pre-mixing the appropriate reduced glutathione stock solution (50 µL) with quenching solution (4 µL), followed by the addition of UbS-=CN (50 µL, 60 µM). Quenched reaction solution (5 µL injection) was analysed by HPLC (see General Methods, protein LC-MS) with a gradient of 10% to 75% acetonitrile (flow rate; 0.3 mL/min) over 20 minutes. Absorbance data at 280 nm was collected for UbS-=CN (retention time; ~13.8 minutes) and the peak was integrated automatically by the Agilent Chemstation v.4 software. Data were fit to an exponential decay function to allow determination of the half-life. The observed rate, k$_{obs}$, for each run were calculated from the half-life equation:

$$t_{1/2} = \frac{\ln 2}{k_{obs}}$$

and k$_{obs}$ for each run was plotted against the concentration of reduced glutathione to obtain the rate constant, k, from the slope of the plot. All data processing was performed using Prism v.6.0d (GraphPad).

Covalent Modification of Deubiquitinases with UbS-=CN 100 mM Na$_2$HPO$_4$ phosphate buffer, pH8 and deubiquitinase enzymes (DUBs; UCH-L3 residues 1-103 (93 µM), OTUB2 residues 1-234 (275 µM), His-USPS residues 1-858 (21 µM), His-USP21 residues 196-565 (25 µM) GST-USP2 residues 1-353 (7 µM), His-TRABID residues 245-697 (18 µM)) were individually aliquoted into 1.5 mL microcentrifuge tubes and placed on-ice to give a final DUB concentration of 5 µM (based on a 50 µL reaction volume). The DUB solutions were incubated in an Eppendorf thermomixer (30° C., 400 rpm) for 5 minutes before the addition of UbS-=CN (8.6 µL, 116 µM in MQ water) was added to each tube to give a final UbS-=CN concentration 20 µM (in a reaction volume of 50 µL).

A control sample of UbS-=CN (20 µM in 50 µL reaction volume), which contained no DUB, was also prepared and incubated alongside DUB samples. SDS sample buffer contained 2-mercaptoethanol at a final concentration of 179 mM which illustrates redox stability of the modifications.

The reaction solution was incubated at 30° C. for 1 hour at which time 16 µL of reducing SDS-gel loading buffer (NuPAGE LDS loading buffer (4λ), 715 mM 2-mercaptoethanol) was added to each microcentrifuge tube. The quenched reaction solutions were boiled for 1 minute at 100° C. and then 15 μL of solution was analysed by SDS-PAGE (NuPAGE Bis-Tris, 4-12%).

Synthesis of (E)-methyl 3-tosylacrylate (2)

PhI(OAc)2 (966 mg, 2 mmol) was added to a suspension of methyl methacrylate (2 mmol), sodium arenesulfinate (8.0 mmol), and KI (328 mg, 2.0 mmol) in $CH_3CN$ (8 mL). The reaction mixture was stirred vigorously at room temperature for 1 h under an inert atmosphere. The reaction mixture was quenched by the addition of saturated $Na_2S_2O_3$ aq. (20 mL) followed by a saturated aqueous solution of $NaHCO_3$ aq. (20 mL). Further stirring was followed by extraction with EtOAc (3×50 mL). The combined organic phases were washed with saturated NaCl aq. (75 mL) and dried over $Na_2SO_4$. The organic solvent was removed in vacuo and the crude product was directly purified by flash chromatography using a Reveleris® X2 flash chromatography system (Grace) (Reveleris® 12 g silica column; EA:Hexane; 12% to 100% EA gradient elution).

Expression and Purification of E1 Activating Enzymes

His-tagged human UBA1 and UBA7 cDNA were cloned into the pFastBacHTB vector (Life Technologies) with N-terminal 6×His tags. A C632A mutant of UBA1 was made by Quikchange mutagenesis. Dac-tagged[6] NAE1 and UBA3 CDNA were cloned into the pFastBacDual vector (Life Technologies). The recombinant E1s were expressed using the Bac-to-Bac system (Life Technologies). Briefly, the bacmid DNAs were generated in DH10Bac cells, and the resulting baculovirus was generated and amplified in *Spodoptera frugiperda* Sf21 insect cells (Life Technologies). E1s were overexpressed in Sf21 insect cells grown in Insect-Xpress medium (Lonza). Cells were harvested 72 h after infection. For UBA1, UBA1 C632A and UBA7 cells were lysed by sonication in lysis buffer (25 mM HEPES, 150 mM NaCl, 0.3% Triton X-100, 0.5 mM EGTA, 0.1 mM EGTA, 1 mM DTT, Leupeptin & Pefabloc. The lysate was clarified by ultracentrifugation (40,000 rpm for 1 h). The supernatant was subjected to Ni-NTA affinity chromatography (Qiagen) and washed with wash buffer (25 mM HEPES, 250 NaCl, 20 mM imidazole 0.3% Triton X-100, 0.5 mM EGTA, 0.1 mM EGTA, 1 mM DTT). Protein was eluted with imidazole and dialyzed into storage buffer (25 mM HEPES pH 7.5, 10% glycerol, 150 mM NaCl, 0.03% Brij35, 1 mM DTT). In the case of wt UBA1, the N-terminal His-tag was removed with TEV protease and protease was subsequently depleted by incubation with Ni-NTA resin. For Dac-NAE1-UBA3, cells were lysed by sonication in buffer (40 mM Tris pH 7.5, 0.2% Triton X-100, 0.5 mM ETDA, 0.5 mM EGTA, 1 mM DTT, protease inhibitor). Clarified lysate was incubated with ampicillin sepharose and washed with wash buffer (40 mM HEPES pH 7.5 150 mM NaCl, 0.03% Brij35) and eluted with wash buffer supplemented with 5% glycerol and 10 mM ampicilin buffer. Eluted protein was further purified by gel filtration (Superdex 200 16/60, GE Healthcare) using wash buffer as running solvent.

GST-tagged SAE1 and His-tagged UBA2 were cloned into the pET DUET-1 vector and co-expressed protein was expressed in *E. coli* BL21(DE3) cells. Cells were lysed in lysis buffer (50 mM Tris pH 7.5, 150 mM NaCl, 1 mM EGTA 1 mM EDTA, 1 mM Leupeptin, 1 mM DTT, 0.03% Brij-35, 1% Triton-X100). Nickel affinity purification using Ni-NTA resin (Qiagen) was carried out on the clarified lysate and resin was washed with buffer (50 HEPES pH 7.5, 150 mM NaCl, 5 mM imidazole, 0.03% Brij35, 10% glycerol) protein was eluted with elution buffer (50 mM HEPES pH 7.5, 150 mM NaCl, 400 mM imidazole, 0.03% Brij35, 10% glycerol). Protein was subsequently purified using glutathione resin and washed with wash buffer. Protein was then eluted with GST elution buffer (50 mM HEPES pH 7.5, 150 mM NaCl, 10 mM GSH, 0.03% Brij35, 10% glycerol).

Activity-Based Labelling of E1 Activating Enzymes with E2 Probes

E2 probes (14 μM) were mixed with E1 enzyme (3.5 μM) and diluted 10× reaction buffer (500 mM $Na_2HPO_4$ pH 8) or 10×Ub-ATP buffer (500 mM $Na_2HPO_4$ pH 8, 20 μM ubiquitin, 20 mM ATP) to a final volume of 15-50 μL. Reactions were incubated at 30° C. and 15 μL aliquots were taken at 1 and 5 h time points which were quenched with 5 μL of reducing SDS-gel loading buffer (NuPAGE LDS loading buffer (4×), 715 mM 2-mercaptoethanol). The quenched reaction solutions were boiled for 5 minute at 100° C. and then 4 μL was analysed by SDS-PAGE (NuPAGE Bis-Tris, 4-12%).

Compatibility of Probe Labelling with Reducing Agents, Acids and Bases

Activity-based crosslinking against Uba1 was carried out pro rata as described above with Ubc13-=CN and Ubc13-VME probes but in a reaction volume of 20 μL and in the presence of 1 mM TCEP, DTT and 2-mercaptoethanol (10 mM stock solutions) and 10 mM TCEP, DTT and 2-mercaptoethanol (100 mM stock solutions).

To test the stability of the formed crosslinks, crosslinking reactions with Ubc13-=CN and Ubc13-VME were carried out on a larger scale in a final volume of 140 μL. No additional reducing agent was added and reactions were again incubated for 3 h at 30° C. 20 μL aliquots of each reaction were then treated with 10 μL of the following: 750 mM TCEP, 750 mM 2-mercaptoethanol, 1.5 M HCl, 15% TFA (aq.), 15% formic acid (aq.), 15% acetic acid (aq.) and 1.5 M NaOH. The treated samples were then incubated for 2 h at 23° C. Samples were then diluted with 4×LDS loading buffer+BME and 6 μL was analyzed by SDS-PAGE.

Competitive ABPP of UBA1 with PYR-41

Human UBA1 (500 nM) was incubated with Pyr41 (50 μM) or DMSO control respectively in 50 mM $Na_2HPO_4$, pH 8 buffer for 15 minutes at room temperature. Ubiquitylation components (Ub-Fluorescein (boston Biochem U-580), ATP and $MgCl_2$) were then added as a stock solution (final concentrations of 2 μM, 2 mM and 10 mM respectively) to the pre-incubated samples and were then incubated for a further 15 minutes at 30° C. in an Eppendorf thermomixer. The samples were then divided into two portions and were treated with UBE2N-=CN (14 μM) or with MQ water (to account for the minor volume change (4%) on E2-probe addition). Samples were then left to incubate for 1 hour at 30° C. in an Eppendorf thermomixer. 4×LDS loading buffer (non-reducing) was added to a final concentration of 1× (For western blotting, BME was added to the LDS treated samples, which were then heated). Samples were then subjected to 4-12% SDS-PAGE (MOPS buffer, 45 minutes, 200V) and were analysed by fluorescence imaging (excitation wavelength 273 nM) on a Fujifilm FLA-1500 imager and by western blotting (anti-His detection; experimental conditions as above).

Cell Culture and Lysis Protocol

HEK 293 cells were cultured in Dulbecco's modified Eagle's medium (DMEM) supplemented with 10% foetal bovine serum, 2 mM L-glutamine and antibiotics (100 Units $ml^{-1}$ penicillin, 100 $\mu gml^{-1}$ streptomycin). All cells were cultured at 37° C. in a 10% $CO_2$ humidified atmosphere.

Cells from one culture flask (75 $cm^2$, Nunclon™) at ~90% confluence were washed with Dulbecco s Phosphate Buffered Saline (DPBS) and trypsinised (0.05% Trypsin-EDTA (1×), Gibco) at room temperature. Trypsinised cells from three culture flasks were combined, centrifuged (1200 rpm, 4° C., 3 minutes) and washed with DPBS (repeated once). Cells were snap frozen with liquid nitrogen and stored at −80° C.

The combined cells from three culture flasks were lysed with 50 mM Tris pH 7.5, 150 mM NaCl, 1% Nonidet P40 substitute, 0.25% sodium deoxycholate, 1 mM AEBSF, 1 mM sodium orthovanadate, 2 mM benzamidine, 1 mM sodium fluoride, Roche complete EDTA free inhibitor cocktail, and benzonase (Sigma-Aldrich) using 200 μL 1.1× lysis buffer per culture flask. The cell pellet was incubated on-ice for 20 minutes. Lysates were cleared using centrifugation (13200 rpm, 30 minutes) and filtration through 0.45 μm spin filters (Millipore) to remove cell debris. Lysates were then diluted approximately 3 fold with 50 mM Tris pH 7.5, 150 mM NaCl, 1 mM PMSF, Roche complete EDTA free inhibitor cocktail, 1.33 mM TCEP to bring the detergent concentration down to 0.3% and a final protein concentration of 2.8 mg/mL as determined by Bradford assay (595 nm).

Activity-Based Profiling of Protein Extracts

E2 probes were added to 125 μg of protein extract (50 μL) and incubated at 30° C. for 3 hours. All probes based on UDE2D1, UBE2D2, UBE2D3 and UBE2M were used at a concentration of 5 μM. Probes based on UBE2L3, UBE2L6, UBE2N, UBE2H and UBE2I were used at 25 μM. Post-incubation, the DUB USP2 (1 μM) was added to parallel incubations with UBE2D1-based probes and incubated at 25° C. for 30 min to check if polyubiquitination was exacerbating labelling profile. Labelling was quenched by the addition of 1 part 4×LDS loading buffer (Life Technologies) supplemented with 715 mM 2-mercaptoethanol (BME) to 3 parts probe-treated protein extract. Proteins were resolved by SDS-PAGE (10%) and transferred to nitrocellulose membrane (20 V for 40-60 min) by semi-dry transfer using a Novex Semi-dry device (Life Technologies). Membranes were blocked by incubation with 5% milk powder in phosphate buffered saline+0.1% Tween 20 (PBST) for 1 h. His-tagged species were probed with 1:10000 anti-His primary antibody (Clontech) in PBST+5% milk powder for 30 min at room temperature. Detection was carried out by incubation with 1:2500 anti-mouse-HRP conjugated antibody (Cell Signalling Technologies) in PBST+5% milk powder for 1 h at room temperature. ECL Prime substrate (GE Life Sciences) was used for visualization in accordance with the manufacturers protocol. Probing for UBA1 was carried out with anti-UBA1 primary antibody (Sigma E3152) and incubated for 1 h at room temperature. Detection was carried out by incubation with 1:15000 anti-mouse-HRP conjugated antibody (Cell Signalling Technologies) in PBST+5% milk powder for 1 h at room temperature.

Activity-Based Profiling of Alkylated Cell Extract

The same procedure was followed as described for unmodified protein extracts but prior to addition of probe, extracts were treated with 20 mM N-ethylmaleimide (NEM; 1M stock solution in EtOH) for 20 minutes at 23° C.

Expression of AzF Containing UBE2D1 C86 Conjugating Enzyme (UBE2D1 C86 AzF3)

Quikchange site-directed mutagenesis was used to introduce amber stop codons into a plasmid harbouring UBE2D1 C21S C107S C111S (pHISTEV30a-UBE2D1C86) at residue position 3 (upstream of the N-terminal His tag). The 5'-GGAGATATACATATGTCGTAGTACCATCACCAT-CACC-3' (SEQ ID NO:16) forward and 5'-GGTGATGGT-GATGGTACTACGACATATGTATATCTCC-3' (SEQ ID NO:17) reverse primer was used yielding the plasmid pHISTEV30a-UBE2D1C86-TAG3. Successful mutation was confirmed by DNA sequencing. Mutations (Y32T, E107N. D158P, I1591L162Q) which are reported to permit the incorporation of azido-phenylalanine (AzF),[7] were introduced into a *Methaacoldococcus Janaschi* tyrosyl-tRNA synthetase gene (MjYRS) flanked by NdeI and PstI restriction sites to yield plasmid pBK-AzFRS. The gene was amplified by PCR and BglII and SalI restriction sites were introduced at the 5'- and 3'-ends with the 5'-AGATT-GAGATCTATGGACGAGTTCGAAATG-3' (SEQ ID NO:18) forward and 5'-AGTTGGGTCGACT-TATAATCTCTTTCTAATTGGC-3' (SEQ ID NO:19) reverse primer. PCR product was digested with BglII and SalI restriction enzymes (Fermentas). In parallel, the pEVOL-pBoF plasmid,[8,9] (kindly provided by Prof. Peter Schultz) was similarly treated. This plasmid contains constitutive and inducible copies of a mutant MjYRS which directs the incorporation of p-boronophylalanine. Digested vector and insert were ligated with T4 DNA Ligase. Replacement of the inducible copy of the mutant MjYRS gene with the AzF mutant was confirmed by DNA sequencing which yielded plasmid pEVOL-BoFRS/AzFRS. To replace the constitutive copy of the mutant MjYRS pBK-AzFRS and pEVOL-BoFRS/AzFRS were treated with NdeI and PstI restriction enzymes and the insert from pBK-AzFRS was cloned into the the pEVOL backbone yielding pEVOL-AzFRS. Chemically competent BL21-DE3 cells were cotransformed by heat shock with pEVOL-AzFRS and pHISTEV30a-UBE2D1C86. Luria-Bertani medium (LB; 50 mL) was supplemented with chloramphenicaol (34 ug/ml) and ampicilin (100 ug/ml) and was incolulated with the cotransformed pET156P-UBE2H-TAG3 recovered cells. LB supplemented with chloramphenicaol (34 ug/ml) and kanamycin (50 ug/ml) was inoculated with the cotransformed 200 μl pHISTEV30a-UBE2D1C86 recovered cells. Cultures were incubated overnight at 37° C. were diluted 1:20 into fresh LB medium (500 ml) with appropriate antibiotics reduced to 50% of the concentrations used in the overnight cultures. Cells were cultured (37° C., 220 rpm) until $OD_{600}$ ~0.6-0.8 and then AzF (1 mM; Bachem) and arabinose (0.02%) was added followed by chilling for 15 min in an ice bath. IPTG (0.1 mM) was then added and cells were cultured overnight hours at 20° C. Harvested cells were lysed in lysis buffer (50 mM Tris pH 8.0, 250 mM NaCl, 10 mM Imidazole and Roche Complete EDTA free protease inhibitor tablet). Protein was loaded onto Ni-NTA agarose (Qiagen) and washed with lysis buffer. UDE2D1-C86-AzF3 was eluted with elution buffer (50 mM Tris pH 8.0, 150 mM NaCl, 100 mM Imidazole).

TAMRA and Biotin Labelling of UDE2D1-C86-AzF3

UBE2D1-C86-AzF3 (1 mL @ 0.8 mg/mL; determined by Bradford assay) was incubated (in the absence of light) with DBCO-PEG4-Biotin (Jena Bioscience) or DBCO-$PEG_4$-TAMRA (Jena Bioscience) (20 mM and 5 mM DMSO stocks respectively) at a final concentration of 250 μM in an eppendorf thermomixer (300 rpm) at 25° C. for 5 hours and subsequently overnight at 20° C. The reaction was monitored by LC-MS, The conjugated material was incubated with 5 mM TCEP at room temperature for 45 minutes and was then buffer exchanged into 100 mM $Na_2HPO_4$, 150 mM NaCl. pH 8, 0.1 mM TCEP using a PD10 desalting column (GE Healthcare). The TAMRA conjugate was further purified by size exclusion chromatography using a HiLoad 16/600 Superdex 75 pg column, Running buffer was 100 mM $Na_2HPO_4$, 100 mM NaCl, pH 8. The protein conjugates (UBE2D1-C86-Biotin and UBE2D1-C86-TAMRA) were then concentrated using an Amicon centrifugal filter (3KDa MWCO) to a concentration of 2-3 mg/mL (determined by Bradford assay).

VME Labelling of UBE2D1-C86-Biotin and UBE2D1-C86-TAMRA

UBE2D1-C86-Biotin or UBE2D1-C86-TAMRA (1 mL 1 mg/mL) was incubated with 4 mol equivalents of 2 (20 mM DMSO stock) at room temperature for 1 hour. The reaction was monitored by LC-MS. Once complete, the VME-labelled protein was buffer exchanged into 100 mM $Na_2HPO_4$, 150 mM NaCl, pH8, using a PD10 desalting column (GE Healthcare) and using an Amicon centrifugal filter (3KDa MWCO) to a concentration of 2-3 mg/mL (determined by Bradford assay).

REFERENCES FOR MATERIALS AND METHODS SECTION

[1] C. Chatterjee, R. K. McGinty, B. Fierz, T. W. Muir, Nat Chem Biol 2010, 6, 267-269.
[2] J. Chen, Y. Ai, J. Wang, L. Haracska, Z. Zhuang, Nat Chem Biol 2010, 6, 270-272.
[3] D. Komander, M. J. Clague, S. Urbé, Nat Rev Mol Cell Biol 2009, 10, 550-563.
[4] S. Virdee, Y. Ye, D. P. Nguyen, D. Komander, J. W. Chin, Nature Chemical Biology 2010, 6, 750-757.
[5] F. El Oualid, R. Merkx, R. Ekkebus, D. S. Hameed, J. J. Smit, A. de Jong, H. Hilkmann, T. K. Sixma, H. Ovaa, Angew Chem Int Ed Engl 2010, 49, 10149-10153.
[6] D. W. Lee, M. Peggie, M. Deak, R. Toth, Z. O. Gage, N. Wood, C. Schilde, T. Kurz, A. Knebel, Anal Biochem 2012, 428, 64-72.
[7] J. W. Chin, S. W. Santoro, A. B. Martin, D. S. King, L. Wang, P. G. Schultz, J Am Chem Soc 2002, 124, 9026-9027.
[8] T. S. Young, I. Ahmad, J. A. Yin, P. G. Schultz, J Mol Biol 2010, 395, 361-374.
[9] E. Brustad, M. L. Bushey, J. W. Lee, D. Groff, W. Liu, P. G. Schultz, Angewandte Chemie International Edition 2008, 47, 8220-8223.

Results & Discussion

We reasoned that a strategy for making ABPs directed towards such activity would be to use an E2 as a binding element and exploit the juxtaposition of catalytic cysteine residues between functional E1-E2 and E2-E3 pairs (Scheme 10 & D). The conserved E2 catalytic cysteine could serve as a labelling site for installation of a warhead such as an activated vinylsulfide (AVS). Aqueous nucleophilic thiol-yne addition to electron deficient alkynes generates an AVS,[6] which has been shown to undergo nucleophilic thiol-ene addition affording a geminal bisthioether, which would mirror the geometry of the transthioesterification intermediate (Scheme 1A-C)[6c,7]. AVS installation can also be carried out by an addition-elimination reaction with arylsulfonyl substituted doubly activated vinyl compounds which yields the trans regioisomer (FIG. 1A) and has been demonstrated in a protein context.[7c,8] Installation of the warhead by such a simple site-specific labelling reactions, compatible with aqueous buffer, micromolar protein concentration and near physiological pH, would provide a platform for the preparation of ABPs built on recombinant As Ub functionalized with C-terminal activated vinyl groups have been successfully used as ABPs directed towards deubiquitinating enzymes (DUBs),[9] to test the AVS moiety as a warhead we labelled a truncated ubiquitin bearing a C-terminal thiol group ($Ub_{1-74}$-SH; FIG. 5I). $Ub_{1-74}$-SH (120 µM) was labelled with 4 eq. of the nitrile TDMA 1 ((E)-3-tosylacrylonitrile) for 30 min at 25° C. in aqueous pH 8 phosphate buffer. The major product (90%) was the unsaturated thioacrylonitrile (UbS-=CN; FIG. 1; Figure S2). We predicted the rate constant of this thia-addition to be ~$10^4$ $M^{-1}s^{-1}$ as observed with similarly activated vinyl groups.[10] A secondary product was the saturated Michael adduct (Figure S2 & S6). Small molecules were next removed by buffer exchange and UbS-=CN (20 µM) was incubated with a panel of DUBs (5 µM) for 1 h at 30° C. 5 of 6 DUBs tested underwent labelling with no apparent off-target labelling showing that like related species[9], UbS-=CN can function as an ABP (Figure S3). To test the generality of this chemistry and the possibility of installing a kinetically distinct warhead we explored a TDMA with a methyl ester substituent in place of the nitrile moiety, (E)-methyl 3-tosylacrylate 2[11] (Figure S4). Labelling of $Ub_{1-74}$-SH with 2 generated a species with a mass consistent with the unsaturated thiomethyl acrylate (UbS-VME; Figure S5) as determined by LC-MS. Formation of the saturated adduct was reduced relative to 1 (<3%) and at pH 9 this was <1% (Figure S6). We next carried out model addition reactions on UbS-=CN and UbS-VME using glutathione (GSH). A single GSH adduct was observed and the reaction went to completion with excess GSH (FIG. 1B; Figure S7). The elimination product,[6b,12] $Ub_{1-74}$-SH, was only observed with UbS-VME (21%) (Figure S8D). Taken together, TDMAs can rapidly and chemoselectively install AVSs onto protein which undergo orthogonal functionalization by 'click' reaction with a second cysteine containing protein or peptide. Rate constants under pseudo first order conditions were found to be $1.52 \times 10^{-3}$ $M^{-1}s^{-1}$ and $7.84 \times 10^{-3}$ $M^{-1}s^{-1}$ for UbS-=CN and UbS-VME, respectively (FIG. 10; Figure S8). We also generated UbS-VME* by reaction with methyl propiolate[6] (Figure S9). GSH addition was 5-fold lower than for addition to UbS-VME, most likely on account of the steric and electronic effects associated with the different regioisomers (Figure S10). To explore labelling with 1 to prepare an E2 probe we expressed His-tagged UBE2N (Figure S11 & S12). Labelling with 4 eq. of 1 was achieved within 30 minutes at 25° C. (Figure S12). We tested the ability of UBE2N labelled with 1 (UBE2N-=CN) to undergo activity-based labelling of human Ub E1 activating enzyme UBA1,[13] which has 19 cysteine residues in addition to the catalytic C632. In pH 8 phosphate buffer UBA1 (3.5 µM) was incubated with 4 eq. of UBE2N-=CN at 30° C. After 1 h, labelling of UBA1 was observed which was strictly dependent on the presence of C632 (FIG. 2A). Labelling was time-dependent and was enhanced in the presence of Ub and ATP[14]. These data show that UBE2N-=CN can be used as an ABP directed towards transthioesterification activity between E1-E2. Similar labelling efficiency was observed with UBE2N-VME and the stability of the bisthioether linkage between UBE2N-=CN and UBE2N-VME with UBA1 was stable towards reducing and acidic conditions (Figure S13 & S14). We next prepared thioacrylonitrile and thiomethyl acrylate probes based on the E2s UBE2I, UBE2M, UBE2L6 and UBE2L3. UBE2I is cognate for the SUMO E1, SAE; UBE2M is cognate for the NEDD8 E1, NAE1; UBE2L6 is cognate for the ISG15 E1, UBA7.[13] UBE2L3 was chosen as an additional Ub-specific E2. All of these E2s contain 3 or 4 cysteine residues but based on analysis of crystal structures and modelling, with the exception of C138 in UBE2I, non-catalytic cysteines were not located at the E1-E2 interface.[15] However, for UBE2L3 and UBE2L6 we made double mutants where the 2 non-catalytic cysteines were mutated to serine (UBE2L3* and UBE2L6*). We also prepared mutants with an additional Ser to Ala mutation (UBE2L3 and UBE2L6) as this residue is proximal to the catalytic cysteine,[16] and we had concerns about intramolecular oxa-addition to the installed AVS. All of the E2s were labelled with 4 cysteine eq. of 1 and 2 and were characterized by LC-MS (Figure S12). UBE2I and UBE2M contained 4 and 5 cysteines respectively but only 2 were modified on UBE2I and 4 on UBE2M. Inspection of crystal structures,[17] showed that non-catalytic C41 and C75 in UBE2I and C95 in UBE2M were not solvent accessible. We next tested E2 probes against recombinant UBA1, SAE1, NAE1, and UBA7 (Figure S15). Probes only labelled an E1 if it was built on a cognate E2 binding element (FIG. 2B-E). We next explored competitive ABPP,[4a] with the UBA1 inhibitor PYR-41.[18] PYR-41 is the only reported E1 inhibitor that directly competes with transthioesterification activity and covalently modifies the catalytic cysteine of UBA1. E1 activity was monitored by observing thioesterification with fluorescein-labelled Ub (fluo-Ub) (FIG. 2F). Post-incubation of DMSO-treated cells with UBE2N-=CN efficiently outcompeted thioesterification of UBA1 with fluo-Ub. Activity was inhibited in the PYR-41 (50 μM) treated sample and post-incubation with UBE2N-CN resulted in a striking reduction in labelling. This showed that our probes could be used to carry out targeted screening of the poorly characterized pharmacological space associated with transthioesterification activity between E1-E2, and could potentially be done on a high-throughput scale with inclusion of a fluorescent reporter tag.[19]

We next tested whether E2 probes could label endogenous proteins in a complex proteome. We prepared additional thioacrylonitrile and thiomethyl acrylate probes built on UBE2D1, UBE2D2, UBE2D3 and UBE2H. UBE2D1-3 have been shown to be promiscuous E2s that support activity of many E3s.[20] UBE2D1-3 contain 4 cysteines and as before all cysteines were labelled as modification of all cysteine residues in an E2 with bulky fluorophores has been shown to have no effect on affinity to the HECT E3, E6AP,[21] but we also prepared a mutant of UBE2D1 where the non-catalytic cysteines were mutated to serine (UBE2D1C86). UBE2H was chosen as it only has a single catalytic cysteine. Human embryonic kidney cell (HEK293) extracts (125 μg) were incubated with empirically determined probe concentrations (5-25 μM). After incubation at 30° C. for 3 h, all probes with a Ub E2 binding element produced a labelled band consistent with the molecular weight of modified UBA1 as determined by anti-His and anti-UBA1 western blot and labelling was dependent on the presence of the AVS warhead (FIGS. 3 & S16). Additional labelling varied from undetectable to significant depending on E2. DUB treatment with USP2,[22] did not reduce labelling confirming modification of numerous distinct proteins. In all cases, probes bearing the thiomethyl acrylate moiety showed increased labelling. Promiscuous UBE2D1-3 showed the most extensive labelling and UBE2D1C86 exhibited a profile similar to UBE2D1 showing that, at least in the case of UBE2D1, overlabelling did not compromise specificity. Surprisingly, the SUMO and NEDD8 specific E2s exhibited a significant labelling profile suggestive of underappreciated E3 partners. Proteome labelling of extracts pretreated with 10 mM N-ethylmaleimide were not probe reactive indicative of cysteine-specific labelling (Figure S17). As alkyl derivatives of vinylsulfides have similar or higher rate constants, and have been successfully used to prepare related probes that are enzyme family specific at similar probe concentrations,[9] it was likely that the probes were undergoing on-target mechanistic labelling of associated enzymes such as HECT and RBR E3 ligases. To effectively explore this further by allowing efficient enrichment, and to increase the versatility of our new ABPs as mentioned above, we designed and prepared a second generation biotin and fluorescent tetramethylrhodamine (TAMRA) conjugated ABP built on the UBE2D1C86 binding element (Figure S18). To achieve this we genetically encoded azido-L-phenylalanine,[23] upstream of the vector-derived His tag. Purified protein was labelled with DBCO-PEG-Biotin and DBCO-PEG-TAMRA using copper-free click chemistry.[24] Subsequent installation of the thiomethyl acrylate warhead was carried by labelling with 2 yielding Biotin-UBE2D1C86-VME and TAMRA-UBE2D1C86-VME.

In conclusion, we have demonstrated that use of TDMAs to chemoselectively install thioacrylonitrile and thiomethyl acrylate groups onto recombinant proteins. Proximity effects arising from juxtaposition of the AVSs with a cysteine residue upon protein-protein binding leads to efficient formation of stable covalent labelling as exemplified by the production of ABPs directed against 4 E1s. These ABPs should prove to be valuable tools for targeted profiling of E1 pharmacological space with the ability to assess cross selectivity. Potential for E3 profiling is currently underway which will be facilitated by our biotin- and TAMRA conjugated probes. We envisage this technology will also find utility in protein engineering and material sciences in general.

[1] D. Komander, M. Rape, *Annu. Rev. Biochem* 2012, 81, 203-229.
[2] aM. D. Petroski, *BMC Biochem* 2008, 9 Suppl 1, S7; bD. Hoeller, C.-M. Hecker, I. Dikic, *Nat. Rev. Cancer* 2006, 6, 776-788; cP. Cohen, *Nat. Immunol.* 2014, 15, 521-529.
[3] aA. Hershko, A. Ciechanover, *Annu. Rev. Biochem* 1998, 67, 425-479; bJ. J. Smit, T. K. Sixma, *EMBO Rep* 2014, 15, 142-154.
[4] aM. J. Niphakis, B. F. Cravatt, *Annu. Rev. Biochem* 2014, 83, 341-377; bL. E. Sanman, M. Bogyo, *Annu. Rev. Biochem* 2014, 83, 249-273.
[5] aH. An, A. V. Statsyuk, *J. Am. Chem. Soc.* 2013; bX. Lu, S. K. Olsen, A. D. Capili, J. S. Cisar, C. D. Lima, D. S. Tan, *J. Am. Chem. Soc.* 2010, 132, 1748-1749.
[6] aH.-Y. Shiu, H.-C. Chong, Y.-C. Leung, M.-K. Wong, C.-M. Che, *Chem-Eur J* 2010, 16, 3308-3313; bH.-Y. Shiu, T.-C. Chan, C.-M. Ho, Y. Liu, M.-K. Wong, C.-M. Che, *Chem-Eur J* 2009, 15, 3839-3850; cV. X. Truong, A. P. Dove, *Angew. Chem. Int. Ed. Engl.* 2013, 52, 4132-4136.
[7] aH. Kuroda, I. Tomita, T. Endo, *Polymer* 1997, 38, 6049-6054; bA. L. Krasovsky, V. G. Nenajdenko, E. S. Balenkova, *Russ. Chem. Bull.* 2002, 51, 2080-2085; cD. H. Grayson, S. H. O'Donnell, *ARKIVOC* 2003.
[8] S. Strickson, D. G. Campbell, C. H. Emmerich, A. Knebel, L. Plater, M. S. Ritorto, N. Shpiro, P. Cohen, *Biochemical J* 2013, 451, 427-437.
[9] aA. Borodovsky, H. Ovaa, N. Kolli, T. Gan-Erdene, K. D. Wilkinson, H. L. Ploegh, B. M. Kessler, *Chem Biol* 2002, 9, 1149-1159; bM. Altun, H. B. Kramer, L. I. Willems, J. L. McDermott, C. A. Leach, S. J. Goldenberg, K. G. S. Kumar, R. Konietzny, R. Fischer, E. Kogan, M. M. Mackeen, J. McGouran, S. V. Khoronenkova, J. L. Parsons, G. L. Dianov, B. Nicholson, B. M. Kessler, *Chem Biol* 2011, 18, 1401-1412; cJ. F. McGouran, S. R. Gaertner, M. Altun, H. B. Kramer, B. M. Kessler, *Chem Biol* 2013.

[10] L. Yi, H. Li, L. Sun, L. Liu, C. Zhang, Z. Xi, *Angew. Chem. Int. Ed. Engl.* 2009, 48, 4034-4037.

[11] P. Katrun, S. Chiampanichayakul, *Eur J Org Chem* 2010, 5633-5641.

[12] G. Joshi, E. V. Anslyn, *Org. Lett.* 2012, 14, 4714-4717.

[13] B. A. Schulman, J. W. Harper, *Nat. Rev. Mol. Cell. Biol.* 2009, 10, 319-331.

[14] aA. Hershko, H. Heller, S. Elias, A. Ciechanover, *J. Biol. Chem.* 1983, 258, 8206-8214; bC. M. Pickart, E. M. Kasperek, R. Beal, A. Kim, *J Biol Chem* 1994, 269, 7115-7123.

[15] aD. T. Huang, H. W. Hunt, M. Zhuang, M. D. Ohi, J. M. Holton, B. A. Schulman, *Nature* 2007, 445, 394-398; bS. K. Olsen, C. D. Lima, *Mol Cell* 2013, 49, 884-896.

[16] L. Huang, E. Kinnucan, G. Wang, S. Beaudenon, P. M. Howley, J. M. Huibregtse, N. P. Pavletich, *Science* 1999, 286, 1321-1326.

[17] aH. Tong, G. Hateboer, A. Perrakis, R. Bernards, T. K. Sixma, *J Biol Chem* 1997, 272, 21381-21387; bD. T. Huang, A. Paydar, M. Zhuang, M. B. Waddell, J. M. Holton, B. A. Schulman, *Mol Cell* 2005, 17, 341-350.

[18] Y. Yang, J. Kitagaki, R.-M. Dai, Y. C. Tsai, K. L. Lorick, R. L. Ludwig, S. A. Pierre, J. P. Jensen, I. V. Davydov, P. Oberoi, C.-C. H. Li, J. H. Kenten, J. A. Beutler, K. H. Vousden, A. M. Weissman, *Cancer Res* 2007, 67, 9472-9481.

[19] aD. A. Bachovchin, L. W. Koblan, W. Wu, Y. Liu, Y. Li, P. Zhao, I. Woznica, Y. Shu, J. H. Lai, S. E. Poplawski, C. P. Kiritsy, S. E. Healey, M. DiMare, D. G. Sanford, R. S. Munford, W. W. Bachovchin, T. R. Golub, *Nat. Chem. Biol.* 2014, 10, 656-663; bD. A. Bachovchin, S. J. Brown, H. Rosen, B. F. Cravatt, *Nat. Biotechnol.* 2009, 27, 387-394.

[20] Y. Ye, M. Rape, *Nat Rev Mol Cell Biol* 2009, 10, 755-764.

[21] Z. M. Eletr, B. Kuhlman, *J. Mol. Biol.* 2007, 369, 419-428.

[22] C. H. Emmerich, A. Ordureau, S. Strickson, J. S. C. Arthur, P. G. A. Pedrioli, D. Komander, P. Cohen, *Proc Natl Acad Sci USA* 2013, 110, 15247-15252.

[23] aJ. W. Chin, S. W. Santoro, A. B. Martin, D. S. King, L. Wang, P. G. Schultz, *J. Am. Chem. Soc.* 2002, 124, 9026-9027; bT. S. Young, I. Ahmad, J. A. Yin, P. G. Schultz, *J. Mol. Biol.* 2010, 395, 361-374.

[24] N. J. Agard, J. A. Prescher, C. R. Bertozzi, *J. Am. Chem. Soc.* 2004, 126, 15046-15047.

Further Examples

General Materials

All DNA constructs were verified by DNA sequencing, which was performed by The Sequencing Service, School of Life Sciences, University of Dundee, using DYEnamic ET terminator chemistry (Amersham Biosciences) on Applied Biosystems automated DNA sequencers. DNA for bacterial protein expression was transformed into E. coli BL21-DE3 (Merck) or BL21 DE3 RIL (codon plus) cells (Stratagene). With the exception of pCDF-PyIST, all cDNA plasmids and antibodies generated for this study are available to request through our reagents website (https://mrcppureagents.dundee.ac.uk/).

LC-MS was carried out with an Agilent 1200 LC-MS system fitted with a Max-Light Cartridge flow cell coupled to a 6130 Quadrupole spectrometer. The solvent system consisted of 0.05% trifluoroacetic acid (TFA) in $H_2O$ as buffer A, and 0.04% TFA acid in acetonitrile (MeCN) as buffer B. Protein UV absorbance was monitored at 214 and 280 nm. An Agilent ZORBAX 300SB-C3 5 um, 2.1×150 mm column was employed for proteins unless otherwise stated. Protein MS acquisition was carried out in positive ion mode and total protein masses were calculated by deconvolution within the MS Chemstation software (Agilent Technologies). Semi-preparative peptide HPLC was carried out on a Dionex Ultimate system with Thermo Biobasic C4 21.2×250 mm column at a flow rate of 10 ml $min^{-1}$. All solvents and reagents were purchased from Sigma Aldrich or VWR unless otherwise stated.

Synthesis of Alkyne-Functionalized TDAE 3

$PhI(OAc)_2$ (966 mg, 2 mmol) was added to a suspension of propargyl acrylate 1 (2 mmol), sodium arenesulfinate (8.0 mmol), and KI (328 mg, 2.0 mmol) in acetonitrile (MeCN) (8 mL). The reaction mixture was stirred vigorously at room temperature for 1 h under an inert atmosphere. The reaction mixture was then quenched by the addition of saturated $Na_2S_2O_3$ aq. (20 mL) followed by a saturated aqueous solution of $NaHCO_3$ aq. (20 mL). Further stirring was followed by extraction with ethyl acetate (EtOAc) (3×50 mL). The combined organic phases were washed with saturated NaCl aq. (75 mL) and dried over $Na_2SO_4$. The organic solvent was removed in vacuo and the crude product was directly purified by flash chromatography using a Reveleris® X2 flash chromatography system (Grace) (Reveleris® 12 g silica column; EA:Hexane; 15% to 25% to 100% EA gradient elution) to yield 3.

$^1$H NMR (500 Mhz, $CDCl_3$) δ 7.79 (2H, d, 8.4 Hz), 7.35-7.40 (3H, m), 6.81 (1H, d, 15.2 Hz), 4.78 (2H, d, 2.5 Hz), 2.51 (1H, t, 2.5 Hz), 2.46 (3H, s); $^{13}$C NMR (126 MHz, $CDCl_3$) δ 162.75, 145.83, 144.60, 135.21, 130.32, 129.19, 128.48, 76.50, 75.87, 53.23, 21.74.

HR-MS: observed $[M-H]^-$ 263.0361 (calculated 263.0373).

Synthesis of Alkyne-Functionalized TDAE 4

To synthesize 4, starting material N-propargylacrylamide, 2 was first prepared as previously described (ref. 3). Purification was carried out by flash chromatography using a Reveleris® X2 flash chromatography system (Grace) (Reveleris® 12 g silica column; EA:Hexane; 20% to 35% EA gradient elution). Analytical data corresponded to literature values. $PhI(OAc)_2$ (966 mg, 2 mmol) was added to a suspension of N-propargylacrylamide, 2 (2 mmol), sodium arenesulfinate (8.0 mmol), and KI (328 mg, 2.0 mmol) in $CH_3CN$ (8 mL). The reaction mixture was stirred vigorously at room temperature for 1 h under an inert atmosphere. The reaction mixture was quenched by the addition of saturated $Na_2S_2O_3$ aq. (20 mL) followed by a saturated aqueous solution of $NaHCO_3$ aq. (20 mL). Further stirring was followed by extraction with EtOAc (3×50 mL). The combined organic phases were washed with saturated NaCl aq. (75 mL) and dried over $Na_2SO_4$. The organic solvent was removed in vacuo and the crude product was directly purified by flash chromatography using a Reveleris® X2 flash chromatography system (Grace) (Reveleris® 12 g silica column; Toluene:EA; 0% to 1% to 10% EA gradient elution).

$^1$H NMR (500 Mhz, $CDCl_3$) δ 7.78 (2H, d, 8.3 Hz), 7.37 (2H, d, 8.5 Hz), 7.34 (1H, d, 14.9 Hz), 6.98 (1H, d, 14.8 Hz), 6.60 (1H, t, 5.1 Hz), 4.10-4.12 (2H, dd, 5.3, 2.6 Hz), 2.45 (3H, s), 2.23 (1H, t, 2.6 Hz); $^{13}$C NMR (126 MHz, CDCl3) δ 161.70, 145.60, 141.00, 135.58, 132.38, 130.25, 128.23, 78.28, 72.39, 29.77, 21.72.

HR-MS: observed $[M-H]^-$ 262.0537 (calculated 262.0543).

Preparation of UBE2L3* (C17S, C137S), UBE2D3* (C21S, 107S, C111S) and UBE2N

Full-length E2s were cloned into the pET expression vectors downstream of an N-terminal Hisx6 tag and Precision protease site. E. coli strain BL21(DE3) transformed with E2 clones were cultured at 37° C. in LB medium supplemented with 100 µg mL$^{-1}$ of ampicillin. When the $OD_{600}$ reached 0.6, the culture was induced by addition of 0.4 mM isopropyl thio-β-D-galactoside (IPTG) and incubated at 37° C. for 5.0 hours. The cells were harvested by centrifugation and stored at −80° C. Cells were resuspended in ice cold lysis buffer (50 mM Tris-HCl pH 7.5, 150 mM NaCl, 25 mM imidazole, 0.5 mg/mL lysozyme, 50 µg/mL Dnasel, Complete, Mini, EDTA-free protease inhibitor cocktail, (one tablet per 50 mL of buffer, Roche)) and incubated on ice for 30 minutes followed by sonication. The lysate was then clarified by centrifugation and the supernatant was subjected to Ni-NTA affinity chromatography (Qiagen) and washed with wash buffer (50 mM Tris-HCl pH 7.5, 150 mM NaCl, 25 mM imidazole). Protein was eluted with elution buffer (50 mM Tris-HCl pH 7.5, 150 mM NaCl, 300 mM imidazole) and dialyzed into storage buffer (20 mM Tris, 150 mM NaCl, 1 mM DTT). The protein was then further purified by size exclusion chromatography using a HiLoad 16/600 Superdex 75 pg column (GE Life Sciences) coupled to an ÄKTA Purifier FPLC system (1.0 ml min$^{-1}$, running buffer: 20 mM Tris-HCl pH 7.5, 150 mM NaCl, 1 mM DTT). Fractions were collected, concentrated and flash frozen for storage at −80° C.

General Method for DUB-SR Preparation

A plasmid composed of full-length Ub cloned into the pTXB1 vector (ref. 4) was taken and the bases coding for the C-terminal Ub residues 74-76 were deleted by Quikchange mutagenesis. To suppress cellular intein activity, a T3C mutation in the GyrA intein was also introduced yielding plasmid pTXB1-Ubd74-76-T3C. ER2566 E. coli cells (50 µL)(NEB) were transformed with pTXB1-Ubd74-76-T3C and recovered with S.O.C medium (250 µL). The cells were incubated for 1 h at 37° C. and then LB medium (150 mL) containing ampicillin (100 µg mL$^{-1}$) was inoculated with the recovered cells (300 µL) and the culture was incubated overnight with shaking (200 rpm) at 37° C. LB medium (3 L) containing ampicillin (100 µg mL$^{-1}$) was inoculated with the overnight culture (150 mL) and incubated with shaking (200 rpm) at 37° C. At $OD_{600}$ ~0.4, the cells were transferred to 25° C. incubator and after 30 min the cells were induced with IPTG (0.2 mM). After 5 h the cells were harvested and suspended in 90 ml lysis buffer (20 mM $Na_2HPO_4$ pH 7.2, 200 mM NaCl, 1 mM EDTA) and frozen. The thawed cells were lysed by sonication on ice and were clarified by centrifugation (13,000 rpm, 30 min). An empty XK 26/20 column (GE Life Sciences) was filled with chitin beads (30 mL) (NEB) and equilibrated with lysis buffer. At 4° C. the clarified lysate was loaded (flow rate: 1.0 mL min$^{-1}$) onto the column using an ÄKTA FPLC system. The column was then washed with lysis buffer (~600 mL) and equilibrated with 60 mL of cleavage buffer (20 mM $Na_2HPO_4$, pH 6.0, 200 mM NaCl, 1.0 mM EDTA, 100 mM Sodium 2-mercaptoethanesulfonate). The flow was then stopped and the column incubated for 48 hours at 4° C. to allow S-N transfer and concomitant thiolysis. Liberated ΔUb-SR was eluted with elution buffer (20 mM $Na_2HPO_4$, 200 mM NaCl, 1.0 mM EDTA, pH 6.0). The fractions containing ΔUb-SR were pooled and concentrated to ~3.0 mL using an Amicon Ultra-15 centrifugal filter device (Millipore). The protein was then further purified by semi-preparative RP-HPLC (Column: BioBasic-4; Part number: #72305-259270) using the Dionex system. A gradient of 10% buffer A to 80% buffer B was applied at a flow rate of 10 mL min$^{-1}$ over 30 min (buffer A=0.1% TFA in $H_2O$, buffer B=0.1% TFA in acetonitrile). Fractions containing ΔUb-SR were pooled and lyophilized yielding ~30 mg.

ΔUB-$N_3$ Aminolysis Reaction

ΔUb-SR (25.8 mg) was reconstituted (ref. 5) by the addition of DMSO (200 µL). On complete dissolution of ΔUb-SR in DMSO, $H_2O$ (800 µL) was added to give a final DMSO concentration of 20% (v/v). 500 µL of 2-azidoethanamine (Enamine) in 50% (v/v) aqueous DMSO/MQ (8 M) was then added to the ΔUb-SR solution. 60.0 µl of triethylamine (TEA) was then added raising the solution pH to 9 and the mixture was then briefly vortexed. The resulting solution was incubated at 30° C. for 16 hours and monitored by LC-MS. The protein (ΔUb-$N_3$) was then further purified by semi-preparative RP-HPLC (Column: BioBasic-4; Part number: 72305-259270) using the Dionex system. A gradient of 20% buffer A to 50% buffer B was applied at a flow rate of 10 mL min$^{-1}$ over 60 min (buffer A=0.1% TFA in $H_2O$, buffer B=0.1% TFA in acetonitrile). Fractions containing ΔUb-$N_3$ were pooled and lyophilized (Yield: 80%).

Conjugation of ΔUb-$N_3$ with TDAE by CuAAC Click Reaction

ΔUb-$N_3$ (3.5 mg) was reconstituted by the addition of 100 µl DMSO. On complete dissolution of ΔUb-$N_3$ in DMSO, $H_2O$ (900 µL) was added to give a final DMSO concentration of 10% (v/v) and a final ΔUb-$N_3$ concentration of 418.6 µM.

Stock solutions of TDAEs 3 or 4 were prepared using DMSO (10 mM stock concentration). TDAEs 3 or 4 (200 µL, 10 mM stock) were then mixed with a pre-prepared DMSO/MQ solution (456.2 µL, 20% (v/v)). Phosphate buffer (50.0 µL, 100 mM $Na_2HPO_4$ pH 7.5, 150 mM NaCl) and ΔUb-$N_3$ stock solution (238.6 µL, 418.6 µM) were then subsequently added. Tris(3-hydroxypropyltriazolylmethyl) amine (THPTA) in $H_2O$ (25 µL, 12.5 eq., 50 mM stock solution) was pre-mixed with a freshly prepared solution of $CuSO_4$ (aq.) (5 µL, 2.5 eq., 50 mM stock solution). The THPTA/$CuSO_4$ (aq.) solution (30 µL) was then added to the previously prepared TDAE/ΔUb-$N_3$ solution. L-ascorbic acid in $H_2O$ (25 µL, 100 mM stock solution) was then added to the previously mixed components. The reaction was incubated at 23° C. with shaking (1400 rpm) for 15 minutes. The reaction was then quenched by the addition of EDTA (2.5 mM final concentration) and the product (7 or 8) was purified by semi-preparative RP-HPLC (Column: BioBasic-4; Part number: 72305-259270) using the Dionex system. A gradient of 20% buffer A to 50% buffer B was applied at a flow rate of 10 mL min$^{-1}$ over 60 minutes (buffer A=0.1% TFA in $H_2O$, buffer B=0.1% TFA in acetonitrile). Fractions containing ΔUb-TDAE were pooled and lyophilized (Yield: 60%).

Synthesis E2~UB Probes 9, 10, 11 and 12

ΔUb-TDAE (7.0 mg) was reconstituted by the addition of 50 µl DMSO. On complete dissolution of ΔUb-TDAE, $H_2O$ (450 µL) was added to give a final DMSO concentration of 10% (v/v) and a final ΔUb-TDAE concentration of 1.6 mM. ΔUb-TDAE was then incubated with 0.5 eq. of the desired E2 in 0.8 ml phosphate buffer (100 mM $Na_2HPO_4$ pH 7.5, 150 mM NaCl, reducing agent free) at 23° C. for two hours and monitored by LC-MS. For probe 10 synthesis, additional 30° C. overnight incubation was required to consistently achieve quantitative elimination to the unsaturated AVS species. The product was purified by gel filtration (0.5 mL min$^{-1}$, 20 mM Tris-HCl pH 7.5, 150 mM NaCl as mobile buffer, HiLoad 16/600 Superdex 75pg).

Molecular Modelling of RING- and HECT-Probe Complexes

The RING-E2-Ub model was generated by importing the PDB 4AP4 into the BioLuminate biologics modelling suite (Schrödinger). The AVS-triazole linker present between E2 and Ub in probe 10 was manually built and geometry optimized. Hydrogen atoms were then added using the Protein Preparation tool. E2 Cys85, Ub Leu73, and the linkage between them were selected along with all protein residues within 5 Å. This substructure was then energy minimized using the OPLS2005 forcefield. Minimized coordinates were then exported as mol2 files and imported into Pymol (Schrödinger) for figure generation. The same procedure was repeated for the HECT-E2-Ub model using PDB 3JW0.

Parkin Activity Assay with UBE2L3*

Parkin (3 µg, 760 nM) was incubated with ubiquitylation assay components in a final volume of 50 µl (50 mM Tris-HCl pH 7.5, 5 mM $MgCl_2$, 240 nM UBA1, 2 µM UBE2L3 variant, 2 mM ATP, 58 µM Ub and 380 nM of GST-PhPINK1 WT. The reaction was incubated at 30° C. for 1 h. The reaction was quenched by the addition of reducing 4× LDS loading buffer. The reaction mixture was resolved by SDS-PAGE and visualized by coomassie staining.

Preparation of UBE2L3-ProcK3

An amber stop codon was introduced at position 3 of the open reading frame in pET156-UBE2L3* by Quikchange site-directed mutagenesis. This yielded the plasmid pET156-UBE2L3*-TAG3 (* corresponds to a C17S and C137S mutant). BL21 (DE3) cells (Merck Biosciences) were transformed with plasmids pET156-UBE2L3*-TAG3 and pCDF-PylST (plasmid harbouring constitutive copies of the Mb PylRS and Mb Pyl-tRNA$_{CUA}$, a kind gift from Dr. Jason Chin) and used to inoculate 200 ml LB media containing ampicillin (100 µg ml$^{-1}$) and spectinomycin (50 µg mL$^{-1}$). After overnight incubation at 37° C., 200 rpm, 6×1 L of LB medium containing ampicillin (100 µg ml$^{-1}$) and spectinomycin (25 µg mL$^{-1}$) were each inoculated with 30 mL overnight culture and incubated at 37° C., 200 rpm, until cell density reached $OD_{600}$=0.8-0.9. Propargyloxycarbonyl-L-lysine (ProcK; Iris Biotech GmbH, #HAA2095) (300 mM stock solution in $H_2O$ and pH adjusted to ~7) was then added to a final concentration of 3 mM. Cultures were then incubated for a further 20 min at 37° C. and then induced with IPTG (500 µM). After 4 h cells were harvested by centrifugation at 4200 rpm, 30 min at 4° C. Cell pellets from 6 L culture were resuspended in 200 ml lysis buffer (50 mM Tris-HCl pH 7.5, 150 mM NaCl, 25 mM imidazole, 0.5 mg mL$^{-1}$ lysozyme, 50 µL ml$^{-1}$ Dnasel, 4 tablets of Complete, EDTA-free protease inhibitor cocktail (Roche) and incubated on ice for 30 min. The suspension was then sonicated before clarification at 18,000 rpm, 30 min at 4° C. Ni-NTA resin (600 µl of settled resin, Qiagen) was then added to the lysates and rotated at 4° C. for 1 h. Resin was then washed with wash buffer (50 mM Tris pH 7.5, 150 mM NaCl, 25 mM imidazole) and then eluted with elution buffer (50 mM Tris-HCl pH 7.5, 150 mM NaCl, 300 mM Imidazole). The eluate was then concentrated down to 2.5 mL and further purified by size exclusion chromatography using a HiLoad 16/600 Superdex 75 pg column (GE Life Sciences) coupled to an ÄKTA Purifier FPLC system (running buffer: 100 mM $Na_2HPO_4$ pH 8, 150 mM NaCl, 0.1 mM TCEP). Fractions were collected and concentrated (2.4 mg mL$^{-1}$, ~118 µM).

TAMRA Labelling of UBE2L3-ProcK3 by Copper-Catalyzed Azide-Alkyne Cycloaddition (CuAAC)

UBE2L3-ProcK3 was diluted in buffer (100 mM $Na_2HPO_4$ pH 8, 150 mM NaCl, 0.1 mM TCEP) to a final concentration of 50 µM. $CuSO_4$ and Tris(3-hydroxypropyl-triazolylmethyl)amine (THPTA) (ref. 6) stock solutions were freshly prepared in $H_2O$ and then premixed before being added to the protein at final concentrations of 0.1 mM and 1.0 mM, respectively. TAMRA-azide (Jena Bioscience, #CLK-FA008, M.W.=512.56 g mol$^{-1}$) was then added to a final concentration of 150 µM. Ascorbic acid was added to a final concentration of 4 mM. The reaction was incubated at 23° C. for 1-2 h (or until starting material had been consumed as determined by LC-MS). The reaction was then quenched with 5 mM EDTA for 15 min at 23° C. Small molecule components were then removed by dialysis against 2×1L buffer (100 mM $Na_2HPO_4$ pH 8.0, 150 mM NaCl, 5 mM EDTA, 0.1 mM TCEP) at 4° C. over 48 h. Protein was snap frozen in liquid nitrogen and stored at −80° C.

Cell Culture and Lysis Protocol

Flp-In T-Rex HeLa stable cell lines (HeLa cells stably expressing untagged Parkin WT, S65A, C431 F or H302A) were cultured (37° C., 10% $CO_2$) in Dulbecco's Modified Eagle Medium (DMEM) supplemented with 10% (v/v) Fetal Bovine Serum (FBS), 2.0 mM L-glutamine, 1× minimum essential medium (MEM, Life Technologies), 1× non-essential amino acids (NEAA, Life Technologies), 1.0 mM of sodium pyruvate (Life Technologies) and antibiotics (100 units/mL penicillin, 0.1 mg/mL streptomycin). At 80% confluency cells were either untreated or treated with 10 µM CCCP, and incubated for a further 3 h. Cells were rinsed with ice-cold PBS and extracted in lysis buffer (50 mM Tris-HCl pH 7.5, 1.0 mM EGTA, 1.0 mM EDTA, 0.27 M sucrose, 10 mM sodium 2-glycerophosphate, 0.2 mM phenylmethane sulfonyl fluoride (PMSF), 1.0 mM benzamidine, 1.0 mM sodium ortho-vanadate, 50 mM sodium fluoride and 5.0 mM sodium pyrophosphate). Lysis was carried out by sonication (Sonic & Materials INC, VC 100, Jencons Scientific LTD, CT, USA, 55% amplitude, 12 times (1 sec on, 1 sec off)) and then clarified by centrifugation at 4° C. for 30 min at 14,800 rpm. Supernatants were collected (total cell extracts) and protein concentration determined by Bradford assay.

SH-SY5Y cells were grown in DMEM/F-12 media supplemented with 15% (v/v) FBS, 2.0 mM L-glutamine and antibiotics (100 units mL$^{-1}$ penicillin, 100 µg mL$^{-1}$ streptomycin).

To depolarize mitochondria, cells were treated with 10 µM Carbonyl cyanide m-chlorophenyl hydrazine (CCCP), dissolved in DMSO, for the indicated time. Cell extracts were prepared as described for HeLa cells. All cells were cultured at 37° C. in a 5% $CO_2$ humidified atmosphere.

In Vitro Probe-Labeling Assay

The indicated E3 ligases were added into Tris buffer (20 mM Tris-HCl pH 7.5, 150 mM NaCl) with 1.0 mM TCEP. 5.0 e.q (unless otherwise indicated) of E2-Ub (probe 9 or 10) was incubated with E3 ligase at 30° C. for the indicated time. Reactions were quenched by the addition of 4×LDS loading buffer (supplemented with ~680 mM 2-mercaptoethanol) and samples were analyzed by SDS-PAGE (4-12% NuPage gel) followed by coomassie staining or immunoblotting.

Ubiquitination Assay and In Situ Profiling

Parkin (1.3 µM) was incubated with ubiquitylation assay components in a final volume of 30 µl (50 mM Tris-HCl pH 7.5, 5 mM $MgCl_2$, 0.12 µM UBA1, 2 µM UBE2L3, 0.83 µM His-SUMO-Miro1, 2 mM ATP, 88 µM Flag-ubiquitin and 0.31 µM TcPINK1 (Tc, WT/KD). Ubiquitylation reactions were incubated at 30° C. and 1050 rpm for 60 min. Ubiquitylation reactions were stopped by the addition of 5 U ml$^{-1}$ Apyrase (New England BioLabs) and incubated for 10 min at 30° C. and 1050 rpm. Probe profiling was carried out by the addition of 9 or 11 (8 µM) and incubated for 10 h at 30° C. and 650 rpm. The reactions were terminated by the addition of LDS sample buffer containing 4% 2-mercaptoethanol. Reaction mixtures were resolved by SDS-PAGE and immunoblotted with the following antibodies: anti-FLAG (Sigma, 1:10000), anti-Parkin (Santa-Cruz, 1:500) or anti-His (1:5000). For Fluorescence detection, 20 µl of sample were loaded on a 4-12% gel and subjected to SDS-PAGE. Gels were washed with water for 30 minutes and then visualized by scanning with a FLA-5100 imaging system (Filter: LPG, Laser: 532 nm, Voltage: 400, FUJIFILM Life Science). The gel was subsequently coomassie stained.

DUB Resistance Assay

His-USP2$_{259-605}$, His-USP21$_{196-565}$, OTUB2 and GST-UCHL3 were expressed in E. coli and purified. The DUB-reactive ubiquitin-based probe, Ub-Alk, was used as a positive control and tested in parallel with probes 9 and 10. Probes were diluted to 40 µM and DUBs were diluted to 10 µM in buffer (20 mM Tris-HCl pH 7.5, 150 mM NaCl, 1 mM TCEP). Probe (10 µL) and DUB (10 µL) solutions were then mixed and incubated for 2 h at 30° C. Proteins were then resolved by SDS-PAGE and visualized by coomassie staining.

Tryptic MS/MS Sequencing of Crosslinked Peptides from Parkin and 9

The coomassie stained SDS-PAGE band corresponding to the probe 9 labeled Parkin was excised and dehydrated and resuspended using standard procedures. LC-MS/MS analysis was performed on an LTQ Orbitrap Velos instrument (Thermo Scientific) coupled to an Ultimate nanoflow HPLC system (Dionex). A gradient running from 3% solvent A to 60% solvent B over 45 min was applied (solvent A=0.1% formic acid in H$_2$O; solvent B=0.08% formic acid in 80% MeCN). Fragment ions were generated by CID and 1+ and 2+ precursor ions were excluded. Thermo raw data was converted to .mgf format using the MSConvert software (ProteoWizard). Raw data was searched using the pLink software against UBE2L3* and Parkin sequences with trypsin specificity with up to 3 missed cleavages. A cross-linker monoisotopic mass of 307.1644 was manually added which accounted for the theoretical mass difference associated with formation of a bisthioether between 2 Cys residues together with the acrylate AVS, the triazole linkage and the tryptic Leu73 remnant from the Ub C-terminus.

ABPP of Total Cell Extracts

E2-Ub probe (5.0 µM) was added to total cell extracts with 1.0 mM TCEP and Tris buffer (20 mM Tris-HCl pH 7.5, 150 mM NaCl) and then incubated at 30° C. for the indicated time. Reactions were quenched by the addition of 4×LDS loading buffer (supplemented with betamercaptoethanol) and samples were analyzed by SDS-PAGE (4-12% NuPage gel) followed by immunoblotting.

Immunoblotting

Samples were resolved by SDS-PAGE (4-12% NuPage gel, Invitrogen) with MOPS or MES running buffer (without boiling) and transferred on to 0.45 µm nitrocellulose membranes (GE Healthcare Life Science). Membranes were blocked with PBS-T buffer (PBS+0.1% Tween-20) containing 5% (w/v) non-fat dried skimmed milk powder (PBS-TM) at room temperature for 1 h. Membranes were subsequently probed with the indicated antibodies in PBS-T containing 5% (w/v) Bovine Serum Albumin (BSA) overnight at 4° C. Detection was performed using HRP-conjugated secondary antibodies in PBS-TM for 1 h at 23° C. ECL Prime substrate (GE Life Sciences) was used for visualization in accordance with the manufacturers protocol.

Antibodies

His-tagged species were probed with 1:10000 anti-His primary antibody (Clontech, cat number: 631212). Anti-Parkin mouse monoclonal was obtained from Santa Cruz (sc-32282) at 1:2000 dilution (HeLa and SH-SYSY samples); anti-Parkin phospho-serine 65 rabbit monoclonal antibody was obtained as previously described (ref. 7) and used at 1:2500 dilution. GAPDH (14C10) rabbit mAb (HRP Conjugate, Cell Signaling Technology) was used at 1:5000 dilution.

Parkin Disease Mutant In Vitro Profiling

The different recombinant Parkin mutants (ref. 8) (1.0 µM, 1.535 µg) were incubated with Pediculus humanus corporis PINK1 (PhPINK1) or kinase dead PhPINK1 (0.77 µg), TCEP (1.0 mM), ATP (1.0 mM) and Ub (75 µM) in 1×Tris buffer (50 mM Tris-HCl pH 7.5, 150 mM NaCl, 5.0 mM MgCl$_2$) at 30° C. for 1.0 h. After 1.0 hour incubation, fluorescent probe 13 was added (5.0 µM) and incubated for another 4 or 8 hours in the dark at 30° C. Reactions were quenched by the addition of 4×LDS loading buffer (supplemented with betamercaptoethanol) for the indicated time point and samples were resolved by SDS-PAGE (4-12% NuPage gel). Gels were washed with water for 30 minutes and then visualized by scanning with a FLA-5100 imaging system (Filter: LPG, Laser: 532 nm, Voltage: 400, FUJIFILM Life Science). Quantification was carried out using the Fiji software variant of ImageJ. After scanning, gels were also coomassie stained.

REFERENCES FOR THE FURTHER EXAMPLES MATERIALS AND METHODS

1. Plechanovova, A., Jaffray, E. G., Tatham, M. H., Naismith, J. H. & Hay, R. T. Structure of a RING E3 ligase and ubiquitin-loaded E2 primed for catalysis. Nature (2012). doi:10.1038/nature11376
2. Kamadurai, H. B. et al. Insights into ubiquitin transfer cascades from a structure of a UbcH5B~ubiquitin-HECT (NEDD4L) complex. Mol Cell 36, 1095-1102 (2009).
3. Dadova, J. et al. Vinylsulfonamide and acrylamide modification of DNA for cross-linking with proteins. Angew Chem Int Ed Engl 52, 10515-10518 (2013).
4. Virdee, S., Ye, Y., Nguyen, D. P., Komander, D. & Chin, J. W. Engineered diubiquitin synthesis reveals Lys29-isopeptide specificity of an OTU deubiquitinase. Nat. Chem. Biol. 6, 750-757 (2010).
5. Oualid, El, F. et al. Chemical synthesis of ubiquitin, ubiquitin-based probes, and diubiquitin. Angew Chem Int Ed Engl 49, 10149-10153 (2010).
6. Hong, V., Presolski, S. I., Ma, C. & Finn, M. G. Angew Chem Int Ed Engl 48, 9879-9883 (2009).
7. Kazlauskaite, A. et al. Binding to serine 65-phosphorylated ubiquitin primes Parkin for optimal PINK1-dependent phosphorylation and activation. EMBO reports 16, 939-954 (2015).
8. Kazlauskaite, A. et al. Phosphorylation of Parkin at Serine65 is essential for activation: elaboration of a Miro1 substrate-based assay of Parkin E3 ligase activity. Open Biol 4, 130213 (2014).

Results

To further profile HECT/RBR ligase activity, for example, the inventors looked to develop probes which included the Ub component in an E2-ubiquitin complex. The following experiments report a scalable and modular strategy for the preparation of reengineered E2~Ub conjugates that harbour an electrophile that is positioned using structural and mechanistic knowledge. The conjugates serve as ABPs that allow the profile the transthiolation activity of Parkin for example
Design of an Activity-Based Probe Based on E2-Ub We reasoned that an engineered E2~Ub conjugate that contained a mechanistically positioned electrophile would serve as an ABP for profiling the transthiolation activity of HECT/RBR E3 ligases. However, the development of such probes presents a number of protein engineering challenges. Firstly, the labile thioester linkage in E2~Ub needs to be rendered stable by using an appropriate non-hydrolyzable mimetic. A second challenge is the installation of an electrophile between the Ub and E2 protein conjugate. The electrophile must be appropriately positioned and kinetically tuned for specific covalent labelling of the active site cysteine of an RBR/HECT E3 in an activity-based manner. An additional consideration is that E3s function with numerous E2s and often the physiological E2-E3 pair is unknown[25,30]. Hence, a modular strategy that enables the production of probes built on recombinant E2s of choice would be desirable. Also, the probes should not cross-react with deubiquitinating enzymes or be hydrolyzed by their (iso)peptidase activity[31]. Furthermore, as such probes would be expected to be powerful structural tools enabling the stabilization of otherwise transient key enzyme intermediates, probe production in milligram quantities would also be highly desirable.

We reasoned that appending a tosyl-substituted doubly activated ene (TDAE)[29] to the C-terminus of Ub would generate a highly electrophilic, but thiol-specific, protein conjugate that could undergo addition-elimination with the catalytic cysteine residue of recombinant E2s allowing the production of a stable mimetic of E2~Ub harboring an electrophilic trap. To achieve this the TDAE would need to be rendered tri-functional by the incorporation of an additional, yet orthogonal, reactive handle. We reasoned that an alkyne moiety would satisfy this requirement (FIG. 5a). The Ub-TDAE conjugate could then be prepared by triazole formation between azide-functionalized Ub and alkyne-functionalized TDAEs using Copper-catalyzed Azide-Alkyne Cycloaddition (CuAAC)[32] (FIG. 5b).

Trifunctional TDAEs Enable Production of E2~Ub Conjugates Harboring Internal Electrophiles We designed and synthesized TDAEs 3 and 4 bearing alkyne functionality that would ultimately furnish E2~Ub conjugates harbouring thioacrylate and thio-acrylamide AVS electrophiles, respectively. Having complementary electrophiles has been shown to improve coverage of enzyme family members with other ABPs[33], and would also demonstrate generality of this strategy. TDAEs 3 and 4 were prepared by synthesis of the corresponding alkyne-functionalized ene building block[34], in the case of 4, followed by a Phl(OAc)2/KI-mediated reaction with sodium p-toluenesulfinate[35] (FIG. 5a). Upon, addition-elimination chemistry with a thiol, 3 and 4 would generate the desired AVS electrophiles[29].

Figure 6A:
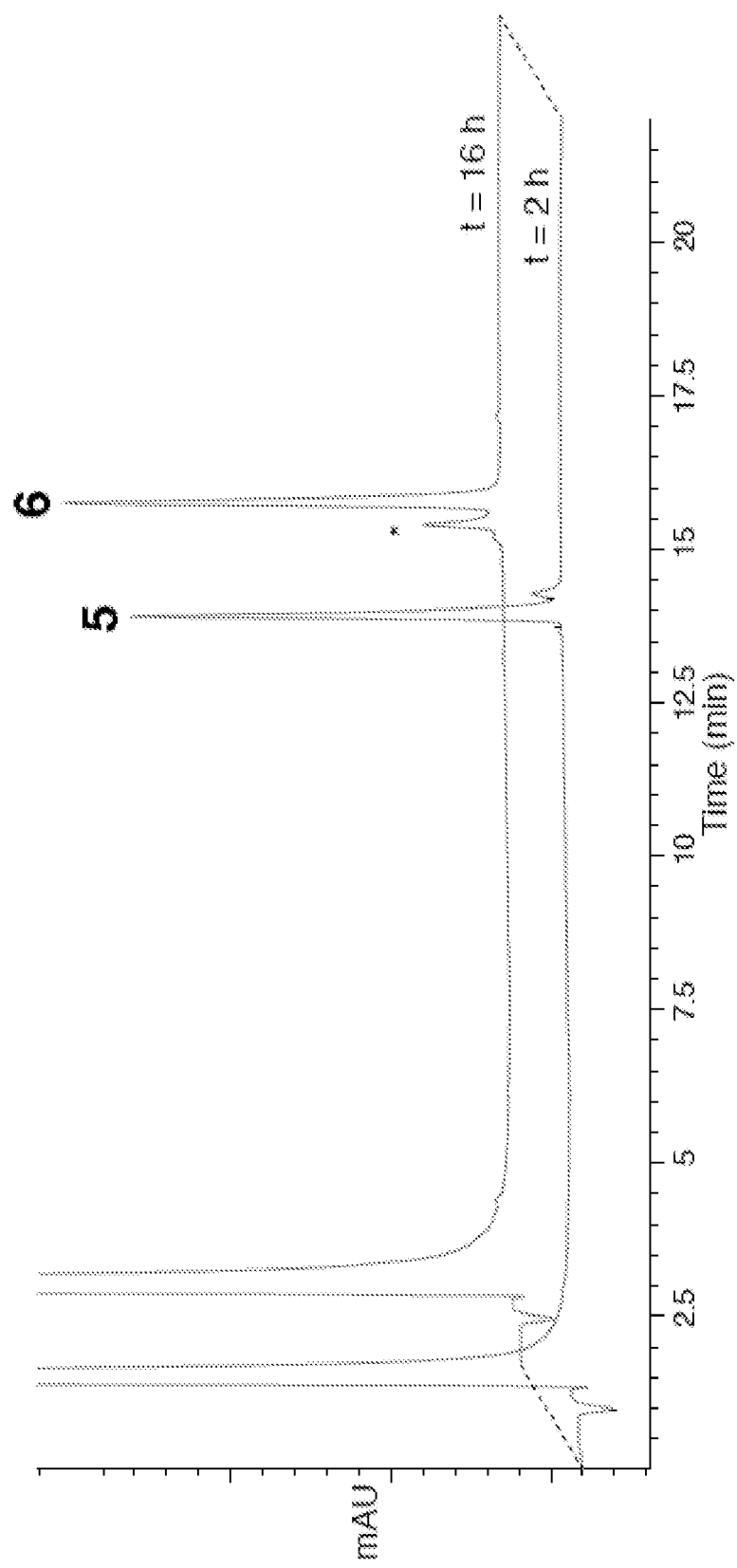
Figure 6A:
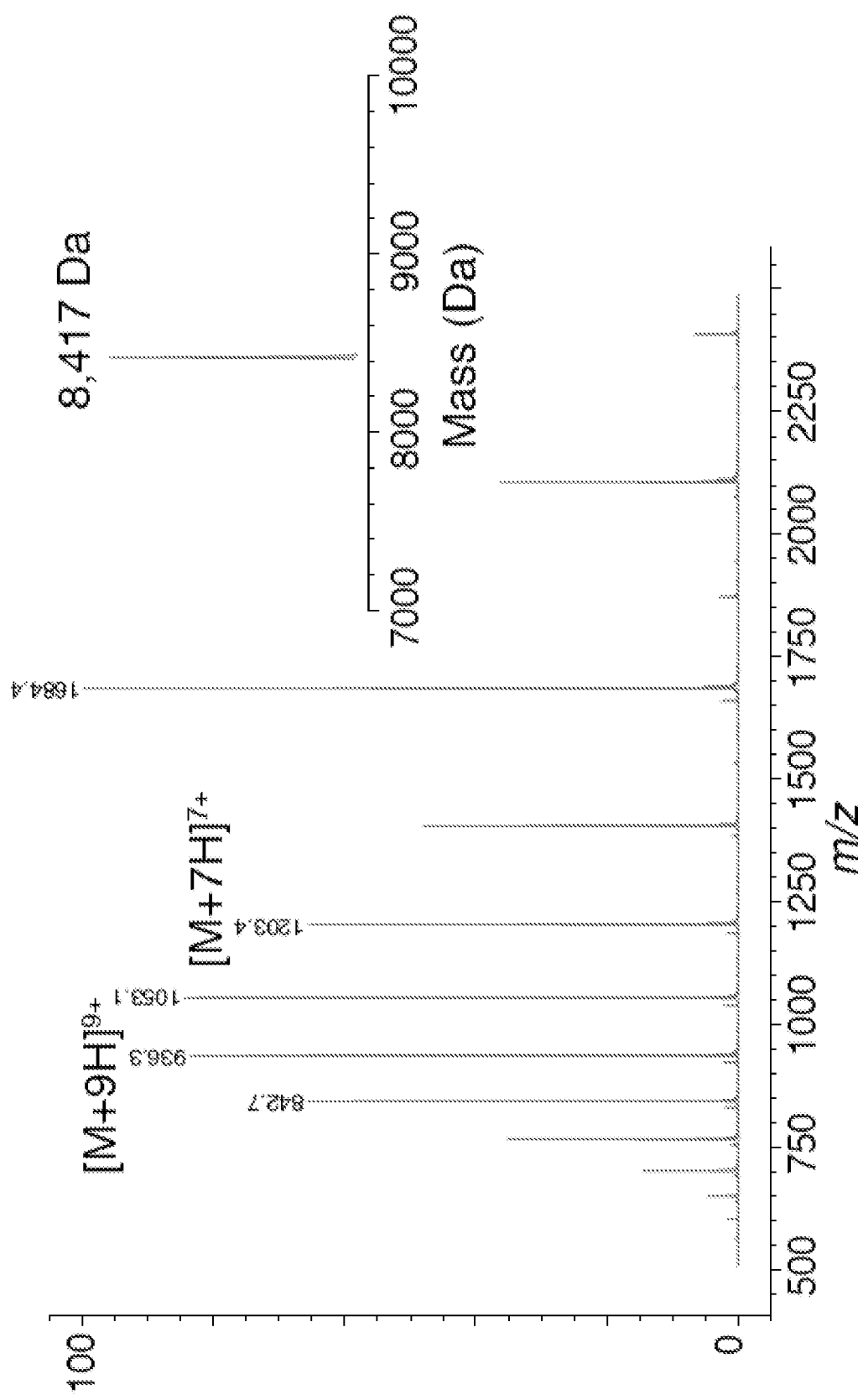
Figure 6B:
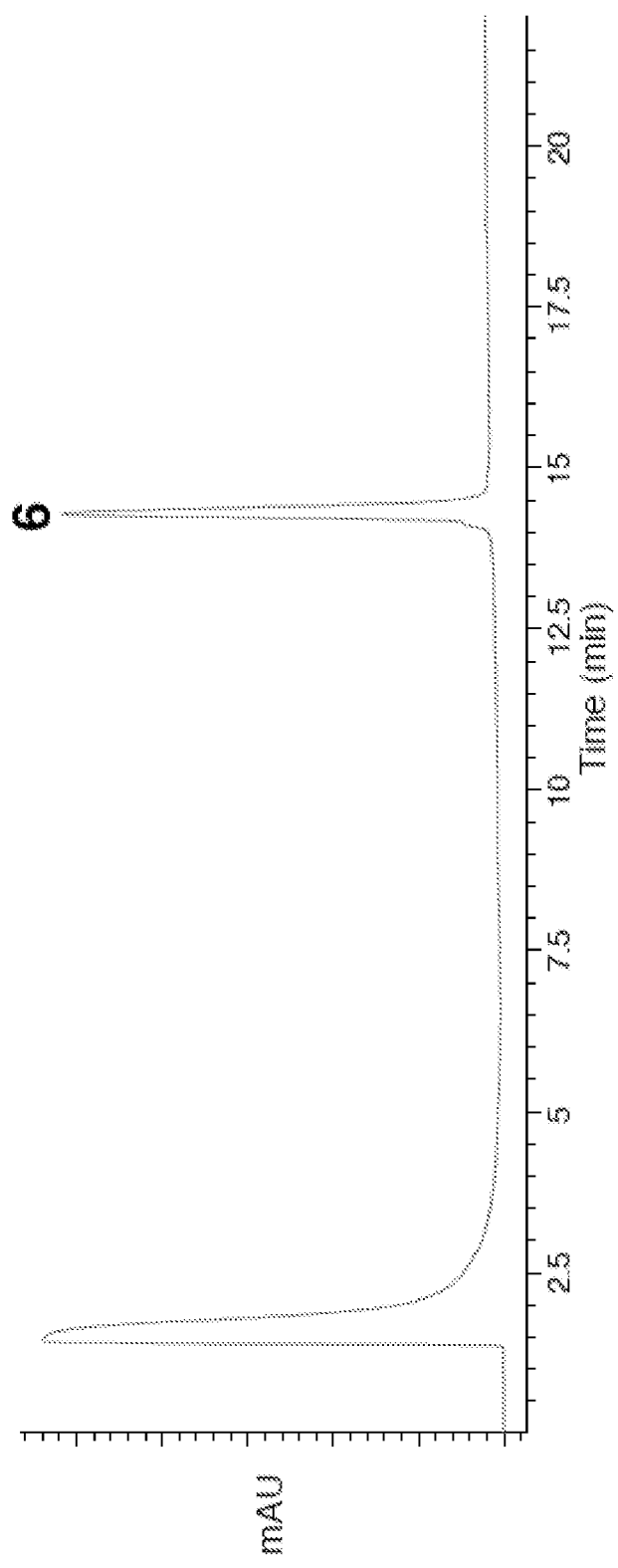
Figure 6B:
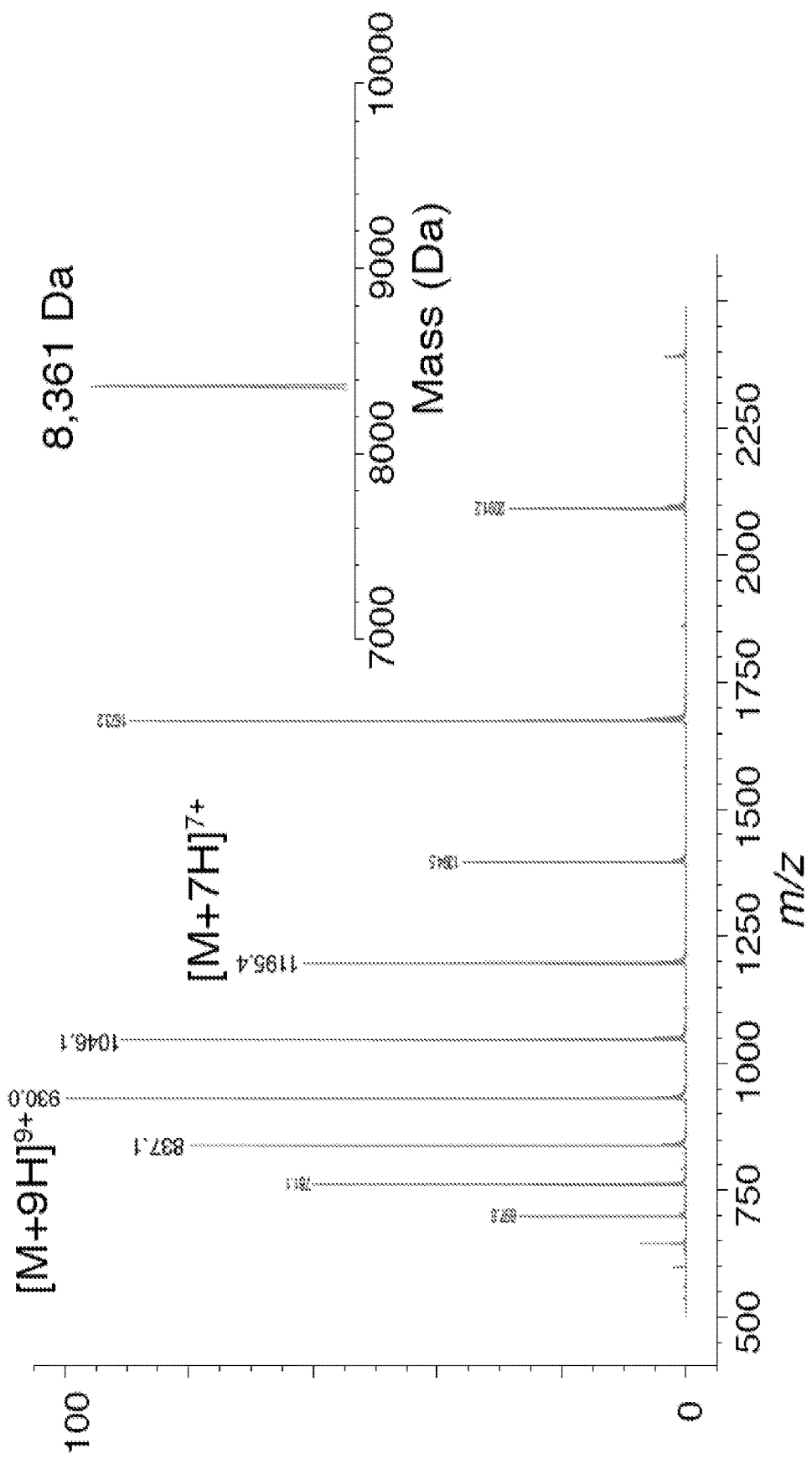
Figure 6C:
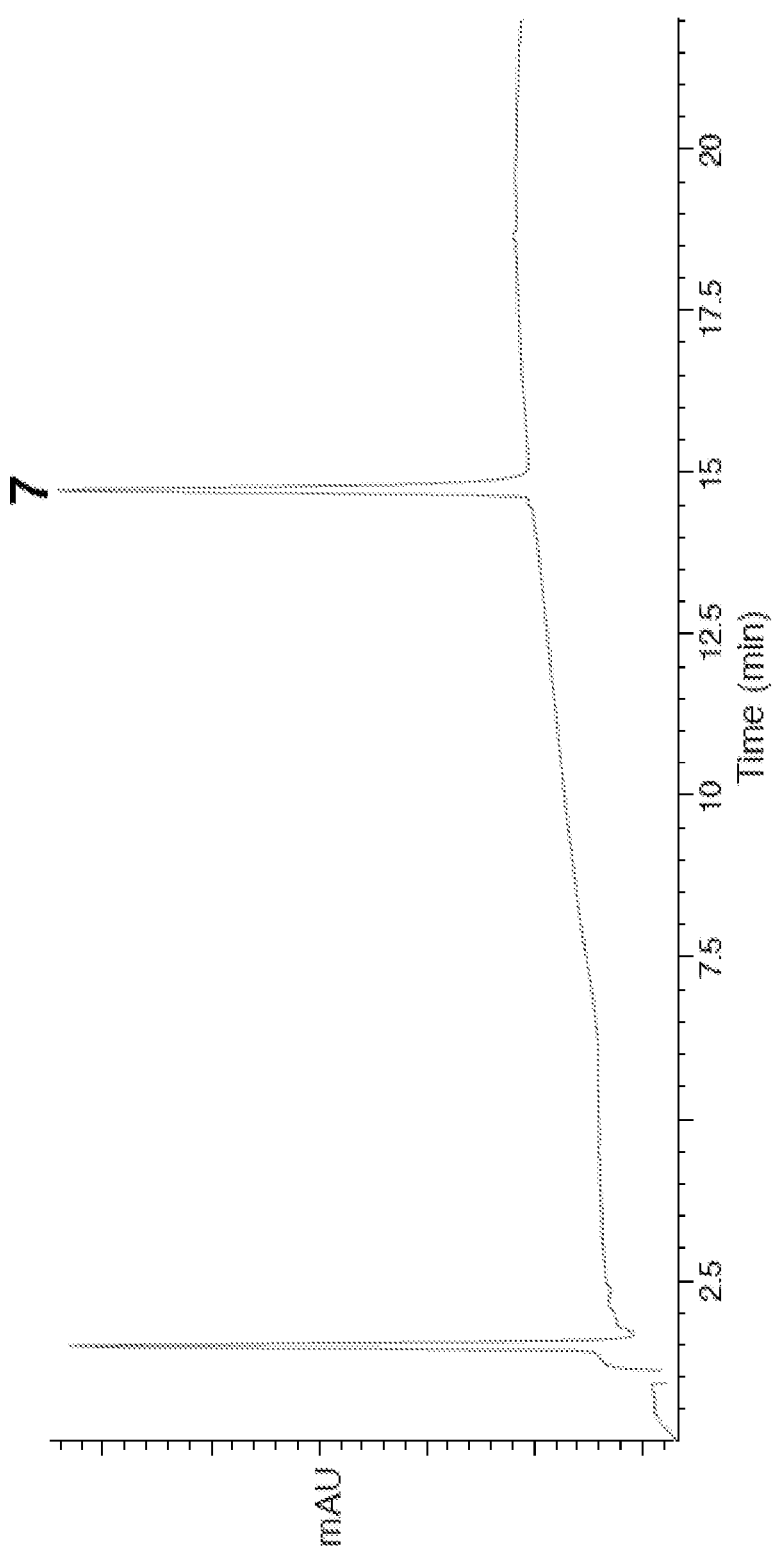
Figure 6C:
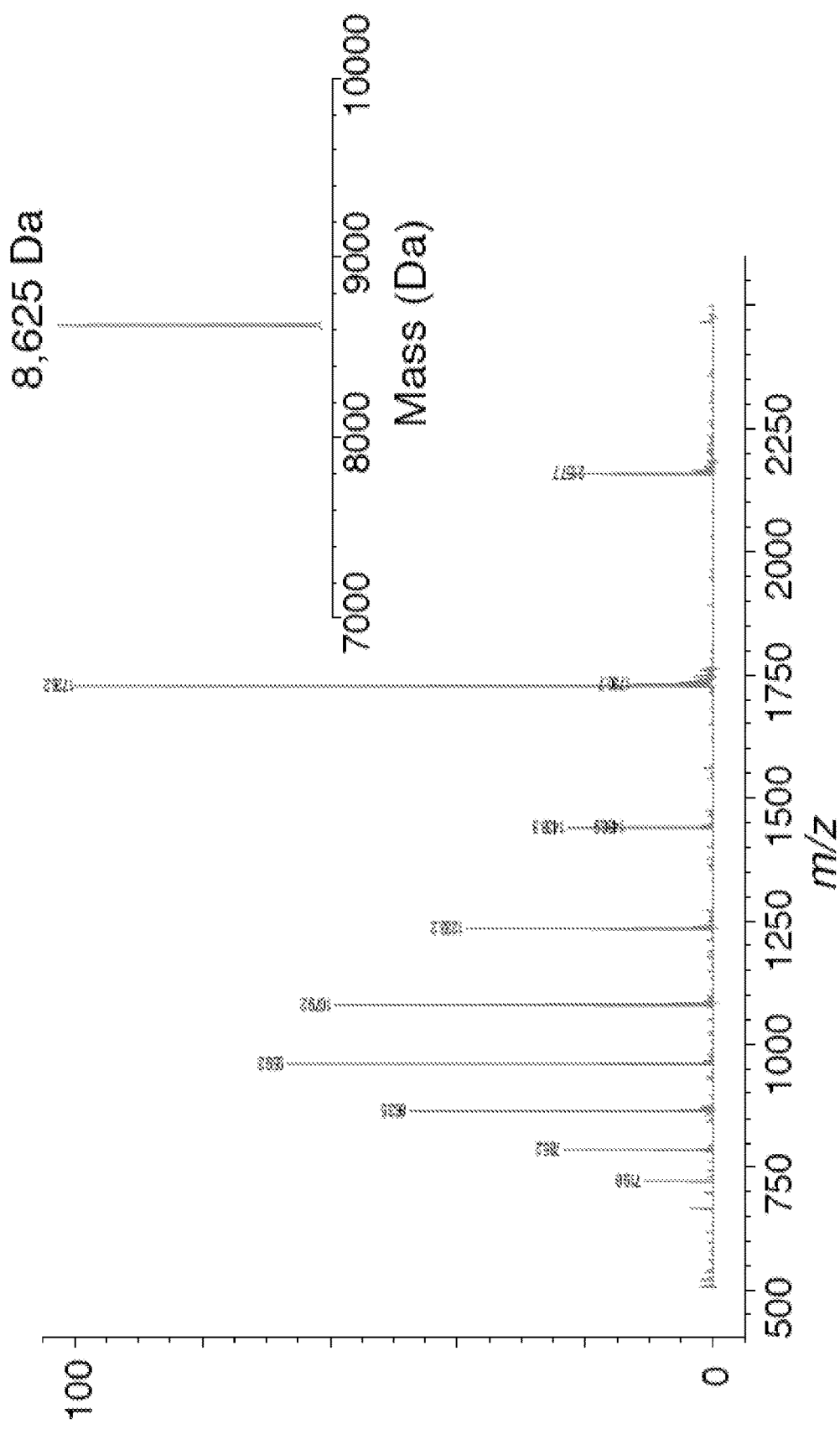
Figure 6D:
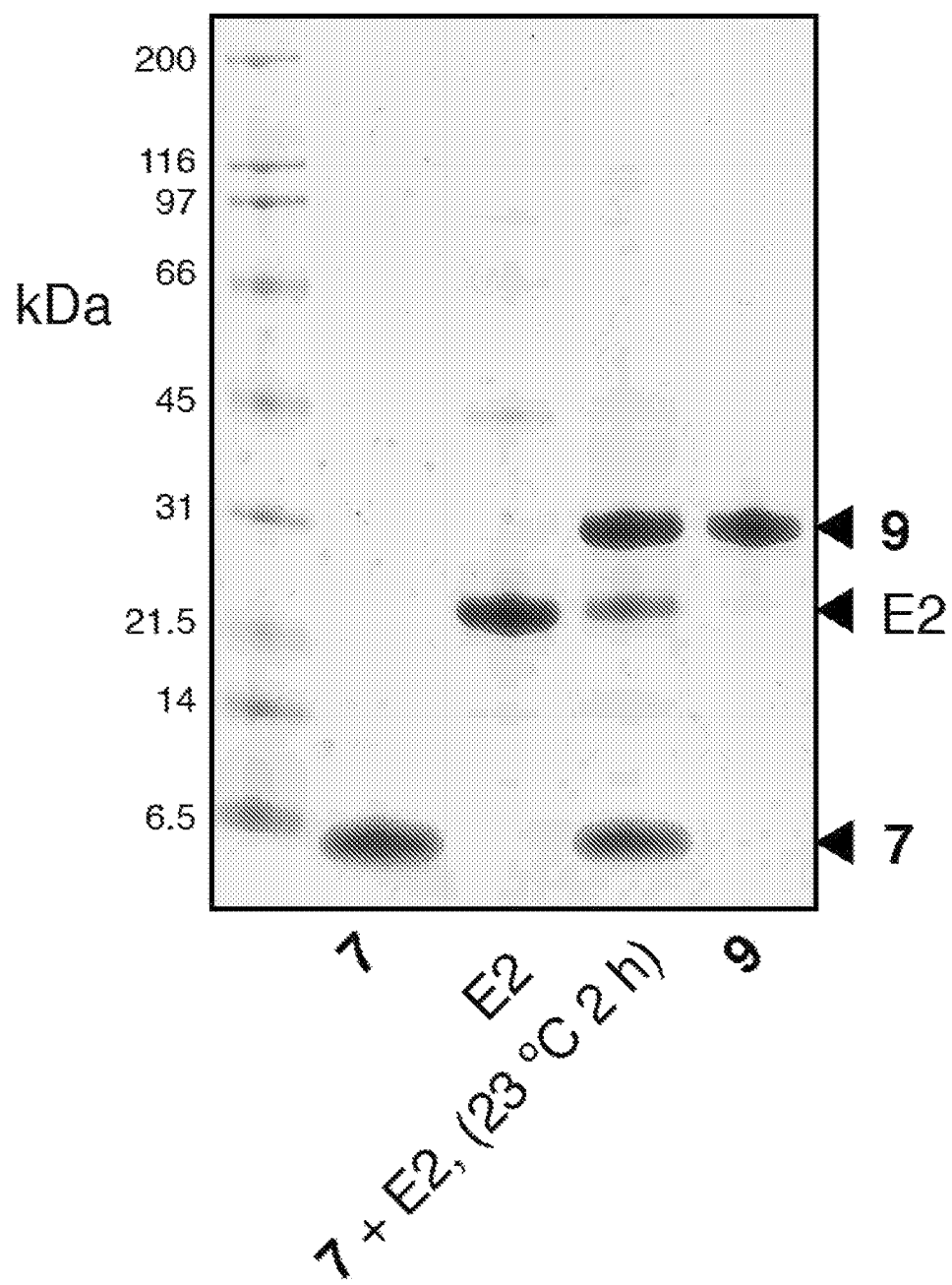
Figure 6E:
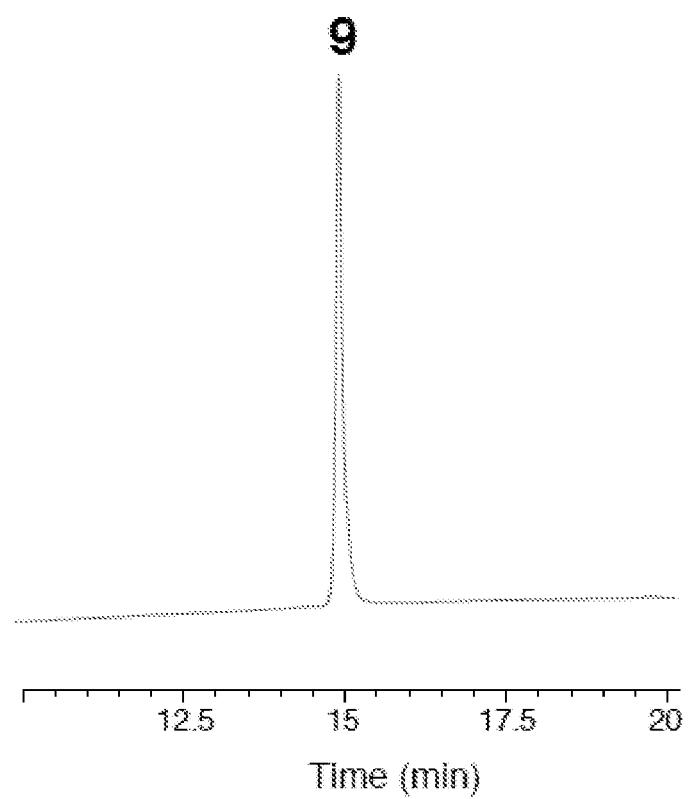
Figure 6E:
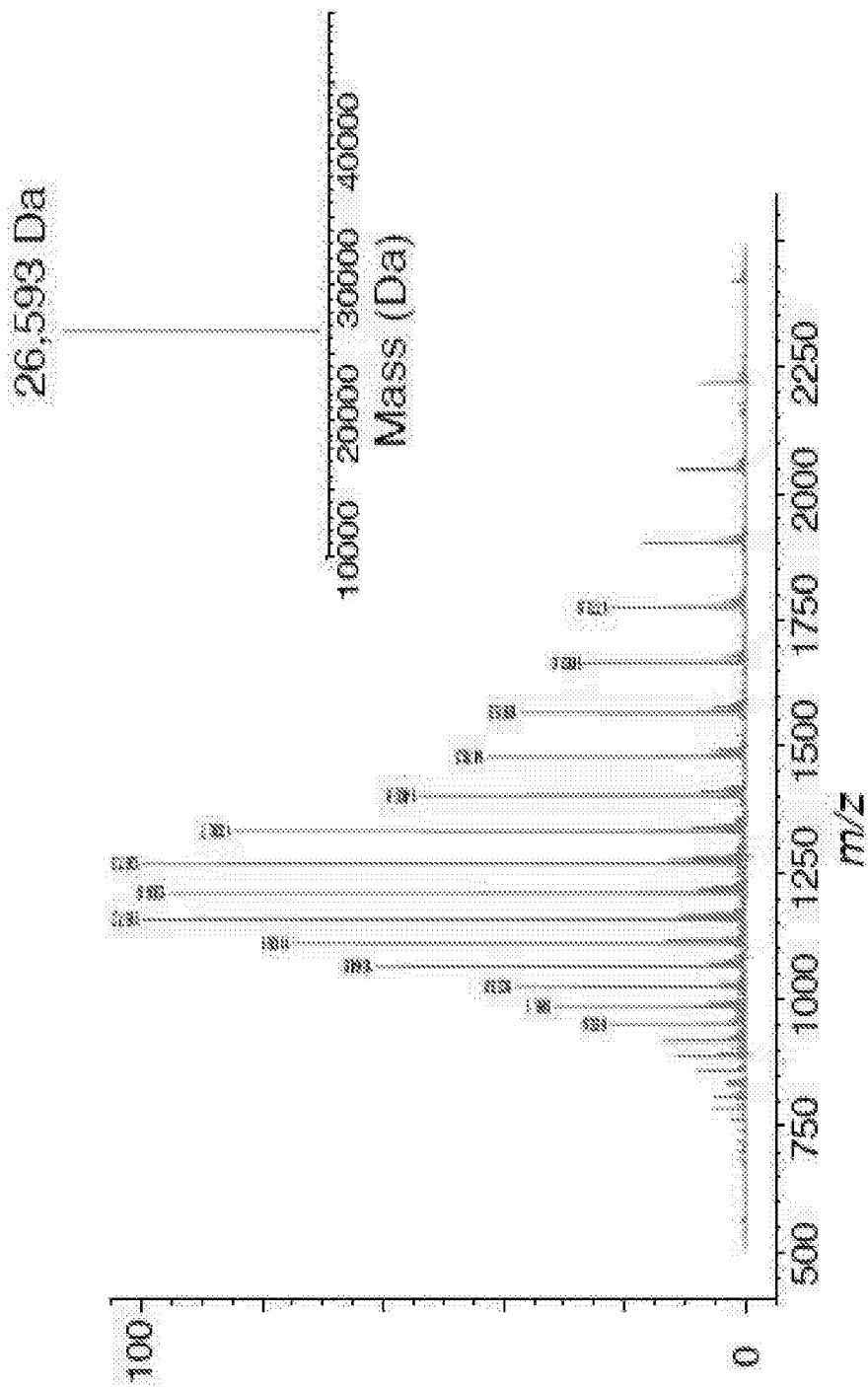

To generate azide-functionalized Ub we expressed Ub missing C-terminal residues 74-76 as a fusion with an engineered version of the GyrA intein to prevent cellular cleavage[36], and liberated Ub1-73 thioester 5 by thiolysis (FIG. 5b and FIG. 6a). A truncated Ub species was chosen as molecular modelling, based on RING-E2~Ub and HECT-E2~Ub co-crystal structures, indicated that the AVS-triazole linker would satisfactorily mimic the Ub C-terminus and serve as a surrogate for residues 74-76. Azide functionality was subsequently installed by an aminolysis reaction between 5 and azidoethanamine in 80% yield furnishing 6 (FIG. 5b and FIG. 6a). 6 was then conjugated to TDAEs 3 or 4 by CuAAC[32] and purified (60% yield) providing Ub-TDAE conjugates 7 and 8, respectively (FIG. 5b, and FIG. 6c). We then tested whether the rapid and chemoselective addition-elimination reaction observed between simple small molecule TDAEs and cysteine containing proteins under native conditions was preserved with Ub-TDAEs 7 and 8[29]. To ensure mono addition to an E2 we used a single cysteine mutant of UBE2L3 (UBE2L3*, also known as UbcH7)[29]. We found that UBE2L3* supported Parkin activity comparable to wild type enzyme. N-terminal tagging also did not affect apparent activity (FIG. 11). We found that UBE2L3* underwent efficient formation of E2~Ub conjugates in non-denaturing phosphate buffer at 23° C. within 2 h when reacted with 7 or 8 (FIG. 6d). The conjugates were further purified by size-exclusion chromatography (FIG. 6d). Liquid Chromatography-Mass Spectrometry (LC-MS) analysis revealed that in the case of 7, the anticipated elimination of p-toluene sulfinic acid (p-TolSO 2H) was observed[29], thereby generating an E2~Ub conjugate harboring an AVS electrophile primed for orthogonal thiol functionalization at precisely the same atomic center bonded to the E2 catalytic cysteine sulphur atom, probe 9 (FIG. 6e). Reaction efficiency was typically 95%. However, in the case of the reaction with 8, 16 h incubation at 30° C. was required to promote quantitative p-TolSO2H elimination, probe 10. This approach was readily compatible with other E2s as UBE2N (also known as Ubc13) also underwent efficient addition-elimination with 7.

Construction of a TAMRA Conjugated E2~Ub Probe

To increase the versatility of the probes we constructed derivatives built on UBE2L3* bearing a bio-orthogonal alkyne handle. This would allow the production of probes that could be conjugated to fluorescent reporter tags that would expedite protein profiling by enabling direct in-gel fluorescent scanning and grant access to other powerful ABPP methodologies reliant on probe fluorescence[37]. Affinity tags such as biotin could also be attached to allow enrichment of active enzymes and their identification/quantification by mass spectrometry[37]. To incorporate alkyne functionality into our probe we expressed UBE2L3* containing the amino acid propargyloxycarbonyl-L-lysine (ProcK)N-terminal to the Hisx6 purification/reporter tag in UBE2L3*, at position 3 (UBE2L3*-ProcK3). This was achieved by amber codon suppression in E. coli using the Methanosarcina barkeri pyrrolysyl tRNA-synthetase/tRNA CUA pair 48. Incorporation of ProcK was confirmed by LC-MS. Azide-functionalized 5-carboxytetramethylrhodamine (TAMRA) was then used to label UBE2L3*-ProcK3 by CuAAC yielding UBE2L3*-TAMRA.

Figure 6F:
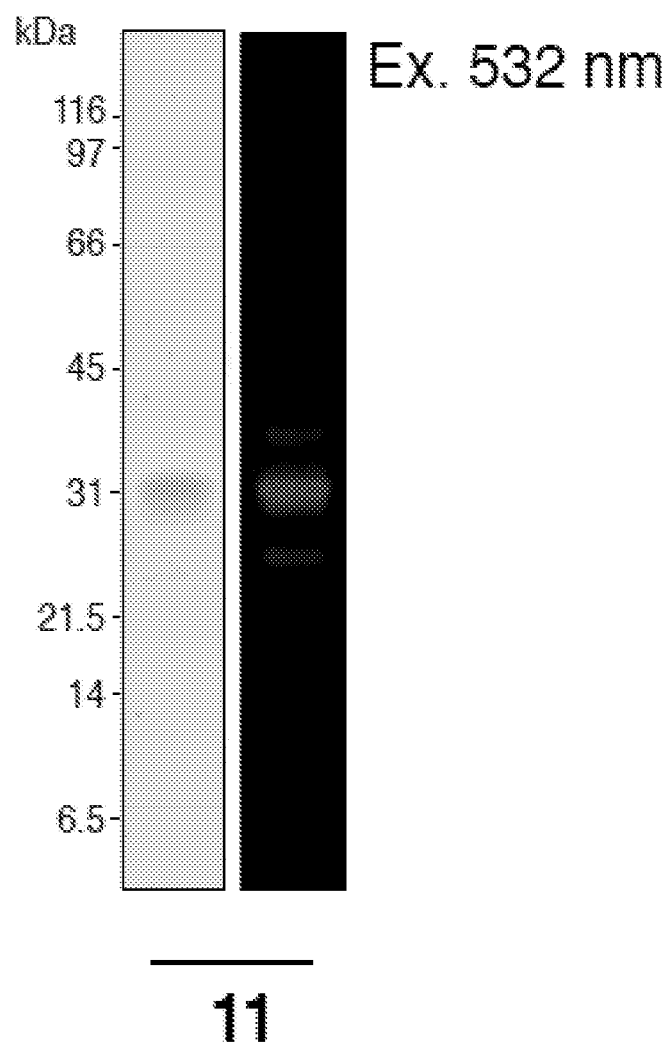

UBE2L3*-TAMRA was then reacted with Ub-TDAE conjugate 8 for 2 h at 23° C. The fluorescent conjugate was purified by size-exclusion chromatography and characterized by SDS-PAGE and LC-MS yielding fluorescent probe 11 (FIG. 6f).

It is expected that high affinity enrichment tags such as azide-functionalized biotin could also be conjugated to presently described probes allowing multiplexed profiling in combination with E3 ligase activity quantification and identification.

Another potential application of the probes described herein is as structural tools. There is a long-standing interest in the conformational changes and mechanistic aspects of Ub transfer throughout the Ub conjugation cascade. Key intermediates, such as transthiolation intermediates between E1-E2 and E2-E3, are inherently unstable yet define the mechanistic features of these important enzymes. Probe labelling of E3 produces a stable bisthioether cross-link between the ternary E2-Ub-E3 complex. A structural understanding of this intermediate is likely to decrypt the arcane multi-domain nature of RBR E3 ligases for example.

E2-Ub Probes Label Parkin in an Activity-Dependent Manner

Figure 7A:
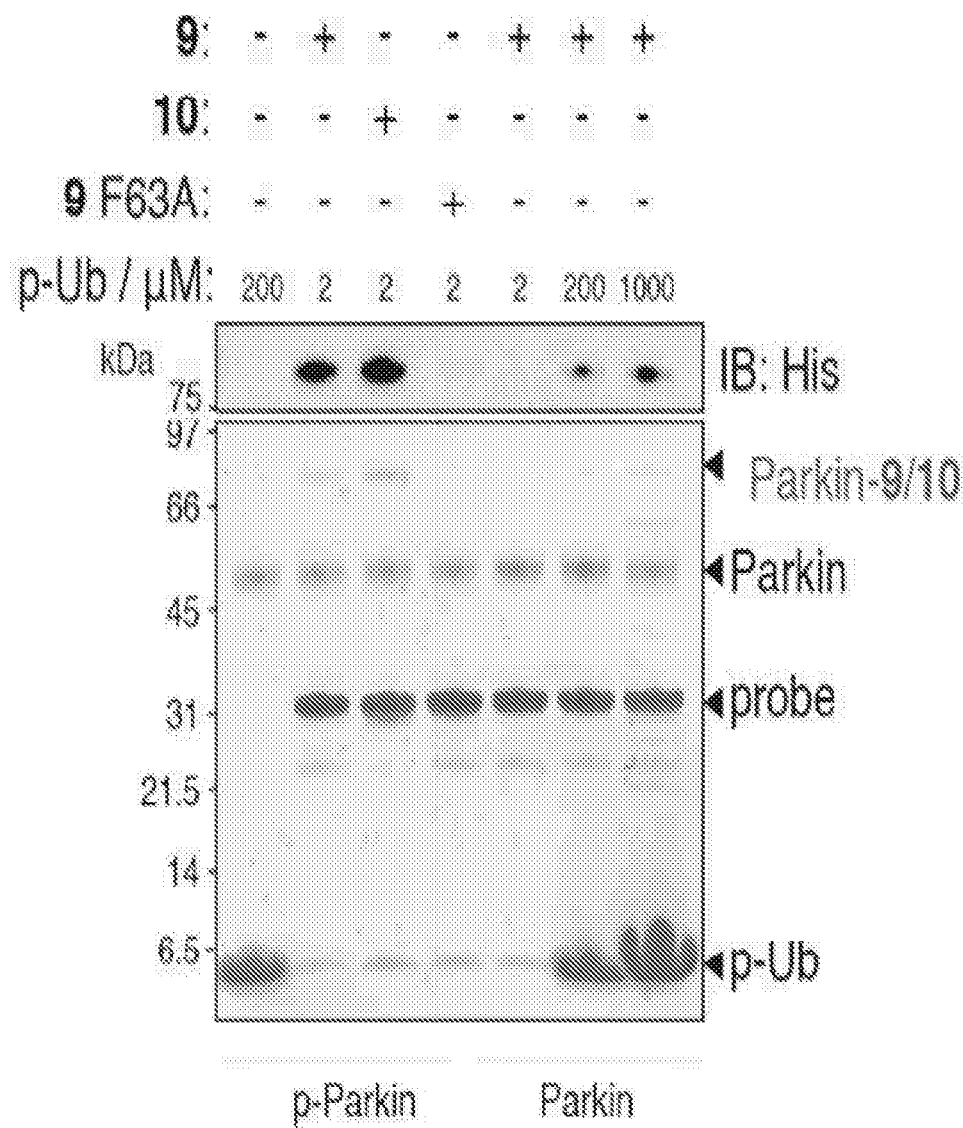

To validate our probes we profiled recombinant Parkin with probes 9 and 10. Since phosphorylation of Parkin and Ub have been demonstrated to maximally activate Parkin[26,21], we initially carried out experiments using Ser65-phosphorylated Parkin (p-Parkin) in the presence of Ser65-phosphorlyated-Ub (p-Ub). p-Parkin and p-Ub were prepared byincubation of Parkin and Ub with PINK1 and ATP and were purified by gel-filtration chromatography[27]. Phosphorylation of Ub was quantitative whilst phosphorylation of Parkin was ~60%, as determined by LC-MS and Phostag SDS-PAGE. We tested the thioacrylate and thioacrylamide electrophiles by observing the labelling efficiency of 9 and 10 against p-Parkin/p-Ub. Probe-treated samples were resolved by SDS-PAGE and then visualized by coomassie staining and immunoblotting against the Hisx6 purification/reporter tag on 9 and 10. This revealed that Parkin was labelled by both probes with 10 being moderately more efficient than 9 (FIG. 7a). This was attributable to increased electrophilicity of the acrylamide electrophile, to it being a closer mimic of the Ub C-terminus, or a combination of both. To confirm that probes 9 and 10 were being recruited to Parkin via E2 engagement 13, we built a mutant version of 9 (9 F63A) containing a Phe63Ala mutation in UBE2L3*.Phe63 has been shown to be essential for efficient binding of E2 to RING and HECT E3 ligases[38]. Consistent with this, we found that 9 F63A failed to label p-Parkin/p-Ub (FIG. 7a). We next assessed labelling of non-phosphorylated Parkin in the presence of p-Ub but did not observe labelling under initial test conditions (FIG. 7a). As non-phosphorylated Parkin has been shown to be activated with a molar excess of p-Ub 23, as inferred by qualitative in vitro polyubiquitin assembly assays, we tested whether labelling of Parkin with 9 could be achieved with elevated levels of p-Ub.Indeed, we began to observe Parkin labelling at 0.2 and 1 mM p-Ub concentrations and labelling efficiency was concentration-dependent (FIG. 7a).

Figure 7B:
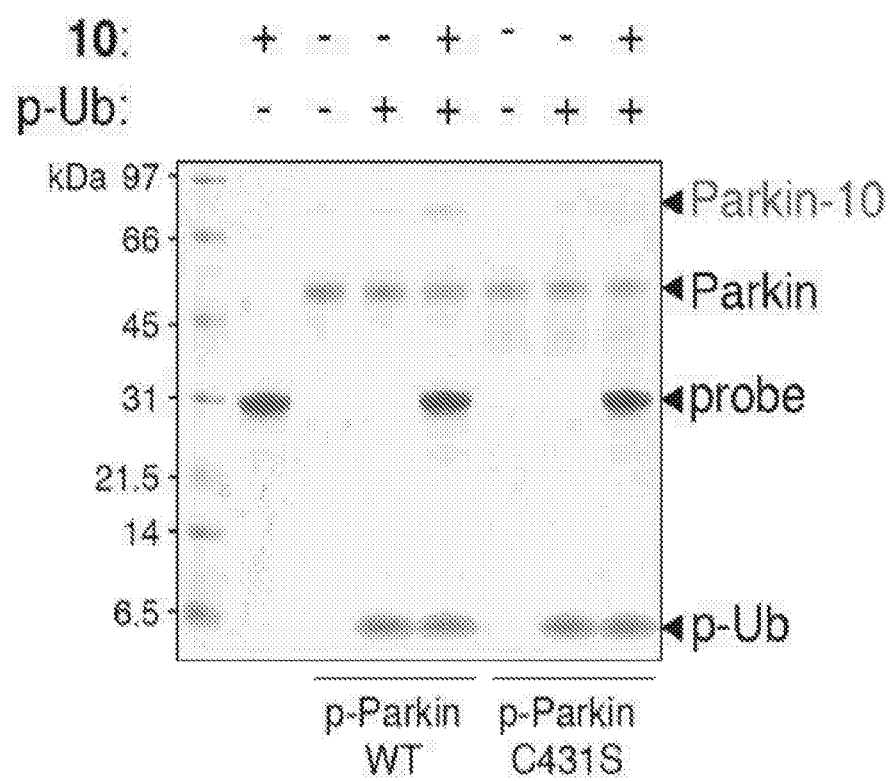
Figure 7C:
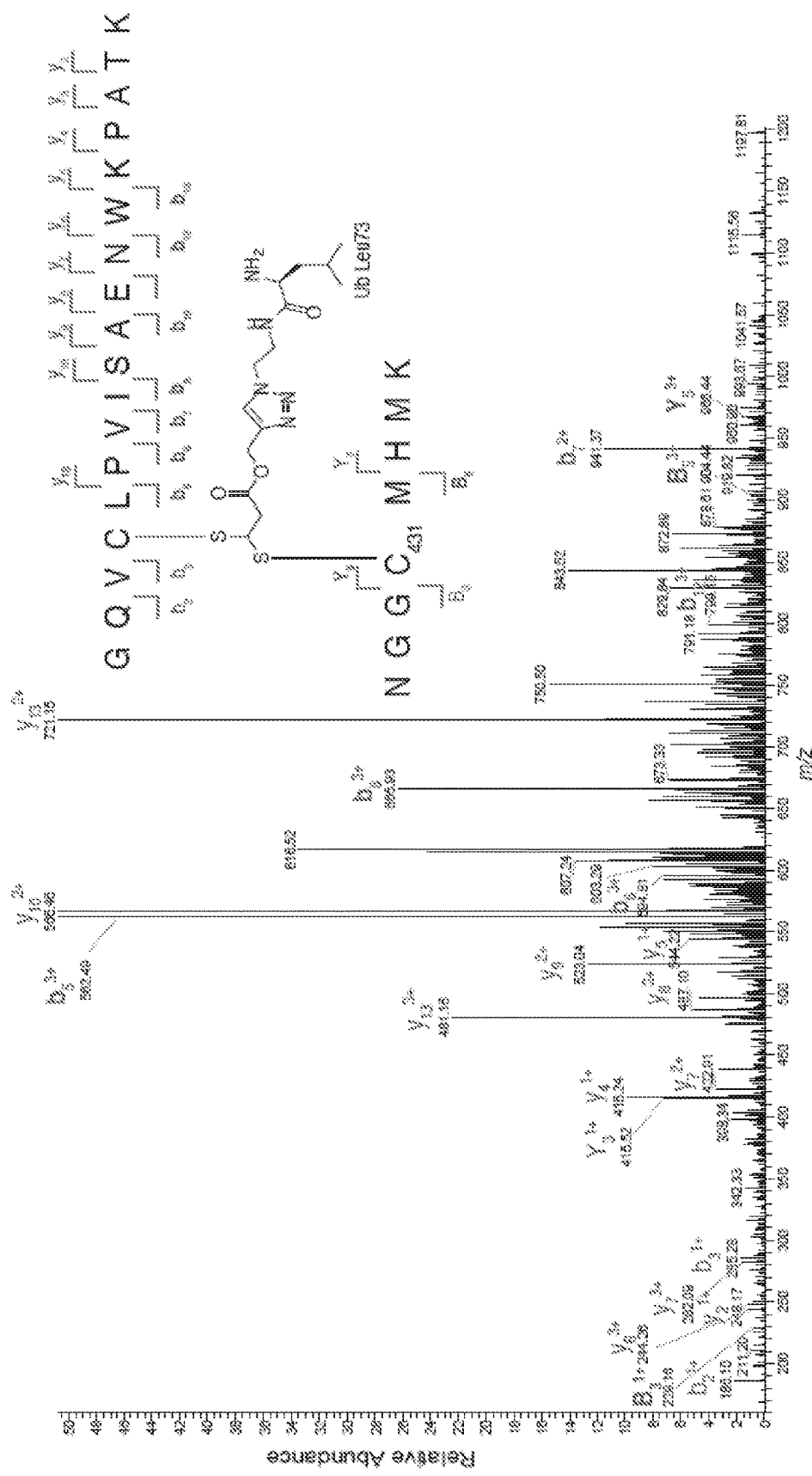

We next confirmed that our probes were labelling the catalytic C431 residue in Parkin. We initially generated phosphorylated Cys431Ser (C431S) mutant Parkin (p-Parkin C431S) that was ~40% phosphorylated. Parallel profiling of p-Parkin WT and p-Parkin C431S, and tryptic MS/MS sequencing of the cross-linked peptide, confirmed probe labelling of C431 (FIGS. 7b and c). Taken together with the F63A experiment, these results indicate that our probes engage Parkin via a mechanism consistent with E2 binding and cysteine-cysteine juxtaposition of the catalytic C85 residue in UBE2L3 and C431 of Parkin. Discrepancies between probe labelling and multiple turnover assays would be expected, as probe signal is directly proportional to the fraction of active protein. On the other hand, processive ubiquitination can be achieved by catalytic amounts of active E3. Furthermore, the kinetics of transthiolation will differ from those of cysteine addition to the AVS electrophile.

Figure 7D:
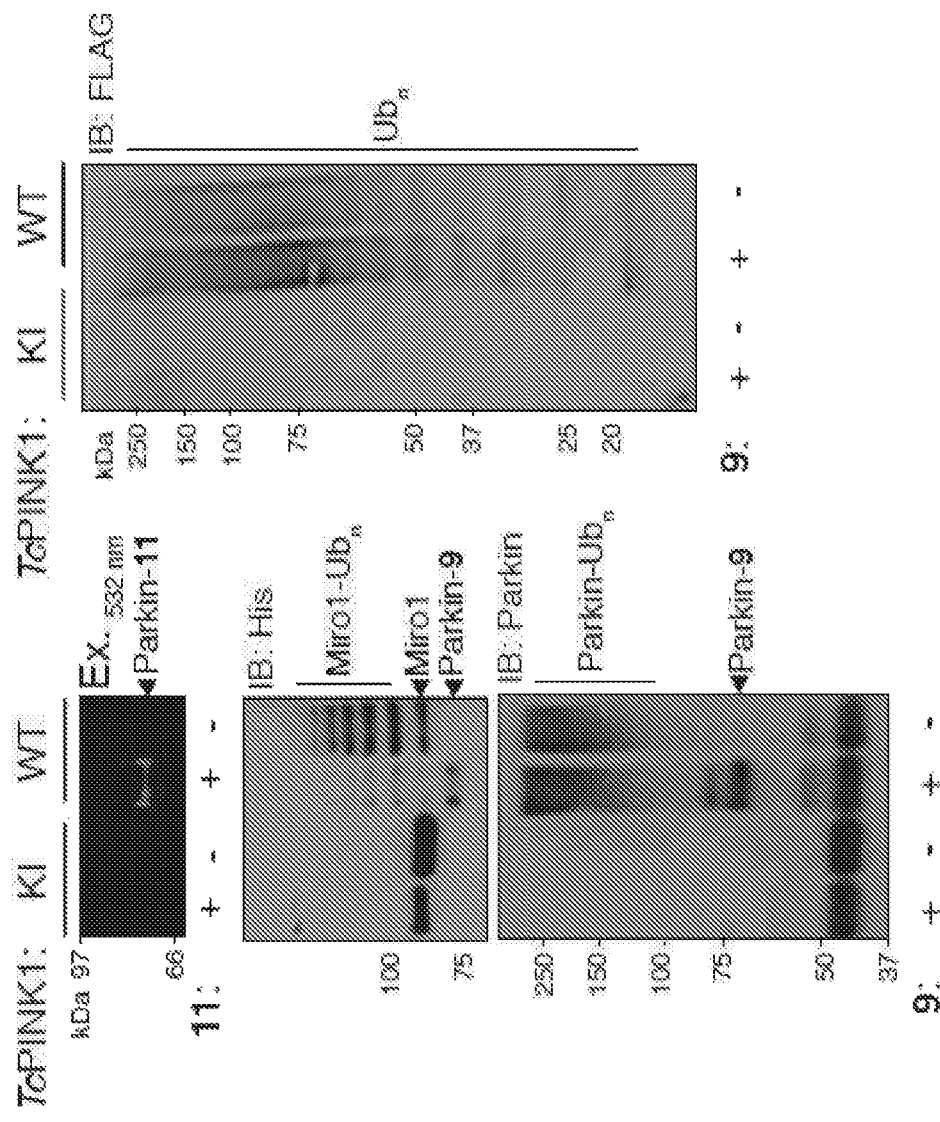

To further confirm that labelling was consistent with Parkin E3 ligase activity we carried out post-probe labelling of Parkin ubiquitination assays that provided three independent readouts of Parkin activity (FIG. 7d). In these experiments Parkin was activated by in situ phosphorylation with WT Tribolium castaneum PINK1 (TcPINK1 WT) in the presence of E1, UBE2L3, ATP and the substrate Miro1 that has been demonstrated to be a direct substrate of Parkin both in vitro and in cells 17,50. As a negative control, parallel assays were performed with kinase inactive PINK1 (TcPINK1 KI). We also deployed the fluorescent probe 11 which allowed rapid profiling by in-gel fluorescence and provided an orthogonal readout to anti-His immunoblotting since the latter also detected Miro1 substrate ubiquitination. These assays confirmed that probe labelling of Parkin strictly correlated with the positive activity readouts of Parkin E3 ligase activity, namely autoubiquitination, multi-mono ubiquitination of the Parkin substrate Miro1 and free poly-Ub chain formation.

We next tested whether probes 9 and 10 also labelled DUBs or if they were susceptible to DUB-mediated hydrolytic degradation, both of which would restrict the utility of the probes. We found that that whilst the DUB ABP propargylated-Ub (Ub-Alk) 51,52 efficiently labelled DUBs from 3 different subfamilies (USP, OTU and UCH), probes 9 and 10 exhibited no labelling, nor where they degraded by DUB isopeptidase activity.

p-Ub and p-Parkin are Strictly Required for Parkin Transthiolation Activity

To gain a further understanding of the critical determinants of Parkin activity we next carried out a more comprehensive profiling experiment using probe 9 and combinations of Parkin and p-Parkin together with Ub and p-Ub. We also included the first generation UBE2L3-VME probe 36 to assess the role of the Ub component in E2-Ub for adopting a cysteine-cysteine juxtaposition Parkin. Interestingly, detectable labelling was only observed with 9 and p-Parkin in the presence of p-Ub suggesting that both phosphorylation events are critical for optimal Parkin transthiolation activity (FIG. 8). Interestingly, this result indicates that p-Ub is not redundant to Parkin activity after Parkin phosphorylation. PINK1-dependant phosphorylation of mitochondrial Ub is the primary mitophagy signal and Parkin serves to amplify this signal[39]. Therefore, maintaining p-Ub dependence on optimal Parkin activity could continuously ensure Parkin activity closely correlates with the levels of the p-Ub primary signal. Furthermore, UBE2L3-VME bears a chemically similar thioacrylate electrophile to 9 but does not contain the Ub component. However, UBE2L3-VME did not undergo labelling of p-Parkin/p-Ub (FIG. 8). This result demonstrated that the Ub component in E2-Ub is required for adoption of a conformation where catalytic cysteines are juxtaposed. This would serve as a mechanism to prevent non-productive sequestration of uncharged E2. It is likely that the Ub component binds Parkin and this binding mode is recapitulated by Ub-based probes explaining their activity towards C431.

Rapid Profiling of Parkin Disease Mutants Affect Parkin Transthiolation Activity As direct, rapid and quantitative profiling of Parkin transthiolation activity could be carried out with fluorescent probe 11, we next profiled a panel of recombinant Parkin disease mutants (K27N, R33Q, R42P, A46P, S65A, K161N, K211N, R275W, G328E, T415N, G430D and C431 F) in parallel, with the non-phosphorylatable S65A mutant, that had been treated with WT Pediculus humanus corporis PINK1 (PhPINK1) in the presence of Ub, to assess activity (FIGS. 9a and b). Relative to Parkin WT, mutant-probe labelling signals fell into 3 classes: moderately deactivating, activating and inactive. Quantification of the fluorescent probe labelled bands was carried out revealing the following fold changes in transthiolation activity relative to Parkin WT: K27N (0.7-fold), R33Q (1.6-fold), R42P (1.3-fold) and G328E (0.7-fold). All other mutants did not undergo detectable probe labelling suggestive of enzyme inactivity. These data illustrate that for all patient mutants tested the observed effects on activity can be directly assigned to alterations in transthiolation activity rather than the latter step of Ub transfer to substrate. As these mutations spanned the full-length of the protein, this indicates that transthiolation activity is dependent on all of the domains within Parkin and provides a unifying pathogenic basis, despite their disparate distribution throughout the Parkin polypeptide.

Determinants of Parkin Activity in the Context of PINK1-Parkin Signalling in Cells We next profiled the activity of Parkin using probe 9 in cells by analysing untagged Parkin WT, Parkin S65A and Parkin H302A stably expressing HeLa cells. The H302A mutation significantly impairs p-Ub binding 25,26,54 therefore in combination with S65A, the effects of Ub and Parkin phosphorylation in the context of PINK1-Parkin signalling could be assessed by probe profiling of cell extracts. HeLa cells were chosen as they contain undetectable levels of endogenous Parkin yet support activation of exogenous Parkin in response to mitochondrial depolarization[39]. We treated HeLa cells expressing the various forms of Parkin with CCCP for 3 h, in parallel with untreated cells, and then extracted cellular proteomes by mild lysis by sonication. Extracts where then profiled with probe 9 (5 μM) for 4 h and were then resolved by SDS-PAGE and immunoblotted against total Parkin and p-SerS65-Parkin specific antibodies (FIG. 10). As expected, no phosphorylation of Parkin or probe labelling was observed in the absence of CCCP treatment for Parkin WT or either of the Parkin mutants. However, after CCCP treatment, total Parkin immunoblotting revealed a small pool of Parkin WT was activated as judged by the presence of a new band corresponding to Parkin WT labelled with 9. Probe labelling was also observed by p-Parkin immunoblotting and labelling efficiency of the phosphorylated pool was significantly greater than for the total pool. In contrast to Parkin WT, no labelling was observed with Parkin S65A indicating that that phosphorylation at S65 of Parkin in cells plays an important role in Parkin activation, consistent with earlier findings 20,21. UBE2L3-VME failed to label under these conditions further highlighting the role of the Ub component in E2~Ub for cysteine-cysteine juxtaposition. Strikingly, Parkin H302A exhibited reduced phosphorylation and probe labelling was significantly impaired. This result supports a model where the primary mechanism of Parkin activation in response to mitochondrial depolarization involves initial p-Ub binding to Parkin that primes it for PINK1 phosphorylation and optimal activation. p-Parkin has enhanced affinity for p-Ub, and our in-vitro data indicate that both p-Ub and p-Parkin are required for optimal activity. This supports a new modality of the Parkin feed-forward mechanism ensuring Parkin is not only recruited to mitochondrial p-Ub and phosphorylated by PINK1, but p-Ub abundance is continuously sensed, post phosphorylation of Parkin, and further drives its activation.

Profiling of Endogenous Parkin Activity in Dopaminergic SH-SY5Y Cellular Proteomes To date the majority of studies in cells examining Parkin activation in response to mitochondrial depolarisation have employed over-expression studies 29,30,55 (often with N-terminal tagging that can aberrantly activate Parkin) and studies on endogenous Parkin have been limited. We therefore used probe 9 to detect the activation status of endogenous Parkin in response to mitochondrial uncoupling in dopaminergic neuroblastoma SH-SY5Y cells. Cells were untreated or treated with CCCP (10 μM) for 3, 6 and 9 h and then lysed. Profiling was then carried out with the inclusion of inactive probe 9 F63A as a further control.

Figure 10B:
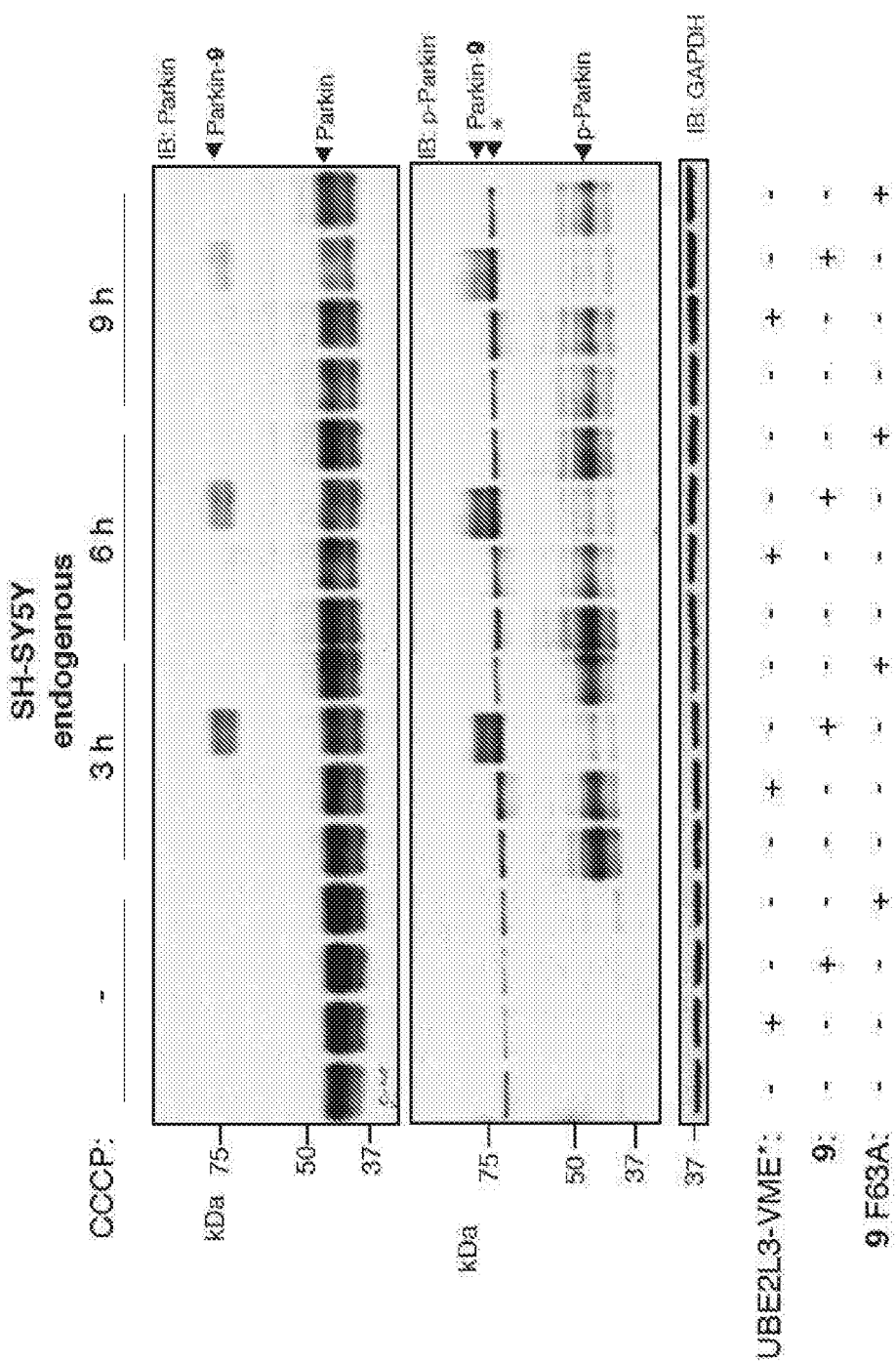

Probe labelling and phosphorylation was undetectable in untreated cells (FIG. 10b). However, probe labelling and Parkin phosphorylation was detected in CCCP treated cells and peaked between 3 and 6 h. As expected, 9 F63A failed to label under any conditions. Labelling efficiency of the total Parkin and p-Parkin pools were ~50% and >95%, respectively, considerably higher than that observed with Parkin overexpression in Hela cells (likely attributable to stoichiometric imbalance where factors such as PINK1, p-Ub and mitochondrial abundance become limiting). Overall, our probe has provided the first physiological and quantitative assessment of the stoichiometry of endogenous Parkin activation by CCCP treatment. The finding >50% highlights the rapid activation induced by PINK1-dependent phosphorylation of Parkin and Ub. Furthermore, the finding that probe labelling of the phosphorylated pool approached 100% underscores the significance of the phosphorylation of endogenous Parkin for its activation. A noteworthy observation was that no autoubiquitination of endogenous activated Parkin was observed indicating that clearance is not rate limited by its activation. These findings highlight the importance of our probes for determining the activation status of an endogenous E3 ligase. Interestingly, over the time course degradation of Parkin was observed whilst probe labelling efficiency remained unchanged (FIG. 10b). This suggests that the Parkin activation signal is attenuated by degradation of Parkin in the activated state rather than its deactivation.

Discussion

Herein we have reported the construction of a new class of activity-based probe (ABP) that can be used to profile the activity of the PD-linked enzyme Parkin in vitro and in cellular proteomes. In vitro profiling experiments of recombinant Parkin demonstrates that phosphorylation of Parkin and Ub contribute to optimal transthiolation activity. This result suggests that p-Ub binding to Parkin in cells primes it for optimal phosphorylation and activation by PINK1. p-Ub then continues to drive optimal activity of p-Parkin activity ensuring p-Ub levels are continuously sensed.

We also described the construction of fluorescent probe 11. This provides a rapid platform for profiling ligase activity by direct in-gel fluorescence scanning revealing a distinct transthiolation activity signature of Parkin patient mutations. Strikingly, this revealed that all mutations exert their pathogenicity by altering transthiolation activity. Probe profiling of endogenous Parkin in familial and sporadic patient samples could hence provide a much needed biomarker for early diagnosis and prognosis of PD.

We also showed that our probes can be used to profile the activation status of endogenous Parkin in neuronal SH-SY5Y cells. These data clearly demonstrated that endogenous Parkin is phosphorylated and 50% is activated in response to protonophore treatment, whereas activation of the phosphorylated pool approaches 100%. Furthermore, time course profiling demonstrated that Parkin levels and probe signals reduce after activation, suggestive of Parkin clearance in the activated state. To our knowledge our analysis also represents the first report that Parkin can be phosphorylated at Ser65 under endogenous conditions providing physiological evidence for Parkin phosphorylation at Ser65.

A large body of powerful experimental platforms have been developed that are based on fluorescent ABPs. These include in-gel based multiplexed profiling of endogenous enzyme activities in cellular proteomes, inhibitor screening and inhibitor selectivity profiling[37]. Fluorescent probe 11 should be valuable tool for discovering small molecules that activate the transthiolation activity of Parkin. In principle, high affinity enrichment tags such as azide-functionalized biotin could also be conjugated to our probes allowing multiplexed profiling in combination with E3 ligase activity quantification and identification. As E3 ligase activities are stringently regulated and dysregulated in pathophysiology, we envisage that such ABPP platforms based on our probes will provide great insight into the roles of other E3 ligases in disease. This could lead to novel biomarkers, therapeutic targets and as drivers for further biological investigation.

REFERENCES

25 Smit, J. J. & Sixma, T. K. RBR E3-ligases at work. *EMBO Rep* 15, 142-154, doi:10.1002/embr.201338166 (2014).
26 Pickrell, A. M. & Youle, R. J. The roles of PINK1, parkin, and mitochondrial fidelity in Parkinson's disease. *Neuron* 85, 257-273, doi:10.1016/j.neuron.2014.12.007 (2015).
27 Kazlauskaite, A. et al. Parkin is activated by PINK1-dependent phosphorylation of ubiquitin at Ser65. *The Biochemical journal* 460, 127-139, doi:10.1042/BJ20140334 (2014).
28 Wauer, T., Simicek, M., Schubert, A. & Komander, D. Mechanism of phospho-ubiquitin-induced PARKIN activation. *Nature*, doi:10.1038/nature14879 (2015).
29 Stanley, M. et al. Orthogonal Thiol Functionalization at a Single Atomic Center for Profiling Transthiolation Activity of E1 Activating Enzymes. *ACS chemical biology*, doi:10.1021/acschembio.5b00118 (2015).
30 Ye, Y. & Rape, M. Building ubiquitin chains: E2 enzymes at work. *Nat Rev Mol Cell Biol* 10, 755-764, doi:10.1038/nrm2780 (2009).
31 Komander, D., Clague, M. J. & Urbé, S. Breaking the chains: structure and function of the deubiquitinases. *Nat Rev Mol Cell Biol* 10, 550-563, doi:10.1038/nrm2731 (2009).
32 Hong, V., Presolski, S. I., Ma, C. & Finn, M. G. Analysis and optimization of copper-catalyzed azide-alkyne cycloaddition for bioconjugation. *Angew Chem Int Ed Engl* 48, 9879-9883, doi:10.1002/anie.200905087 (2009).
33 Borodovsky, A. et al. Chemistry-based functional proteomics reveals novel members of the deubiquitinating enzyme family. *Chemistry and biology* 9, 1149-1159 (2002).
34 Dadová, J. et al. Vinylsulfonamide and acrylamide modification of DNA for cross-linking with proteins. *Angew Chem Int Ed Engl* 52, 10515-10518, doi:10.1002/anie.201303577 (2013).
Katrun, P. & Chiampanichayakul, S. PhI(OAc)2/KI-Mediated Reaction of Aryl Sulfinates with Alkenes, Alkynes, and α,β-Unsaturated Carbonyl Compounds: Synthesis of Vinyl Sulfones and β-Iodovinyl Sulfones. *Eur J Org Chem*, 5633-5641, (2010).
36 Cui, C., Zhao, W., Chen, J., Wang, J. & Li, Q. Elimination of in vivo cleavage between target protein and intein in the intein-mediated protein purification systems. *Protein expression and purification* 50, 74-81, doi:10.1016/j.pep.2006.05.019 (2006).
37 Niphakis, M. J. & Cravatt, B. F. Enzyme inhibitor discovery by activity-based protein profiling. *Annu Rev Biochem* 83, 341-377, doi:10.1146/annurev-biochem-060713-035708 (2014).
38 Weissman, A. M. Themes and variations on ubiquitylation. *Nat Rev Mol Cell Biol* 2, 169-178, doi:10.1038/35056563 (2001).
39 Lazarou, M. et al. The ubiquitin kinase PINK1 recruits autophagy receptors to induce mitophagy. *Nature*, doi:10.1038/nature14893 (2015).

The invention claimed is:

1. An activated enzyme conjugate probe of conjugate (V) below:

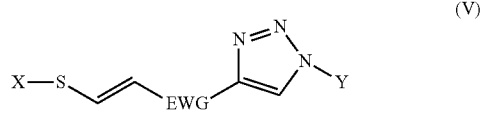

(V)

wherein X is an enzyme, EWG is an electron withdrawing group and Y is a substrate or ligand for the enzyme.

2. The activated enzyme conjugate probe according to claim 1 wherein the enzyme contains a cysteine.

3. The activated enzyme conjugate probe according to claim 2 wherein the cysteine may be a naturally occurring cysteine in the enzyme, or may be introduced into the enzyme.

4. The activated enzyme conjugate probe according to claim 1 wherein Y is ubiquitin or ubiquitin-like protein.

5. The activated enzyme conjugate probe according to claim 1 wherein X is a ubiquitin or ubiquitin-like conjugating enzyme (E2).

6. The activated enzyme conjugate probe according to claim 5 wherein the E2 enzyme is selected from the group consisting of UBE2D1, UBE2D1 C86, UBE2D1 C86 AzF3 (X), UBE2D2, UBE2D3, UBE2L3*, UBE2L3**, UBE2L6*, UBE2L6**, UBE2N, UBE2H, UBE2I and UBE2M.

7. The activated enzyme conjugate probe according to claim 1 further modified by incorporation of a tag.

8. The activated enzyme conjugate probe according to claim 1, wherein the electron withdrawing group is selected from the group consisting of: —COO— and —CONH—.

* * * * *